US012622170B2

(12) United States Patent
Tanabe et al.

(10) Patent No.: US 12,622,170 B2
(45) Date of Patent: *May 5, 2026

(54) FLUORESCENT ORGANIC LIGHT EMITTING ELEMENTS HAVING HIGH EFFICIENCY

(71) Applicant: UDC IRELAND LIMITED, Dublin (IE)

(72) Inventors: Junichi Tanabe, Dublin (IE); Christian Lennartz, Dublin (IE)

(73) Assignee: UDC Ireland, Dublin (IE)

( * ) Notice: Subject to any disclaimer, the term of this patent is extended or adjusted under 35 U.S.C. 154(b) by 48 days.

This patent is subject to a terminal disclaimer.

(21) Appl. No.: 18/352,764

(22) Filed: Jul. 14, 2023

(65) Prior Publication Data

US 2023/0380277 A1 Nov. 23, 2023

Related U.S. Application Data

(63) Continuation of application No. 16/792,983, filed on Feb. 18, 2020, now Pat. No. 11,706,978, which is a continuation of application No. 15/312,115, filed as application No. PCT/EP2015/060305 on May 11, 2015, now Pat. No. 10,586,930.

(30) Foreign Application Priority Data

May 19, 2014 (EP) .................................... 14168826

(51) Int. Cl.

| | |
|---|---|
| ***H01L 51/00*** | (2006.01) |
| ***C07D 487/04*** | (2006.01) |
| ***C07D 498/04*** | (2006.01) |
| ***C07D 513/04*** | (2006.01) |
| ***C09B 15/00*** | (2006.01) |
| ***C09B 17/00*** | (2006.01) |
| ***C09B 19/00*** | (2006.01) |
| ***C09B 21/00*** | (2006.01) |
| ***C09B 57/00*** | (2006.01) |
| ***C09K 11/02*** | (2006.01) |
| ***C09K 11/06*** | (2006.01) |
| ***H10K 85/60*** | (2023.01) |
| *H10K 50/11* | (2023.01) |
| *H10K 50/12* | (2023.01) |

(52) U.S. Cl.

CPC ......... *H10K 85/657* (2023.02); *C07D 487/04* (2013.01); *C07D 498/04* (2013.01); *C07D 513/04* (2013.01); *C09B 15/00* (2013.01); *C09B 17/00* (2013.01); *C09B 19/00* (2013.01); *C09B 21/00* (2013.01); *C09B 57/00* (2013.01); *C09B 57/008* (2013.01); *C09K 11/02* (2013.01); *C09K 11/06* (2013.01); *H10K 85/6572* (2023.02); *C09K 2211/1007* (2013.01); *C09K 2211/1033* (2013.01); *C09K 2211/1037* (2013.01); *H10K 50/11* (2023.02); *H10K 50/121* (2023.02); *H10K 85/622* (2023.02); *H10K 85/654* (2023.02); *H10K 85/6576* (2023.02); *Y02E 10/549* (2013.01)

(58) Field of Classification Search

CPC ............ H10K 85/657; H10K 85/6572; H10K 85/654; H10K 50/121; H10K 85/622; H10K 50/11; H10K 85/6576; C07D 487/04; C07D 498/04; C07D 513/04; C09B 15/00; C09B 17/00; C09B 19/00; C09B 21/00; C09B 57/00; C09B 57/008; C09K 11/02; C09K 11/06; C09K 2211/1007; C09K 2211/1033; C09K 2211/1037

See application file for complete search history.

(56) References Cited

U.S. PATENT DOCUMENTS 2,807,622 A 9/1957 Holbro
5,599,899 A 2/1997 Jenekhe
(Continued)

FOREIGN PATENT DOCUMENTS

CN 105073756 A 11/2015
EP 0786926 7/1997
(Continued)

OTHER PUBLICATIONS

El-Maghraby, M. A. et al., "Synthesis of new 2:6 bis-substituted glycyl- and phenoxyacetylbenzo[1,2-d;4,5-d] dioxazole", Database CA, Chemical Abstracts Service, Columbus, Ohio, US, (1979), Database accession No. 1979:22863, URL: STN, XP002727013.
(Continued)

*Primary Examiner* — Haidung D Nguyen
(74) *Attorney, Agent, or Firm* — Riverside Law LLP

(57) ABSTRACT

The present invention relates to organic light emitting elements, comprising thermally activated delayed fluorescence (TADF) emitters and/or hosts of formula (I)

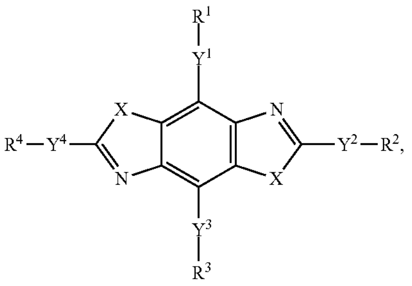

which have a sufficiently small energy gap between $S_1$ and $T_1$ ($\Delta E_{ST}$) to enable up-conversion of the triplet exciton from $T_1$ to $S_1$. The organic light emitting elements show high electroluminescent efficiency.

18 Claims, No Drawings

(56) References Cited

U.S. PATENT DOCUMENTS

| | | | | |
|---|---|---|---|---|
| 9,793,492 | B2 | 10/2017 | Sagara | |
| 9,853,224 | B2 | 12/2017 | Tanabe | |
| 9,917,260 | B2 | 3/2018 | Sundarraj | |
| 10,333,078 | B2 | 6/2019 | Tanabe | |
| 10,586,930 | B2 * | 3/2020 | Tanabe | C09B 19/00 |
| 11,706,978 | B2 * | 7/2023 | Tanabe | C09B 15/00 |
| 2009/0108733 | A1 | 4/2009 | Chin | |
| 2012/0273732 | A1 | 11/2012 | Jenekhe | |
| 2013/0161437 | A1 | 6/2013 | Ono | |
| 2014/0124035 | A1 | 5/2014 | Byrne | |
| 2014/0275459 | A1 | 9/2014 | Jeffries-El | |
| 2015/0239880 | A1 | 8/2015 | Adachi | |
| 2016/0005978 | A1 | 1/2016 | Sagara | |

FOREIGN PATENT DOCUMENTS

| | | | |
|---|---|---|---|
| EP | 2862913 | | 4/2015 |
| JP | H09268283 | | 10/1997 |
| JP | H10340786 | A | 12/1998 |
| JP | 2005082703 | A | 3/2005 |
| KR | 20140060247 | | 5/2014 |
| WO | 2011105700 | A1 | 9/2011 |
| WO | 2012130709 | A1 | 10/2012 |
| WO | 2014044722 | | 3/2014 |
| WO | 2014126200 | A1 | 8/2014 |
| WO | 2015176981 | | 11/2015 |
| WO | 2014034535 | | 8/2016 |

OTHER PUBLICATIONS

El-Maghraby, M. A. et al., “Synthesis of new 2:6 bis-substituted glycyl- and phenoxyacetylbenzo[1,2-d;4,5-d] dioxazole”, Journal of the Indian Chemical Society, 1978, 55(1), 44-7.

Kim, I. T. et al., “Synthesis, characterization, and properties of a new thiophene-benzobisthiazole copolymer”, Synthetic Metals, 2006, 156:38-41.

M.A. El-Maghraby et al., “Synthesis of New 2:6 Bis Substituted Glycyl and Phenoxy Acetyl Benzo [1,2-d; 4,5-d] Bisoxazole”, J. Indian Chem. Soc., vol. LV, Jan. 1978, 44-47. (Year: 1978).

Musabbir A. Saeed et al., “Benzobisoxazole Cruciforms as Fluorescent Sensors”, Acc. Chem. Res., 2014, 47:2074-2083.

Zylon (TM, Wikipedia, 4 pages, May 7, 2019 (Year:2019).

* cited by examiner

FLUORESCENT ORGANIC LIGHT EMITTING ELEMENTS HAVING HIGH EFFICIENCY

CROSS-REFERENCE TO RELATED APPLICATIONS

This application is a continuation of U.S. application Ser. No. 16/792,983, filed Feb. 18, 2020, now allowed, which is a continuation of U.S. application Ser. No. 15/312,115, filed Nov. 17, 2016, now U.S. Pat. No. 10,586,930, which is a U.S. National Stage Application filed under 35 U.S.C. § 371 claiming benefit to International Patent Application No. PCT/EP2015/060305, filed May 11, 2015, which is entitled to priority under 35 U.S.C. § 119 (a)-(d) to EP Application Serial No. 14168826.7, filed May 19, 2014, each of which is hereby incorporated by reference in its entirety.

The present invention relates to organic light emitting elements, comprising thermally activated delayed fluorescence (TADF) emitters and/or hosts of formula (I), which have a sufficiently small energy gap between $S_1$ and $T_1$ ($\Delta E_{ST}$) to enable up-conversion of the triplet exciton from $T_1$ to $S_1$. The organic light emitting elements show high electroluminescent efficiency.

The development of OLED luminescent materials is an important issue and these materials have been classified into two major categories. The first is fluorescent materials, which can harvest only the singlet excitons (25%) that are generated by electrical excitation. The second is phosphorescent materials, which can harvest the triplet excitons generated (75%). The branching ratio of singlet and triplet excitons is 1:3. Therefore, in recent devices, phosphorescent materials and their related technologies have been indispensable to obtain high EL efficiency. However, phosphorescent materials generally contain a rare metal element such as Ir or Pt. These metals are rather expensive and are dependent on limited global resources.

Recently, the alternative concept of thermally activated delayed fluorescence (TADF) as a third generation luminescent material, instead of the conventional fluorescent and phosphorescent materials was described by C. Adachi et al. in Adv. Mater., 2009, 21, 4802; Appl. Phys. Lett., 2011, 98, 083302 and Chem. Commun., 2012, 48, 9580.

The TADF strongly depends on HOMO-LUMO separation in a single molecule. TADF materials have a sufficiently small energy gap between $S_1$ and $T_1$ ($\Delta E_{ST}$) to enable up-conversion of the triplet exciton from $T_1$ to $S_1$. This small $\Delta E_{ST}$ enables TADF materials to realize 100% of the exciton formation generated by electrical excitation at $S_1$.

WO2011105700 relates to an electroluminescent compound represented by formula 1 or 2:

(1)

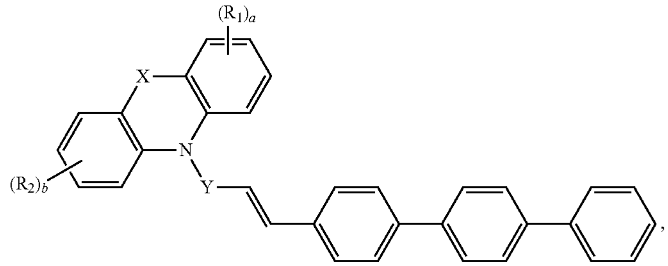

, or (2)

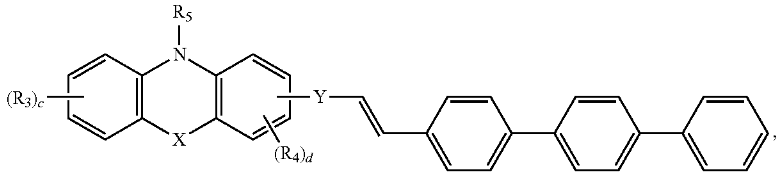

, wherein $R_1$ through $R_5$ independently represent hydrogen, (C1-C60)alkyl, (C3-C60)cycloalkyl, (C6-C60)aryl, (C2-60)heteroaryl containing one or more heteroatom (s) selected from N, O, S, P, Si and Se, (C1-60)alkoxy, (C1-C60)alkylthio, (C6-60)aryloxy, (C6-C60)arylthio, (C6-30)aryl(C1-C30)alkylamino, tri(C1-C30)alkylsilyl, di(C1-C30)alkyl(C6-C30)arylsilyl or tri(C6-C30) arylsilyl;

X represents a chemical bond, $-(CR_6R_7)_m-$, $-N(R_8)-$, $-Si(R_9)(R_{10})-$, $-O-$, $-S-$, $-Se-$ or $-(CR_{11})C{=}C(R_{12})-$;

$R_6$ through $R_{12}$ independently represent hydrogen, (C1-C60)alkyl, (C3-C60)cycloalkyl, (C6-C60)aryl, (C2-60) heteroaryl containing one or more heteroatom(s) selected from N, O, S, Si and Se, (C1-60)alkoxy, (C1-C60)alkylthio, (C6-60)aryloxy, (C6-C60)arylthio, mono- or di(C1-60)alkylamino, mono- or di(C6-60) arylamino, (C6-30)aryl(C1-C30)alkylamino, tri(C1-C30)alkylsilyl, di(C1-C30)alkyl(C6-C30)arylsilyl or tri(C6-C30)arylsilyl, or $R_6$ and $R_7$, $R_9$ and $R_{10}$, and $R_{11}$ and $R_{12}$ are linked via (C3-C60)alkylene or (C3-C60) alkenylene with or without a fused ring to form an aliphatic ring or a mono- or polycyclic aromatic ring;

Y represents (C6-C60)arylene, adamantylene, (C3-C60) heteroarylene containing one or more heteroatom(s) selected from N, O, S, P, Si and Se, or . . . ; and their use in organic light emitting devices as fluorescent dopant.

The synthesis of 2,2'-diphenothiazin-10-yl-1,1'benzo[1,2-d,4,5-d]bisoxazole-2,6-diyl-bisethanone is described in M. A. El-Maghraby, M. A. Abbady, Journal of the Indian Chemical Society 55 (1978) 44-47.

In Tae Kim et al., Synthetic Metals 156 (2006) 38-41 reports that Stille coupling reaction of 4,8-dibromo-2,6-dihexyl-benzo[1,2-d:4,5-d']bisthiazole and 2,5-bis(trimethylstannyl)thiophene afford a new conjugated conducting copolymer 1.

JP10340786 relates to compounds for use in an organic electroluminescent element represented by formulas (I)

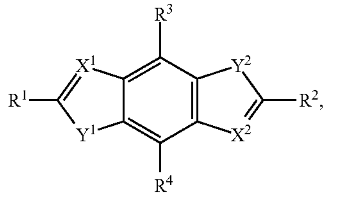

(II)

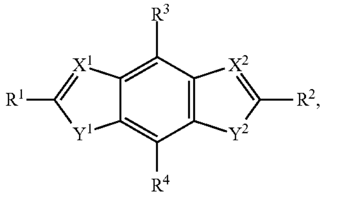

such as, for example,

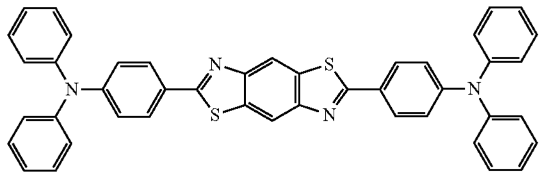

and

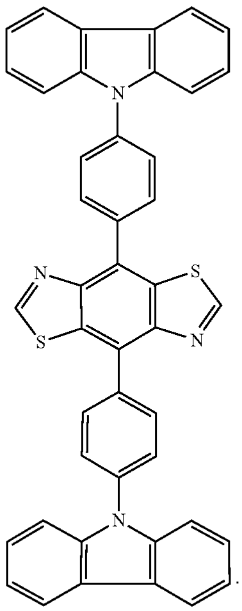

In the formulas $X^1$ and $X^2$ independently represent N or CH, $Y^1$ and $Y^2$ independently represent S, O, N—Z, Z is a hydrogen atom, a substituted or non-substituted alkyl group, a substituted or non-substituted cycloalkyl group, a substituted or non-substituted heterocyclic group. $R^1$-$R^4$ independently represent respectively a hydrogen atom, a halogen atom, a cyano group, a nitro group, a substituted or non-substituted alkyl group, a substituted or non-substituted aryl group, a substituted or non-substituted alkoxy group, a substituted or non-substituted aryl oxy group, a substituted or non-substituted alkyl thio group, a substituted or non-substituted cycloalkyl group, a substituted or non-substituted heterocyclic group, a substituted or non-substituted amino group, or the like.

KR20110085784A relates to organic electroluminescent compounds formula (I)

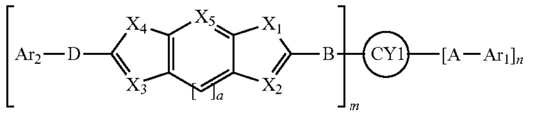

or (II)

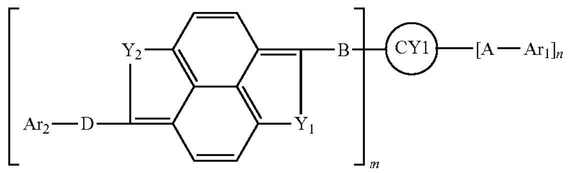

with excellent luminous efficiency and their use in an organic light-emitting devices. In the chemical formulas, CY1 is either a $C_{10}$-$C_{30}$ aromatic ring or a $C_{10}$-$C_{30}$ aromatic hetero ring. A, B, and D are a covalently bonded, and substituted or non-substituted $C_6$-$C_{50}$ arylene group, or a substituted or non-substituted $C_2$-$C_{50}$ heteroarylene group.

KR2011079401 relates to organic light emitting diodes comprising a first electrode, a second electrode, and at least one layer of organic membrane between the first electrode and the second electrode. The organic membrane comprises an organic luminescent compound in chemical formula (a)

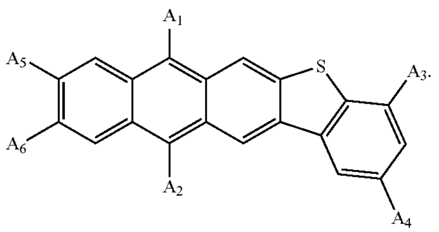

$A_1$, $A_2$, $A_3$, $A_4$, $A_5$ and $A_6$ is respectively and independently hydrogen, a substituted or non-substituted $C_{6-50}$ aryl, a substituted or non-substituted $C_{2-50}$ heteroaryl, a substituted or non-substituted $C_{2-50}$ cycloalkyl, or a substituted or non-substituted $C_{2-50}$ heterocycloalkyl.

KR101160670 relates to organic light emitting compounds represented by chemical formula (I)

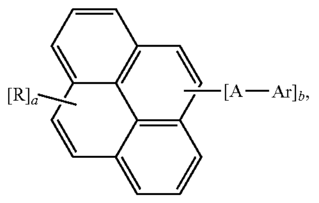

such as, for example,

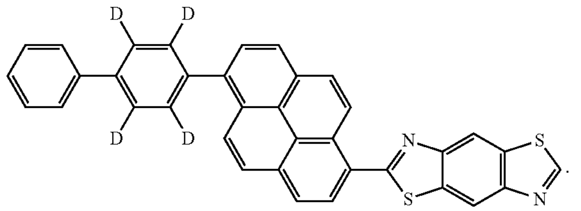 [SMILES: [2H]c1c([2H])c(-c2ccc3ccc4c(-c5nc6cc7scnc7cc6s5)ccc5ccc2c3c54)c([2H])c([2H])c1-c1ccccc1]

In chemical formula I, R is hydrogen or deuterium; A is a covalent bond, substituted or unsubstituted $C_6$-$C_{50}$ arylene, or substituted or unsubstituted $C_2$-$C_{50}$ heteroarylene; Ar is substituted or unsubstituted $C_6$-$C_{20}$ aryl, substituted or unsubstituted $C_2$-$C_{20}$ heteroaryl, or —$N(Z^1)(Z^2)$; a is an integer of 0-9; b is an integer of 1-10; and a+b=10.

JP2005082703 relates to a material for organic electroluminescent devices which comprises (A) a condensed heterocyclic compound in which same or different two or more nitrogen-containing rings are condensed directly or through other carbon ring or heterocyclic ring and (B) a phosphorescence luminescent material. The compound A is e.g. a compound represented by general formula

[1]

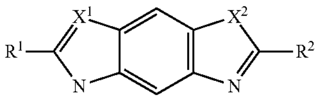

or

[2]

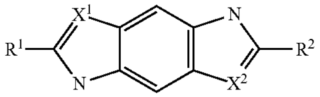

(wherein $X^1$ and $X^2$ are each O or the like; $R^1$ and $R^2$ are each an aryl group or the like).

WO2011105700 relates to organic electroluminescent compounds of formula

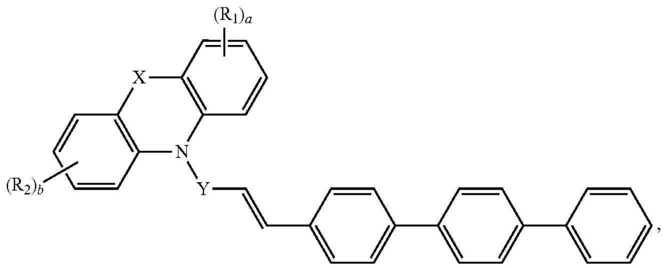

, or

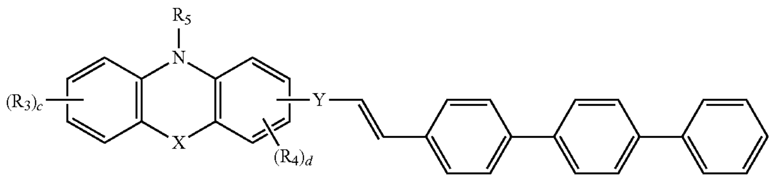

and organic electroluminescent devices comprising the same.

An object of the present invention is to provide a highly efficient and practically useful organic light-emitting element and an organic light-emitting material suitable for the organic light-emitting element. It has surprisingly been found that certain benzobisoxazole, benzobisthiazole and benzobisimidazole compounds emit delayed fluorescence and the use thereof in an organic light-emitting element provides a highly efficient organic EL element.

Accordingly, the present invention relates to compounds of formula (I)

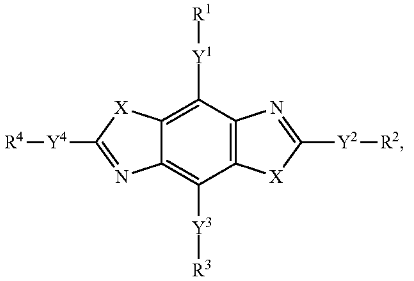

wherein

X is independently in each occurrence O, S or $NR^9$, $Y^1$, $Y^2$, $Y^3$ and $Y^4$ are independently of each other a direct bond, or a group of formula $-[A^1]-[A^2]_y-$, wherein $A^1$ and $A^2$ are independently of each other —CH═CH—, —C≡C— or a $C_6$-$C_{10}$arylene group, which may optionally be substituted by one or more $C_1$-$C_{25}$alkyl groups; y is 0, or 1; $R^1$, $R^2$, $R^3$ and $R^4$ are independently of each other H, D, F, Cl, a $C_1$-$C_{25}$alkyl group, a $C_1$-$C_{25}$alkoxy group, a $C_6$-$C_{10}$aryloxy group, or a donor group of formula (Xa)

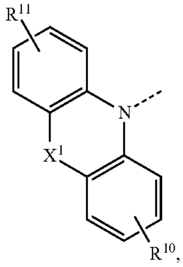

, or (Xd)

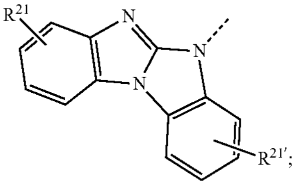

;

$X^1$ is O, S, $N(R^{15})$, C(=O), $C(R^{16})(R^{17})$, $B(R^{18})$, or $Si(R^{19})(R^{20})$, $R^9$ is H, a $C_1$-$C_{25}$alkyl group, or a $C_6$-$C_{10}$aryl group;

$R^{10}$, $R^{11}$, $R^{21}$ and $R^{21'}$ are independently of each other H, D, F, Cl, or a $C_1$-$C_{25}$alkyl group;

$R^{15}$, $R^{16}$, $R^{17}$, $R^{18}$, $R^{19}$ and $R^{20}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group; with the proviso that at least one donor group of formula (Xa), or (Xd) is present in the compound of formula (I).

The present invention is also directed to the use of compounds of formula (I) for generating delayed fluorescence emission.

E-type delayed fluorescence is defined herein as a process in which the first excited singlet state becomes populated by a thermally activated radiationless transition from the first excited triplet state.

Thermally activated delayed fluorescence (TADF, E-type delayed fluorescence) is a promising way to obtain a high efficiency of exciton formation by converting spin-forbidden triplet excitons up to the singlet level by the mechanism of reverse intersystem crossing (RISC).

In a TADF emitter, the upconversion mechanism uses the vibronic energy that, at sufficiently high temperatures 300 K), allows all of the excitons in an OLED to eventually produce light through singlet decay.

The present invention is also directed to an organic light-emitting element, comprising a compound of formula (I).

The organic light-emitting element offers an external quantum efficiency of more than 5%, especially more than 10% and reduced efficiency roll-off characteristics at high luminance.

The compound of formula (I) has preferably a difference between excited singlet energy and excited triplet energy ($\Delta E_{ST}$) of 0.5 eV or less, more preferably $\Delta E_{ST}$ of 0.35 eV or less, i.e. of 0.01 to 0.5 eV, especially 0.01 to 0.35 eV.

The determination of $\Delta E_{ST}$ can be carried either by quantum mechanical calculations (for example TD-DFT (time dependent density functional theory) calculations, for example with commercially available Gaussian 09 or ADF Amsterdam Density Functional software programs; for example as described in Adv. Mater. 2008, 20, 3325-3330), or experimentally.

Experimental Determination of $\Delta E_{ST}$:

i) $\Delta E_{ST}$ can be determined based on the information given in the following formula:

$$Int(S_1 \rightarrow S_0)/Int(T_1 \rightarrow T_0) = k(S_1)/k(T_1)\exp(-\Delta E/k_B T).$$

The intensities $Int(S_1 \rightarrow S_0)$ and $Int(T_1 \rightarrow T_0)$ can be determined spectroscopically by a spectrophotometer. A graph of the logarithmic intensity ratios $Int(S_1 \rightarrow S_0)/Int(T_1 \rightarrow T_0)$ measured at different temperatures versus the reciprocal of the absolute temperature T generally shows a straight line. The measurement is carried out in a temperature range from room temperature (300 K) to 77 K to 4.2 K (the temperature can be adjusted by means of a cryostat). The respective transitions ($S_1 \rightarrow S_0$) and ($T_1 \rightarrow T_0$) (band intensities) can be identified since the triplet transition is at lower energy than the singlet transition and increases in intensity with decreasing temperature. The measurements are usually performed in oxygen-free dilute solutions (about $10^{-2}$ $molL^{-1}$) or thin films of the respective compounds or doped films comprising the corresponding compounds.

The slope of the straight line mentioned above is $-\Delta E/k_B T$ With $k_B = 1.380\ 10^{-23}\ JK^{-1} = 0.695\ cm^{-1}\ K^{-1}$, $\Delta E_{ST}$ can be determined.

ii) $\Delta E_{ST}$ can also be determined by measuring the temperature dependency of the emission decay as known by a person skilled in the art.

iii) An approximate estimation of $\Delta E_{ST}$ can be achieved by recording the fluorescence and phosphorescence spectra at low temperature (for example 77 K or 4.2 K using a cryostat).

$\Delta E_{ST}$ then corresponds to an approximation of the energy difference between the high-energy rising edges of the fluorescence or phosphorescence band.

The compounds of formula (I) contain preferably one, or two donor groups of formula (Xa) and/or (Xd).

Among the compounds of formula (I) compounds of formula (Ia)

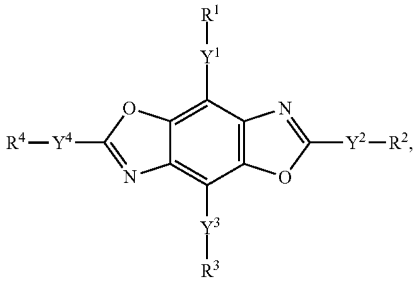

, (Ib)

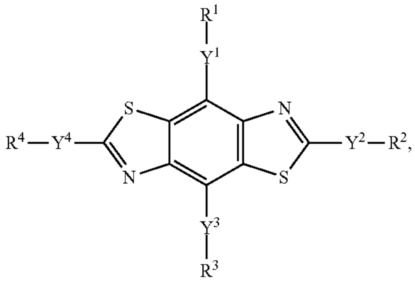

,

-continued (Ic)

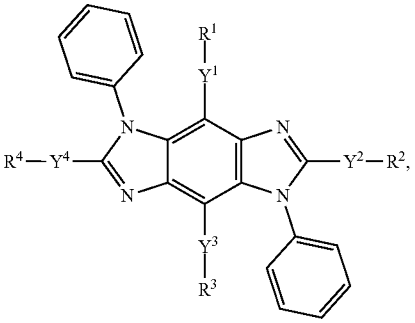

(Id)

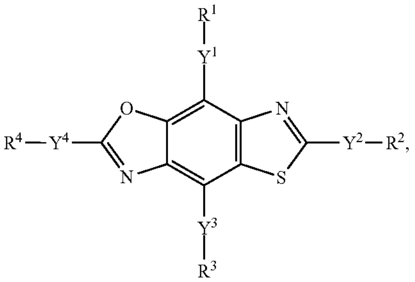

(Ie)

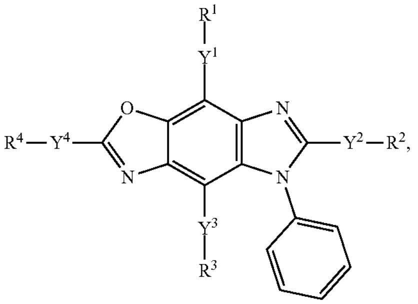

or (If)

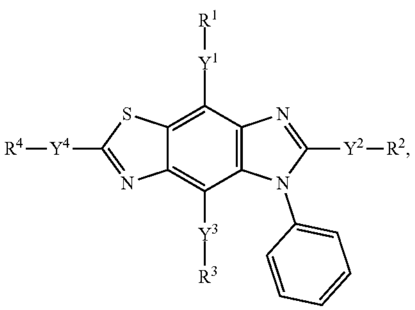

are preferred, wherein $Y^1$, $Y^2$, $Y^3$, $Y^4$, $R^1$, $R^2$, $R^3$ and $R^4$ are as defined above.

Compounds of formula (I), especially compounds of formula (Ia), (Ib), (Ic), (Id), (Ie) and (If) are more preferred, wherein $R^1$, $R^2$, $R^3$ and $R^4$ are independently of each other H, a $C_1$-$C_{25}$alkyl group, a $C_1$-$C_{25}$alkoxy group, a $C_6$-$C_{10}$aryloxy group, a donor group of formula (Xa)

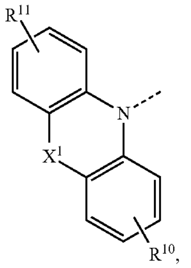

or (Xd)

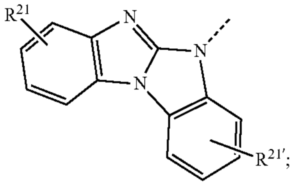

$X^1$ is O, S, C(O), N($R^{15}$), or C($R^{16}$)($R^{17}$); and $R^{10}$, $R^{11}$, $R^{21}$ and $R^{21'}$ are independently of each other H, or a $C_1$-$C_{25}$alkyl group;

$R^{15}$ is a group of formula

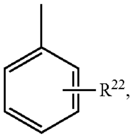

or

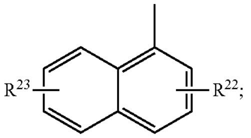

$R^{16}$ and $R^{17}$ are independently of each other H, a $C_1$-$C_{25}$alkyl group;

$R^{22}$ and $R^{23}$ are independently of each other H, a $C_1$-$C_{25}$alkyl group, a $C_1$-$C_{25}$alkoxy group, or a $C_6$-$C_{10}$aryloxy group;

with the proviso that at least one of $R^1$, $R^2$, $R^3$ and $R^4$ is a donor group of formula (Xa) or (Xd).

$Y^1$, $Y^2$, $Y^3$ and $Y^4$ are preferably a direct bond, or a group of formula —[$A^1$]-, wherein $A^1$ is a $C_6$-$C_{10}$arylene group which may optionally be substituted by one, or more $C_1$-$C_{25}$alkyl groups. Examples of $C_6$-$C_{10}$arylene groups are phenylene and naphthylene. Preferred $C_6$-$C_{10}$arylene groups are 1,3-phenylene and 3,6-naphthylene, which may optionally be substituted by one or more $C_1$-$C_8$alkyl groups. $Y^1$, $Y^2$, $Y^3$ and $Y^4$ are more preferably a direct bond, or a group of formula

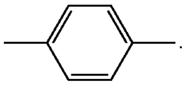

The donor group is preferably a donor group of formula (Xa), wherein $X^1$ is O, S, $C(CH_3)(CH_3)$, C(=O),

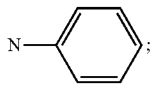

or a donor group of formula (Xd), wherein $R^{21}$ and $R^{21'}$ are H.

The donor group is more preferably a group of formula

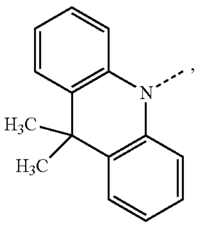
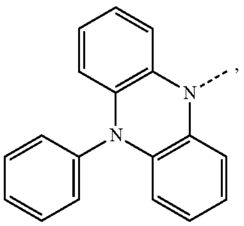
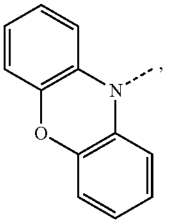
or
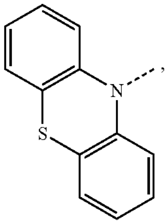
or
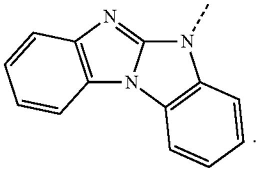

In a particularly preferred embodiment the present invention the compound of formula (I) is a compound of formula (Ia), (Ib), (Ic), (Id), (Ie) and (If), especially a compound of formula (Ia), (Ib) and (Ic), wherein $Y^1$ and $Y^3$ are a direct bond;

$R^1$ and $R^3$ are H;

$Y^2$ and $Y^4$ are a direct bond, or a group of formula

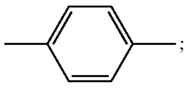

$R^2$ and $R^4$ are independently of each other a donor group of formula (Xa), or (Xd); or a compound of formula (Ia), (Ib), (Ic), (Id), (Ie) and (If), especially a compound of formula (Ia), (Ib) and (Ic), wherein $Y^2$ and $Y^4$ are a direct bond;

$R^2$ and $R^4$ are H;

$Y^1$ and $Y^3$ are a direct bond, or a group of formula

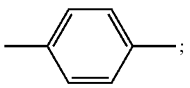

$R^1$ and $R^3$ are independently of each other a donor group of formula (Xa), or (Xd); or a compound of formula (Ia), (Ib), (Ic), (Id), (Ie) and (If), especially a compound of formula (Ia), (Ib) and (Ic), wherein $Y^4$ is a direct bond, or a group of formula

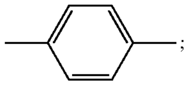

$R^4$ is a donor group of formula (Xa), or (Xd);

$Y^2$ is a group of formula

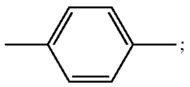

$R^2$ is H;

$Y^1$ and $Y^3$ are a direct bond;

$R^1$ and $R^3$ are H; or a compound of formula (Ia), (Ib), (Ic), (Id), (Ie) and (If), especially a compound of formula (Ia), (Ib) and (Ic), wherein $Y^1$ is a direct bond, or a group of formula

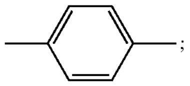

$R^1$ is a donor group of formula (Xa), or (Xd);

$Y^2$, $Y^3$ and $Y^4$ are a group of formula

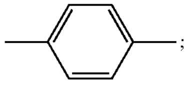

$R^2$, $R^3$ and $R^4$ are H, wherein the donor group (Xa) is a group of formula

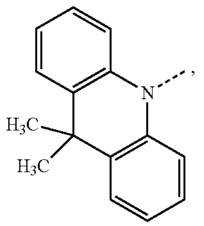
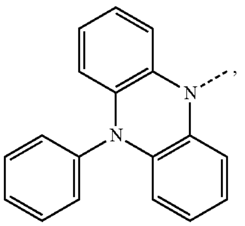
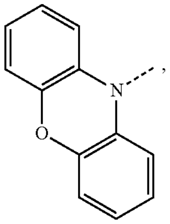
or
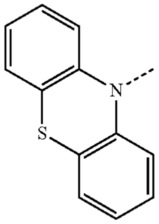

and the donor group (Xd) is a group of formula
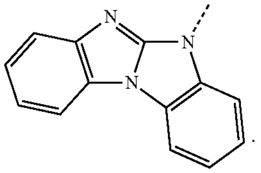
Among compounds of formula (Ia), (Ib), (Ic), (Id), (Ie) and (If) compounds of formula (Ia), (Ib) and (Ic) are more preferred.
Examples of compounds of formula
(Ia)
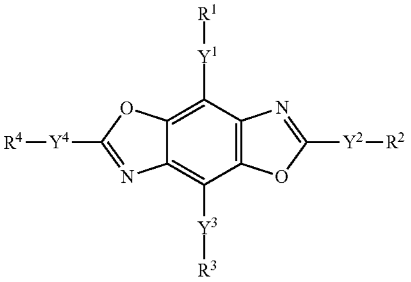
are shown below:
(A-1)
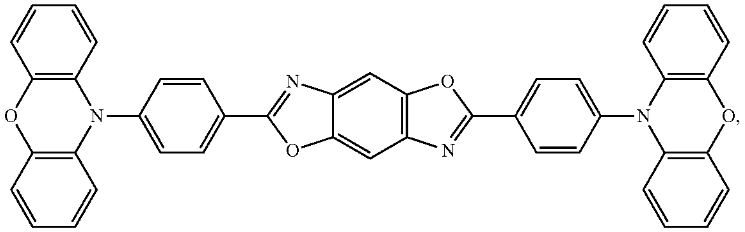
(A-2)
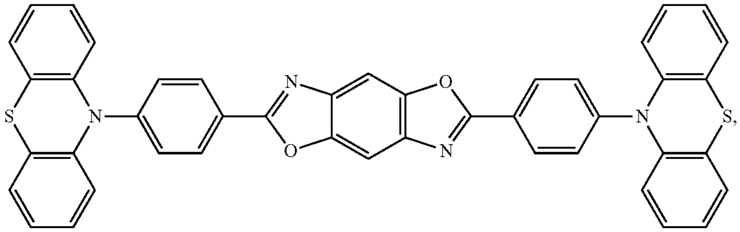
(A-3)
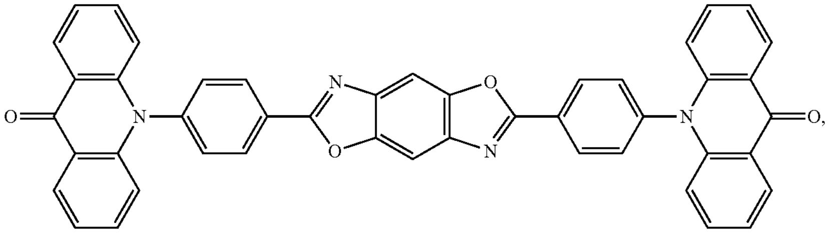

-continued
(A-4)
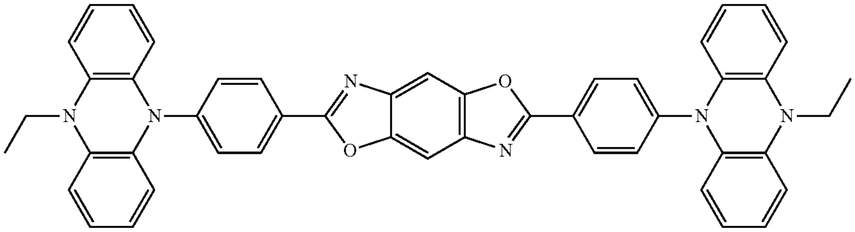
,
(A-5)
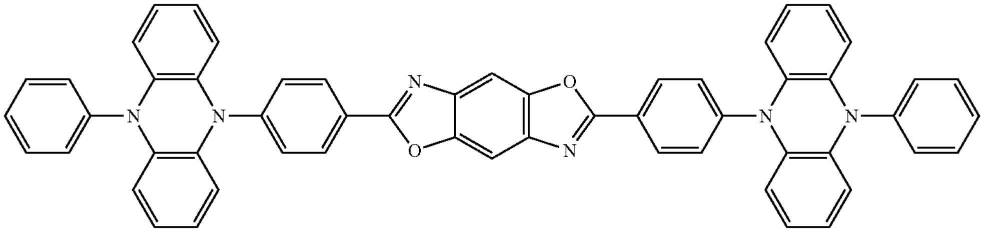
,
(A-6)
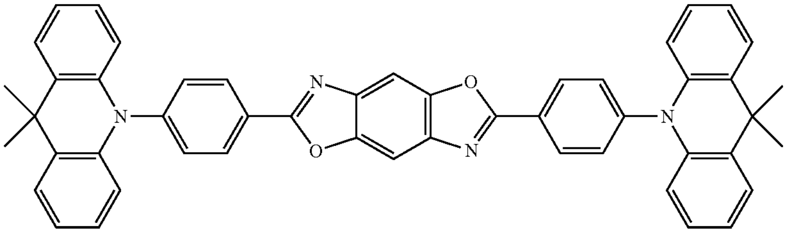
,
(A-7)
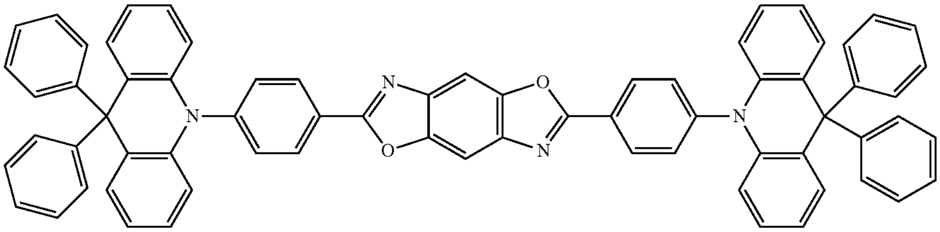
,
(A-8)
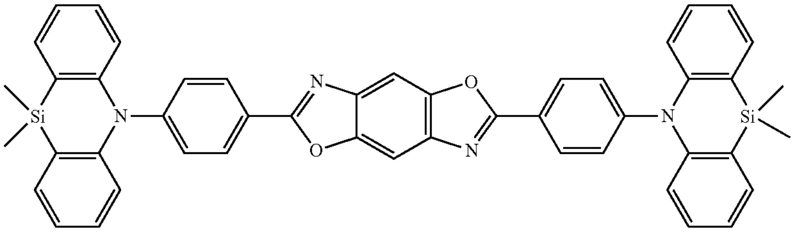
,
(A-9)
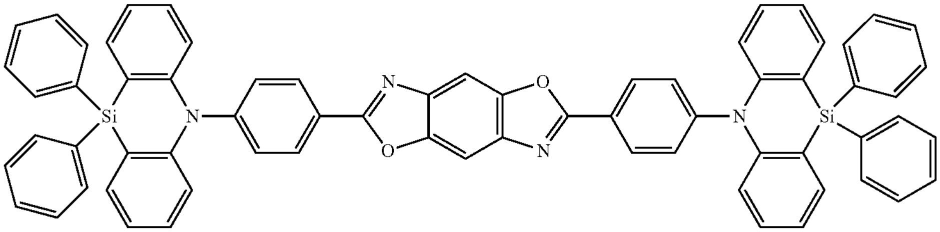
, -continued
(A-10)
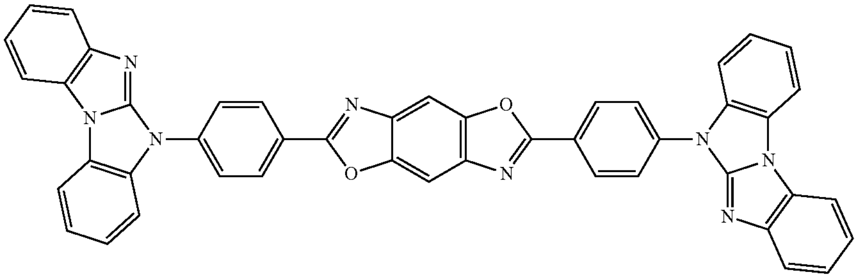
(A-11)
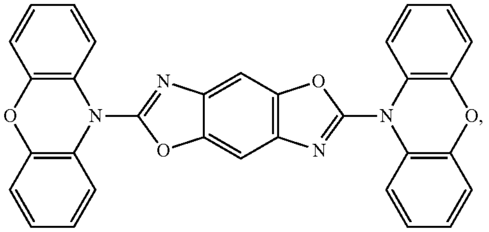
(A-12)
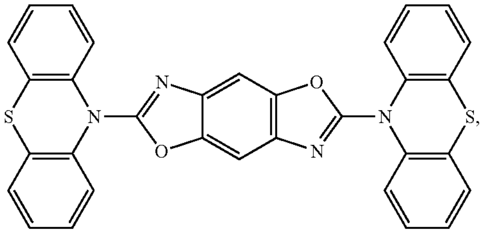
(A-13)
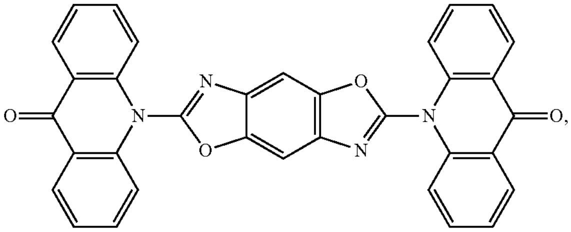
(A-14)
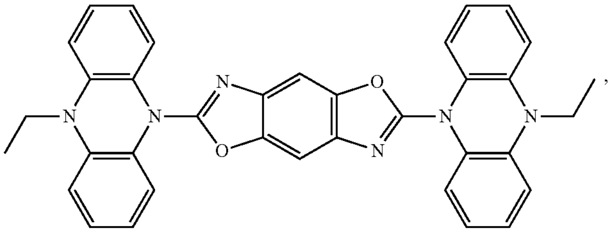
(A-15)
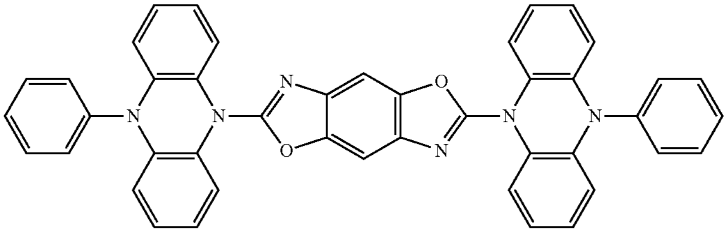
, -continued
(A-16)
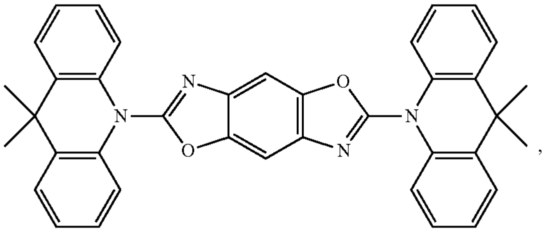
(A-17)
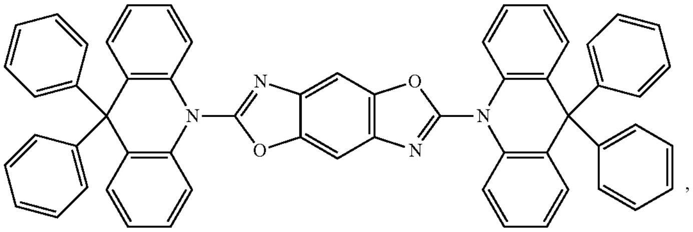
(A-18)
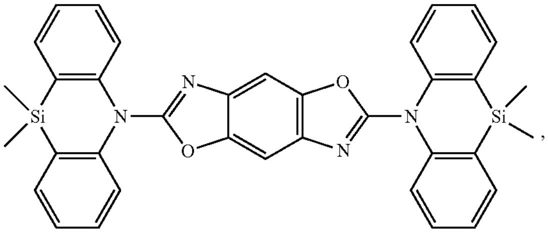
(A-19)
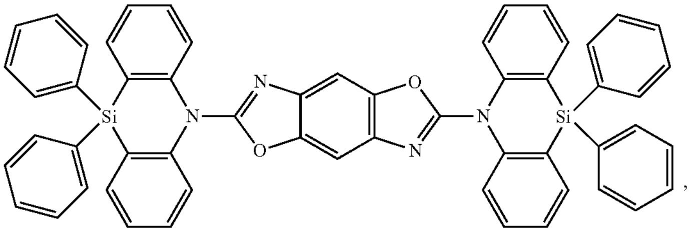
(A-20)
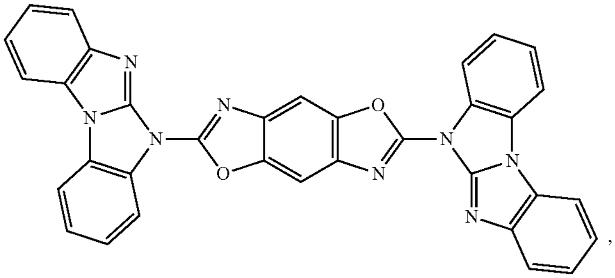

-continued
(A-21)
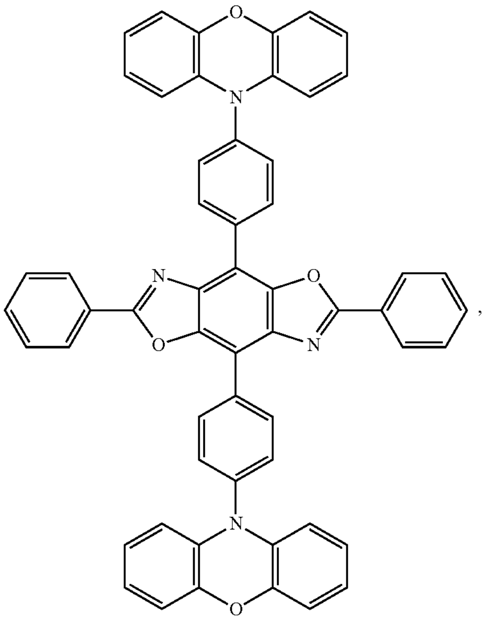
,
(A-22)
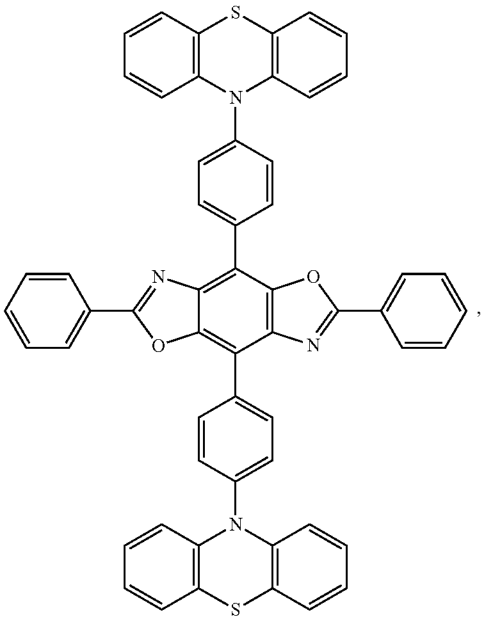
,

-continued
(A-23)
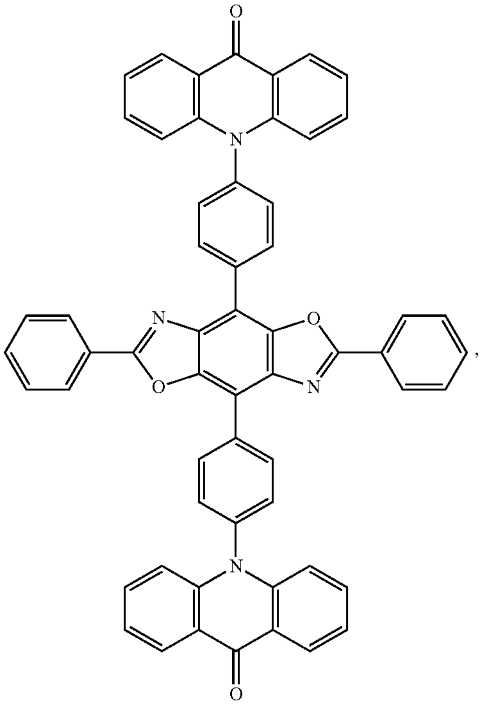
,
(A-24)
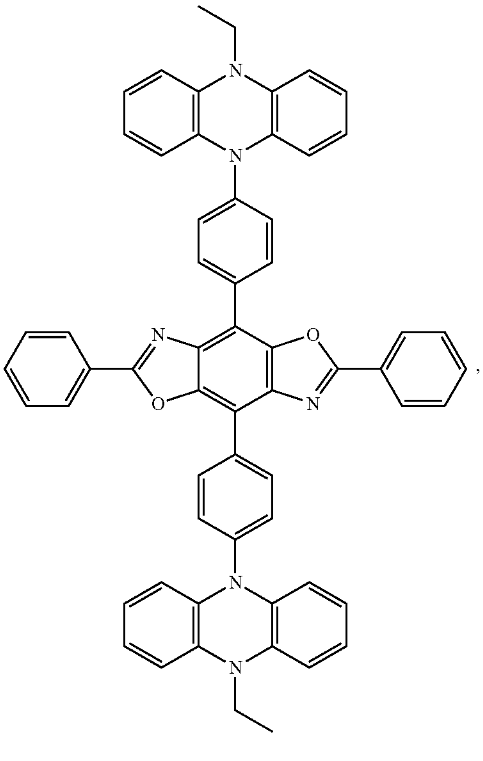
,

-continued
(A-25)
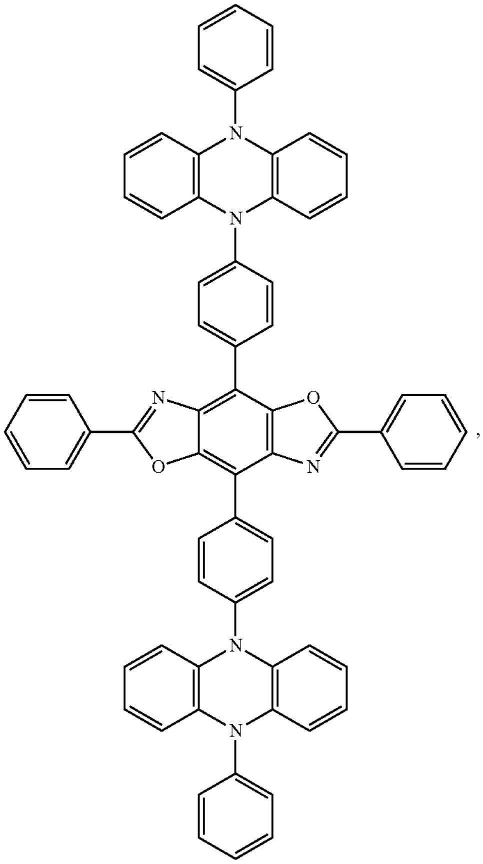
,
(A-26)
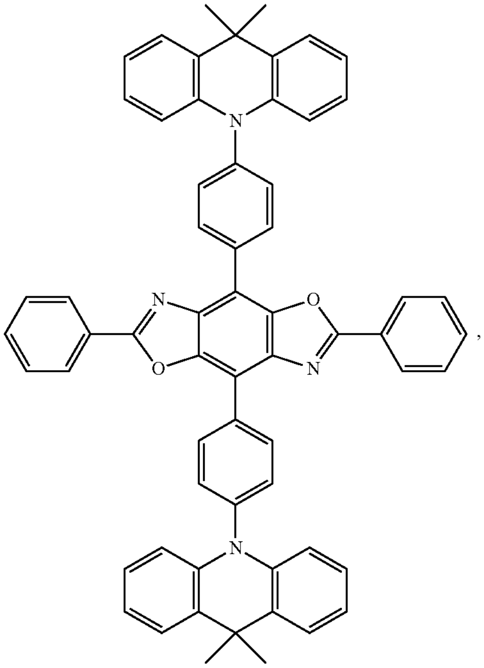
,

-continued
(A-27)
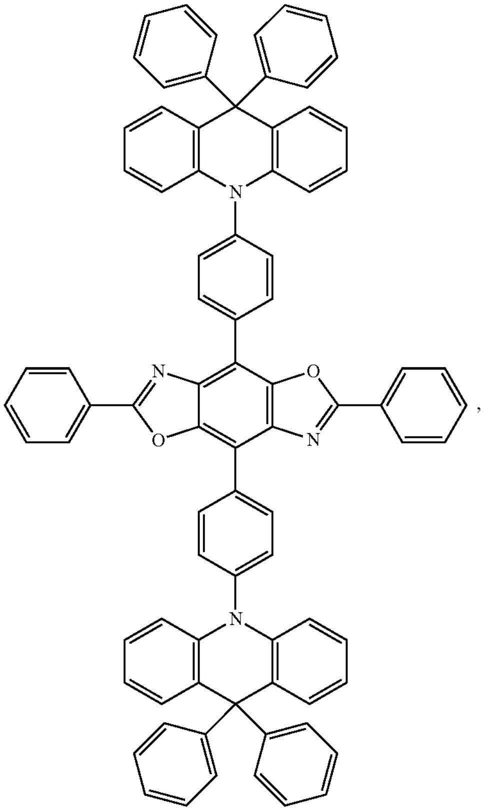
,
(A-28)
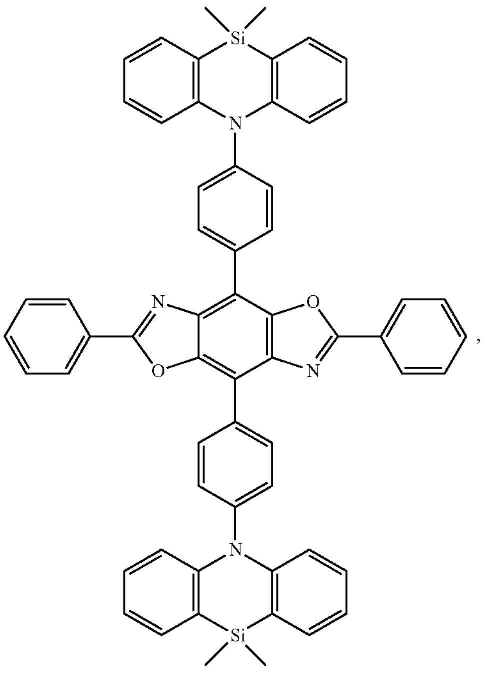
,

-continued
(A-29)
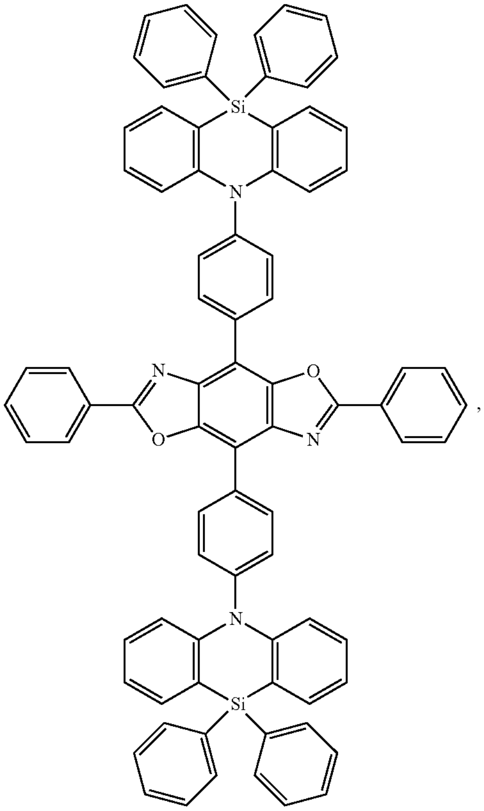
,
(A-30)
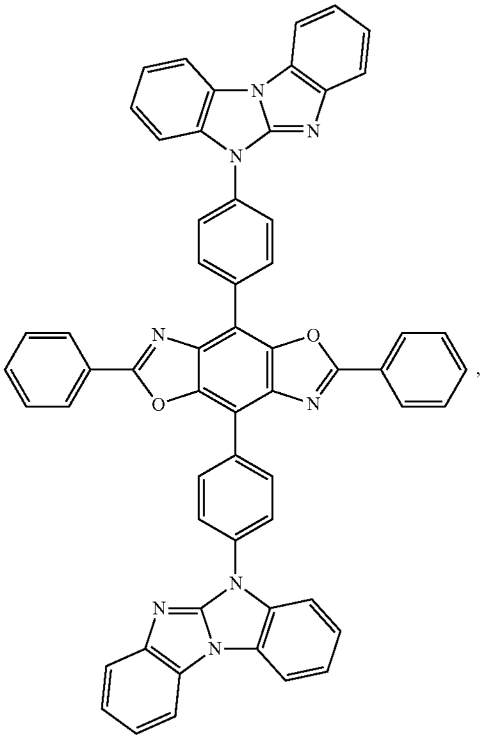
,

-continued
(A-31)
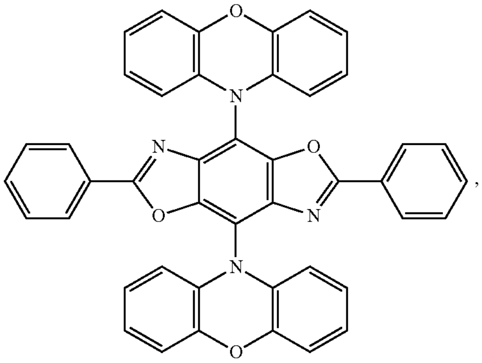
,
(A-32)
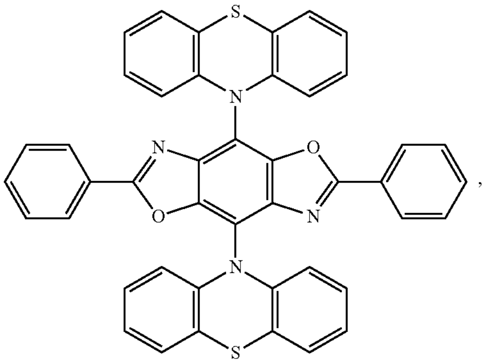
,
(A-33)
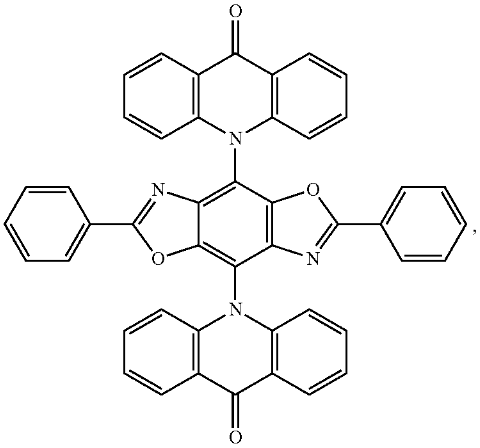
,

-continued
(A-34)
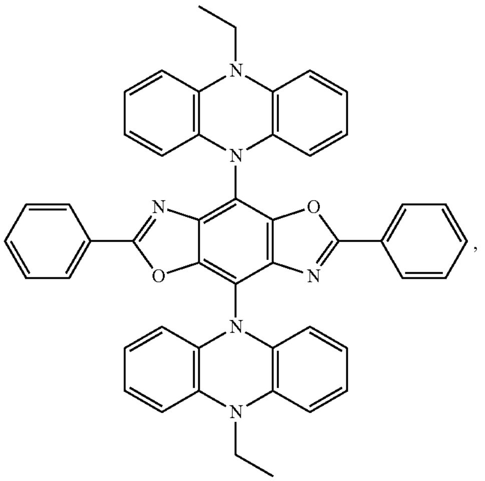
(A-35)
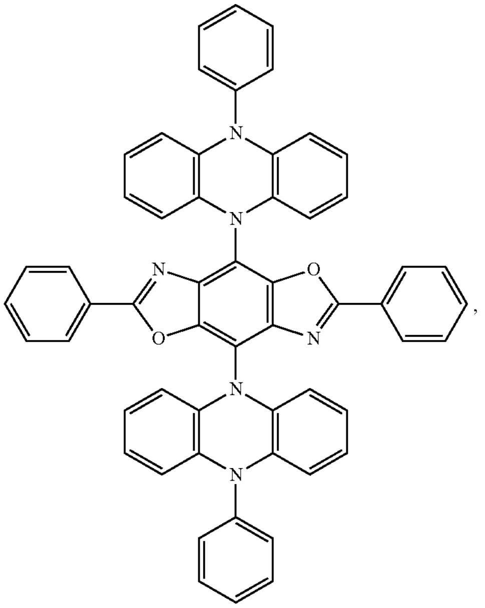
(A-36)
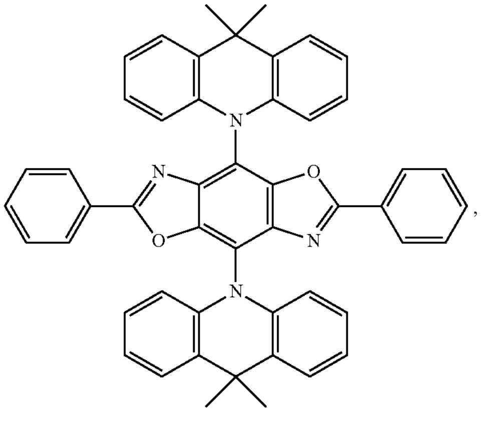

-continued
(A-37)
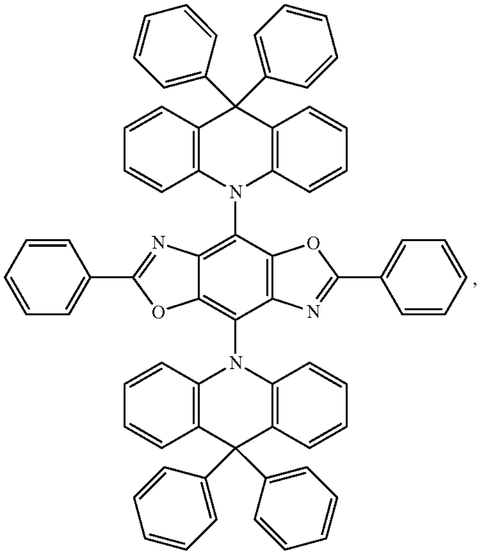
,
(A-38)
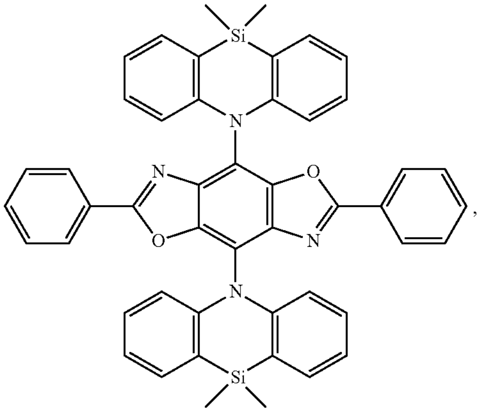
,
(A-39)
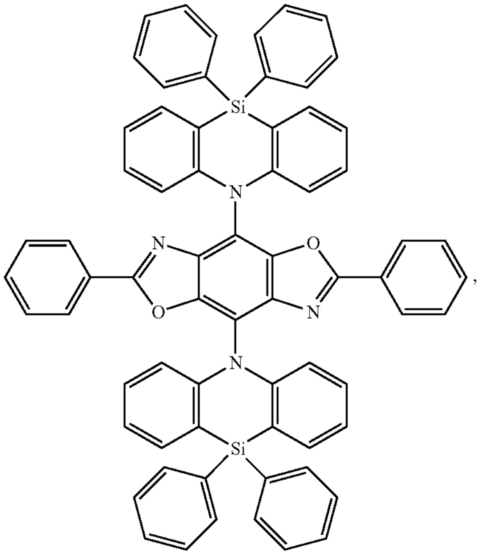
,

-continued
(A-40)
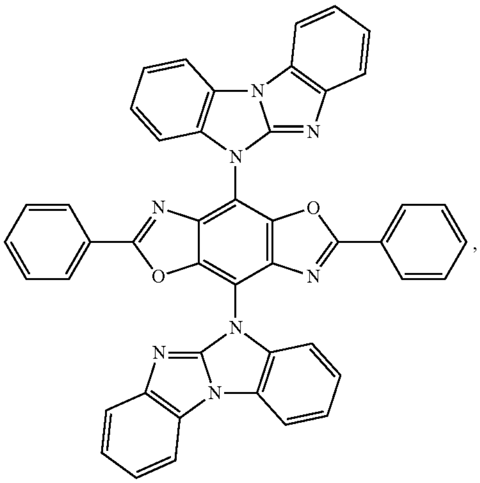
,
(A-41)
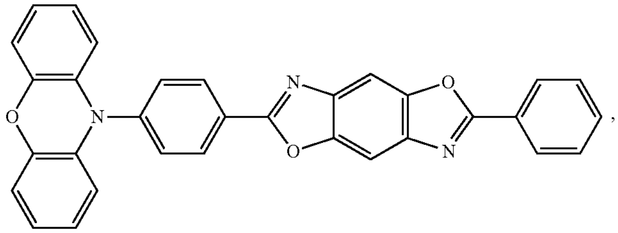
,
(A-42)
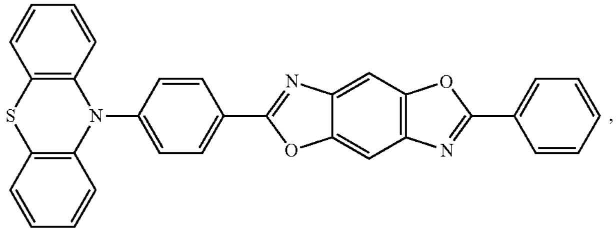
,
(A-43)
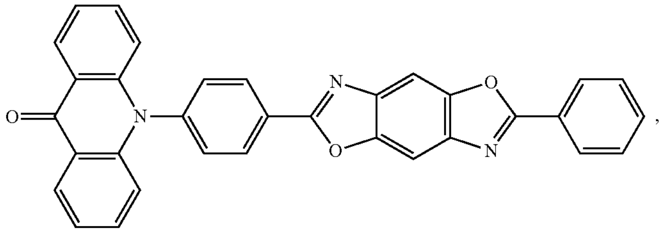
,
(A-44)
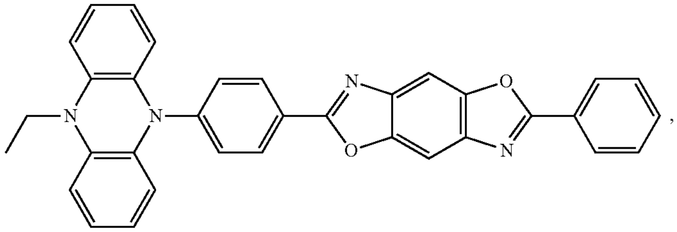
, -continued
(A-45)
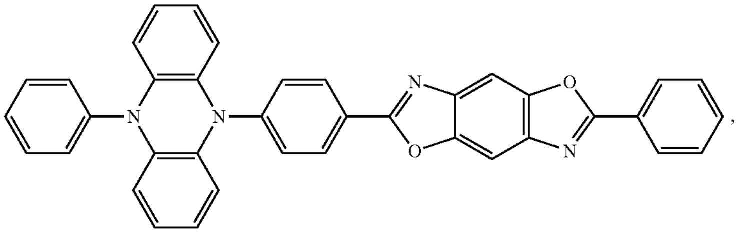
(A-46)
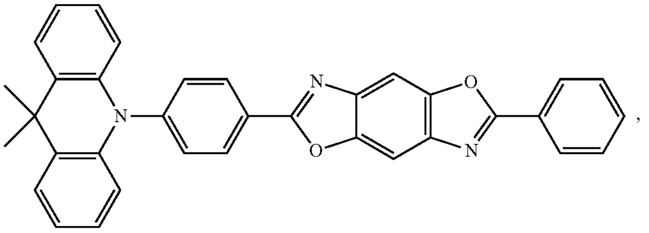
(A-47)
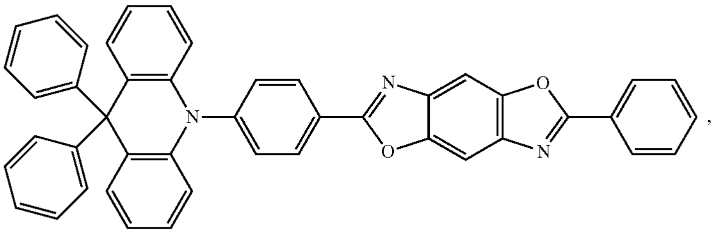
(A-48)
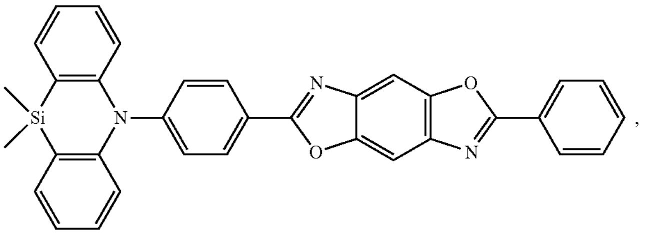
(A-49)
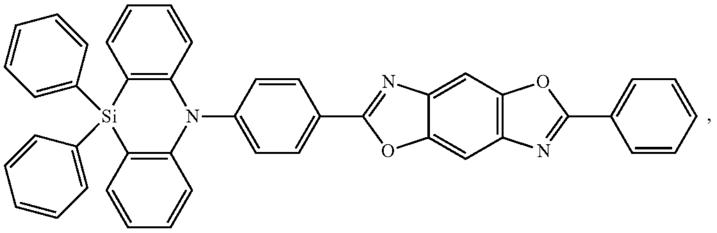
(A-50)
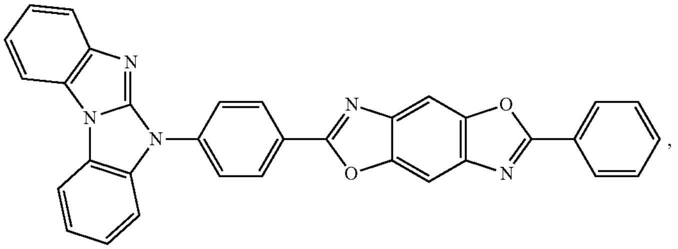

-continued
(A-51)
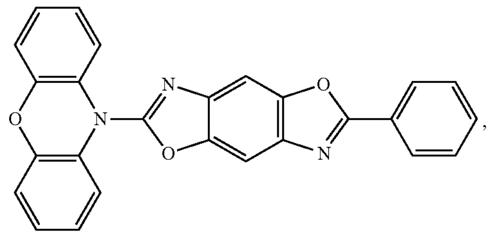
(A-52)
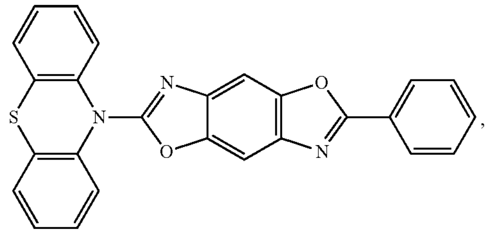
(A-53)
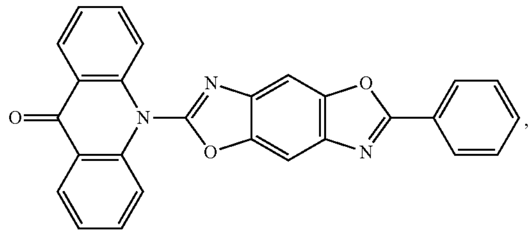
(A-54)
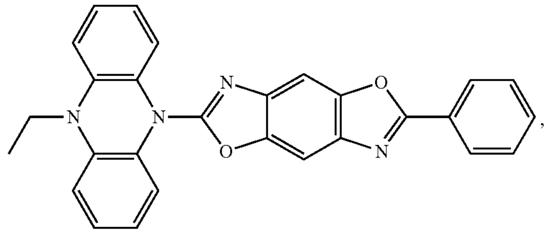
(A-55)
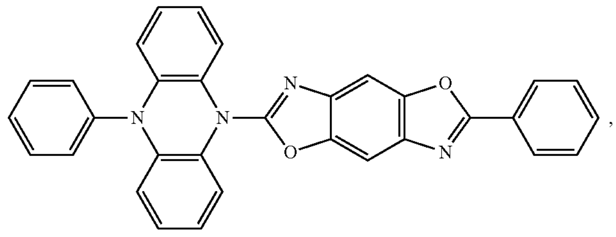
(A-56)
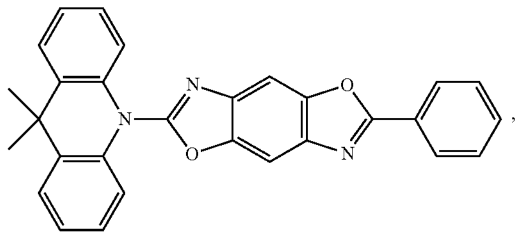

-continued
(A-57)
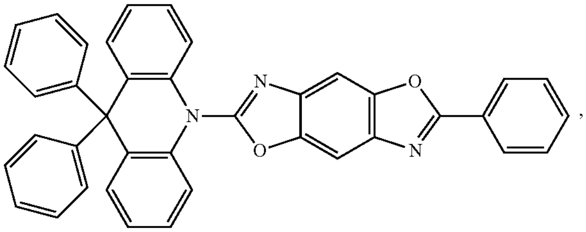
,
(A-58)
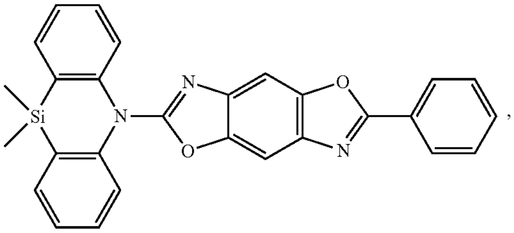
,
(A-59)
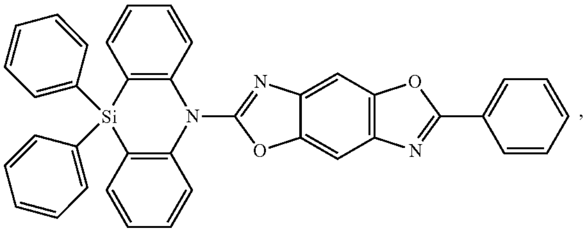
,
(A-60)
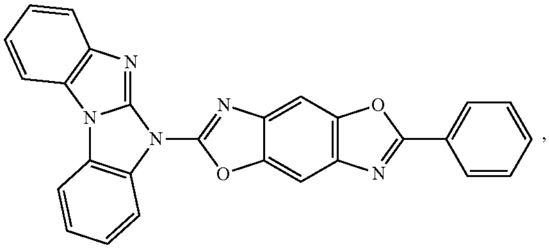
,
(A-61)
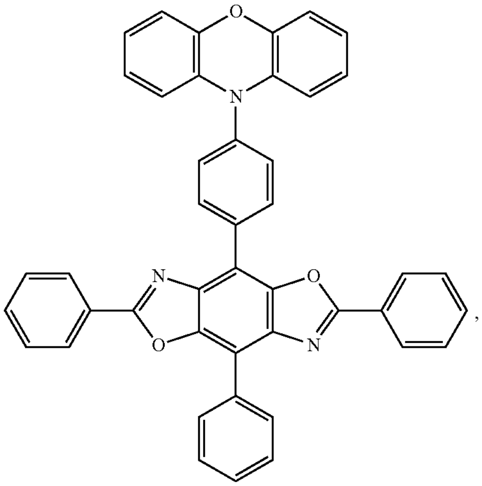
, -continued
(A-62)
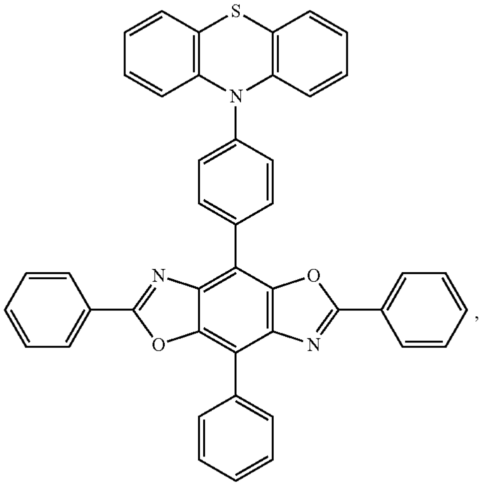
(A-63)
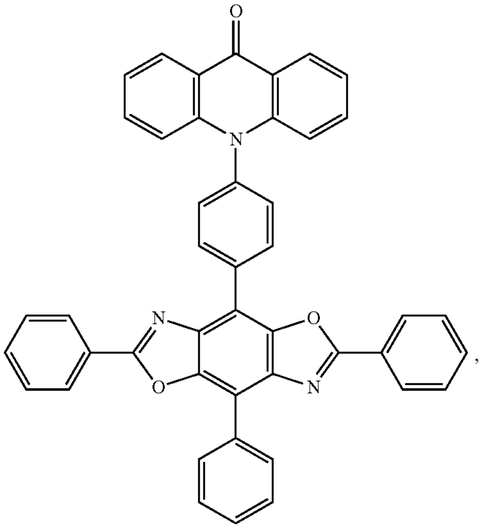
(A-64)
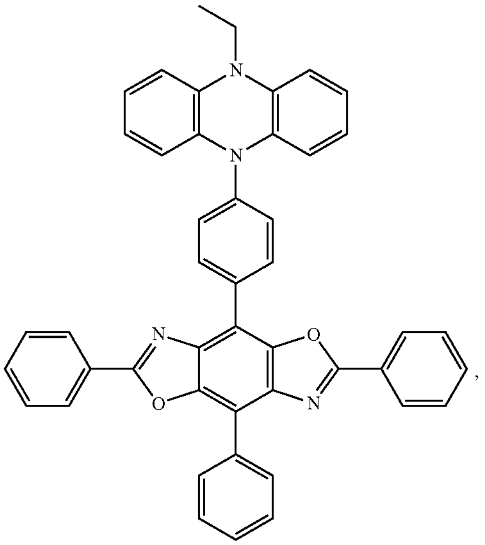

-continued
(A-65)
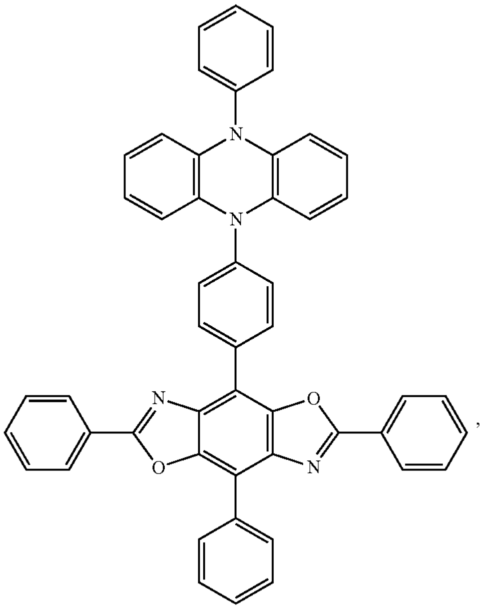
,
(A-66)
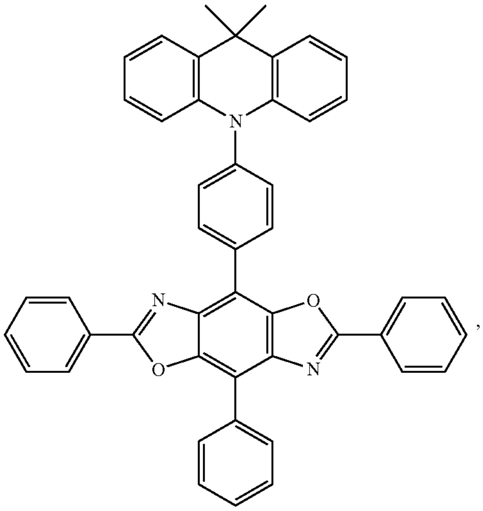
,

-continued
(A-67)
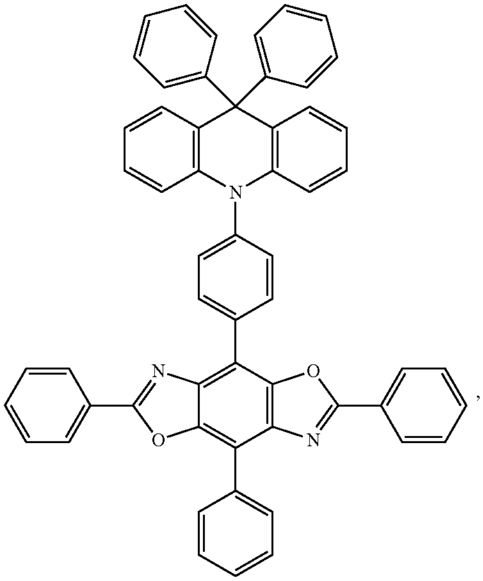
,
(A-68)
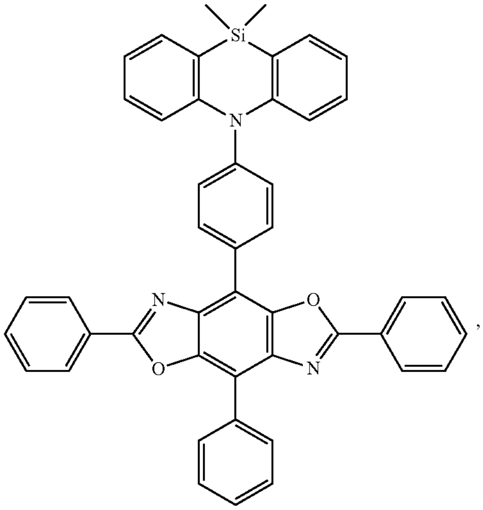
,

-continued
(A-69)
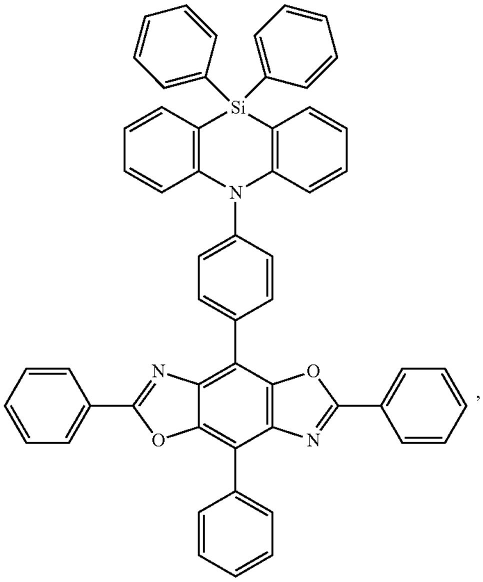
,
(A-70)
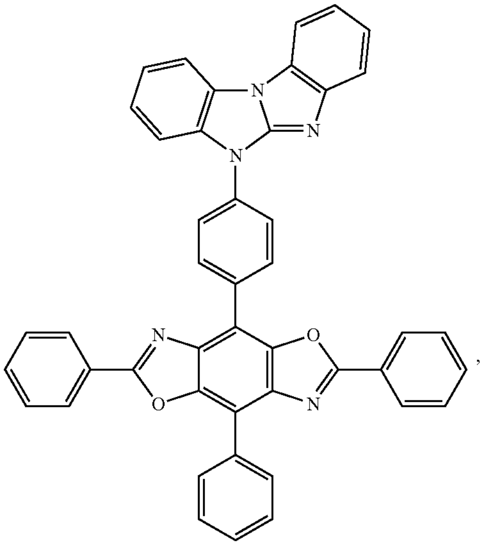
,
(A-71)
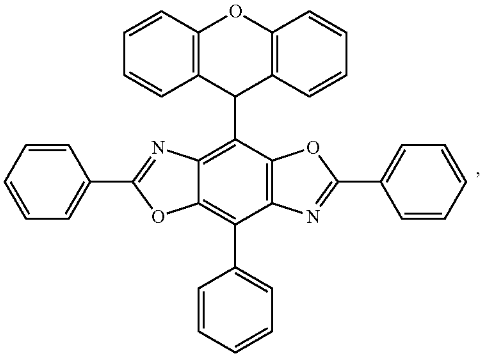
,

-continued
(A-72)
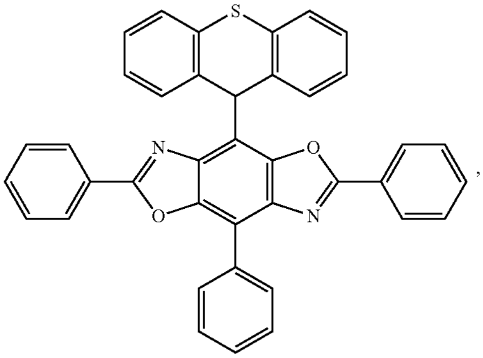
,
(A-73)
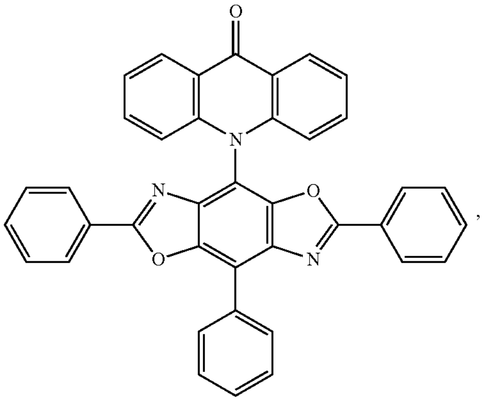
,
(A-74)
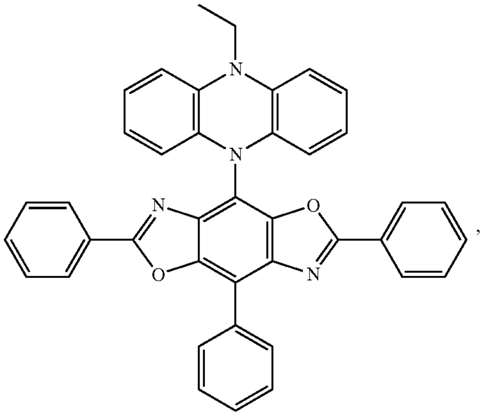
,

-continued
(A-75)
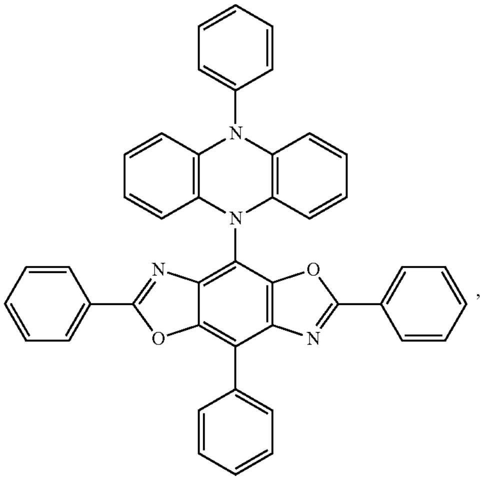
,
(A-76)
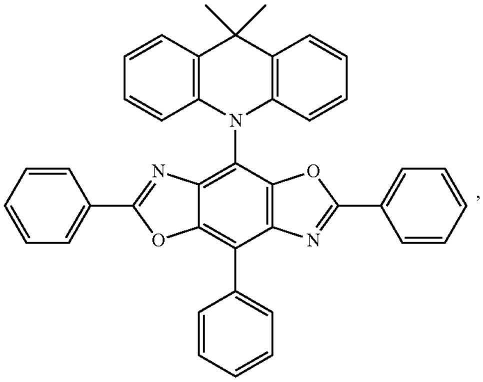
,
(A-77)
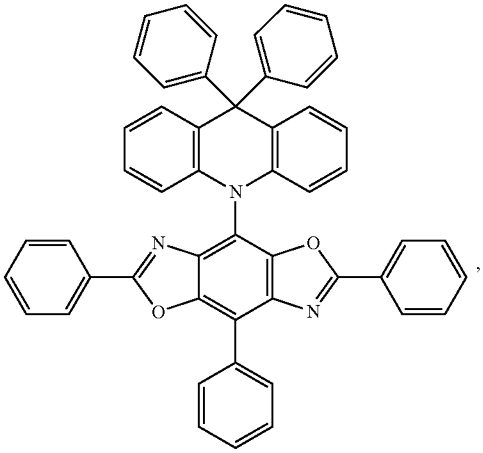
,

-continued
(A-78)
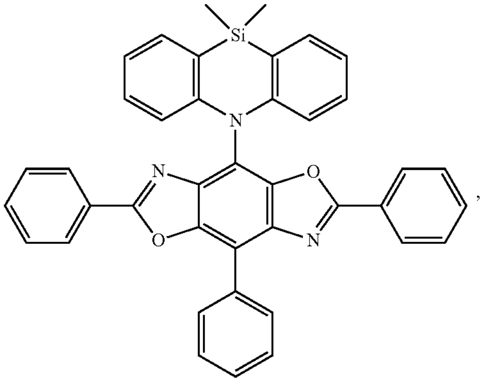
,
(A-79)
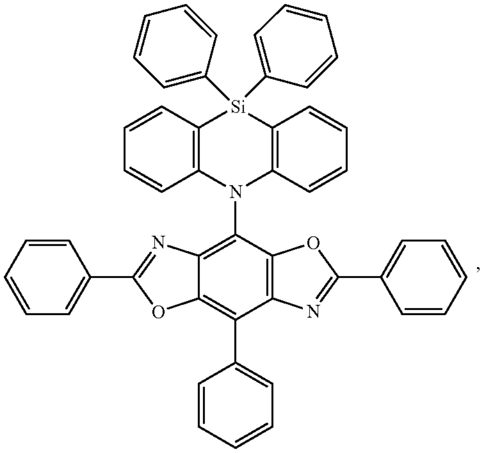
,
(A-80)
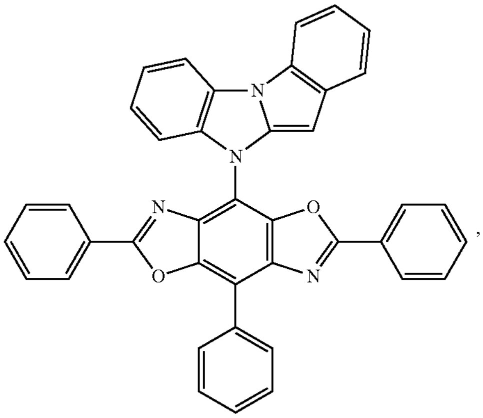
,
(A-81)
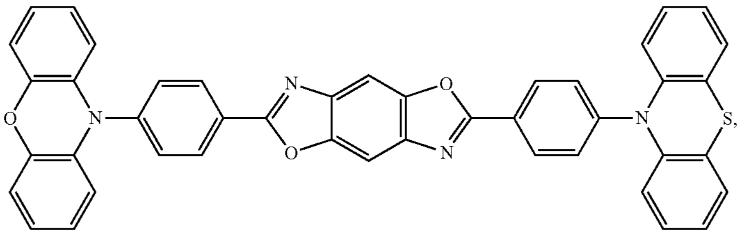
, -continued
(A-82)
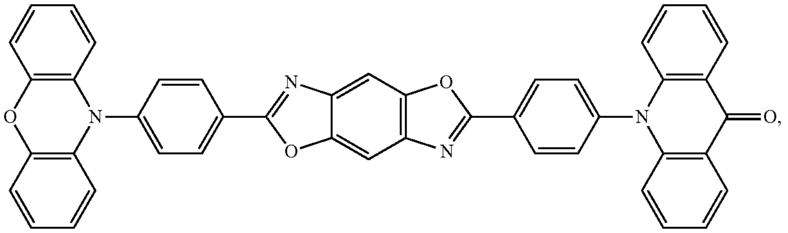
(A-83)
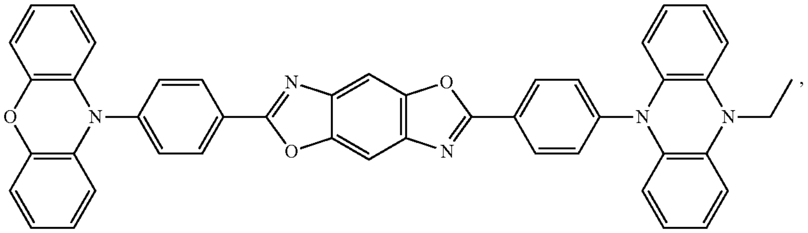
(A-84)
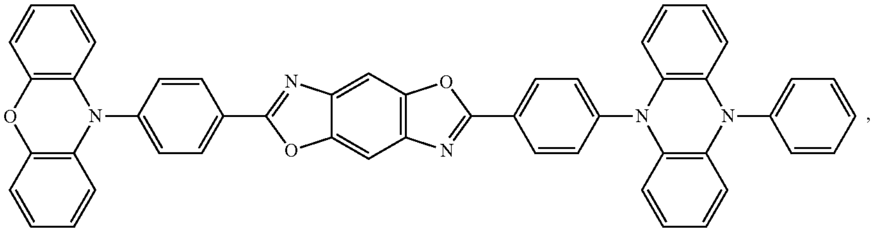
(A-85)
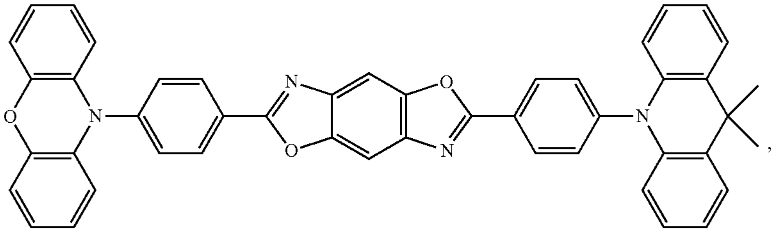
(A-86)
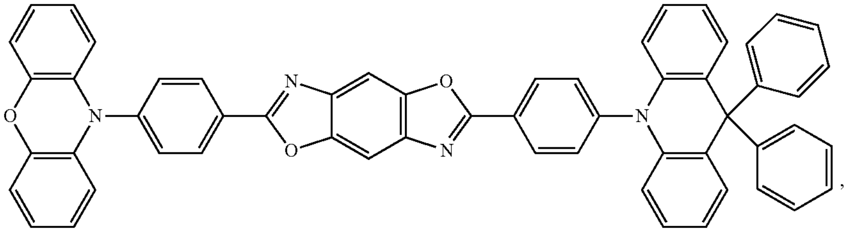
(A-87)
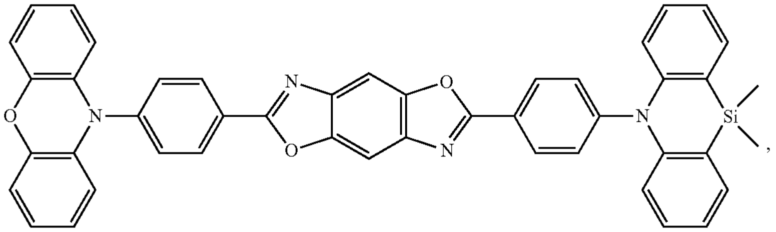

-continued
(A-88)
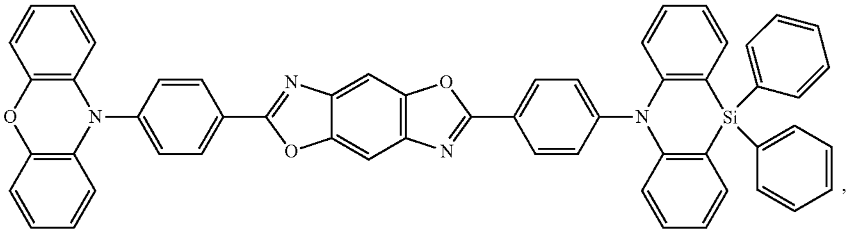
,
(A-89)
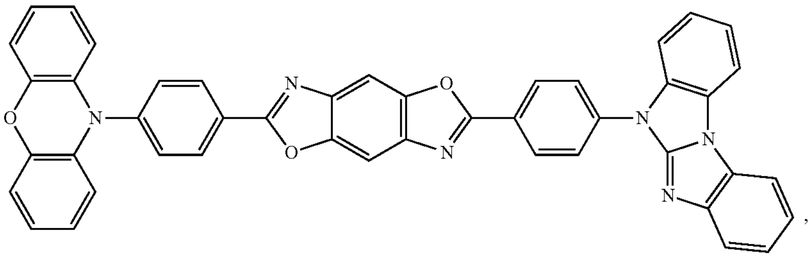
,
(A-90)
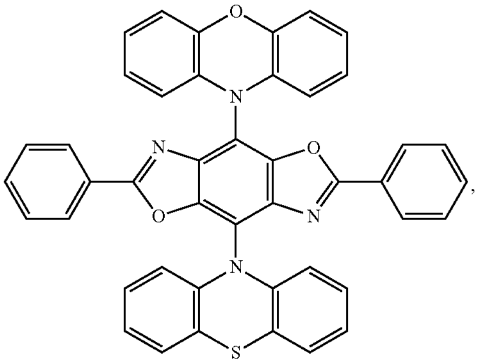
,
(A-91)
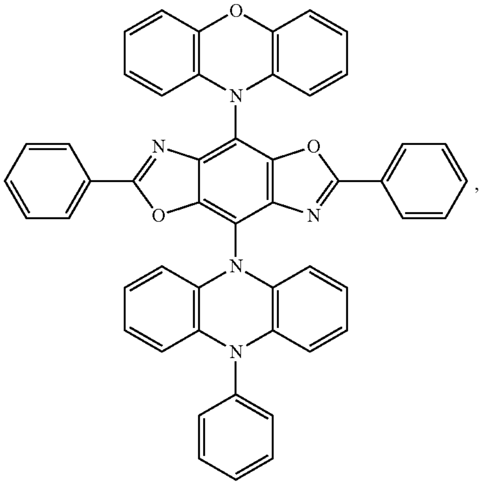
, -continued
(A-92)
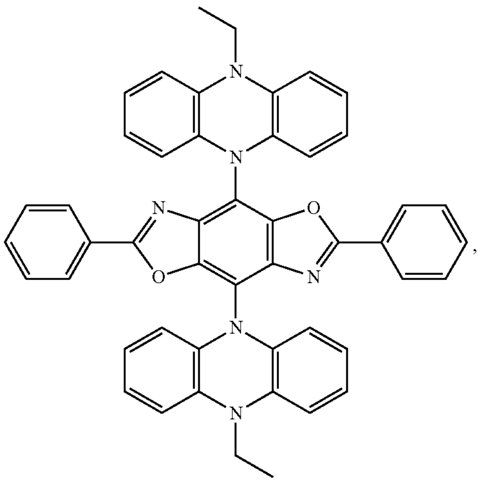
,
(A-93)
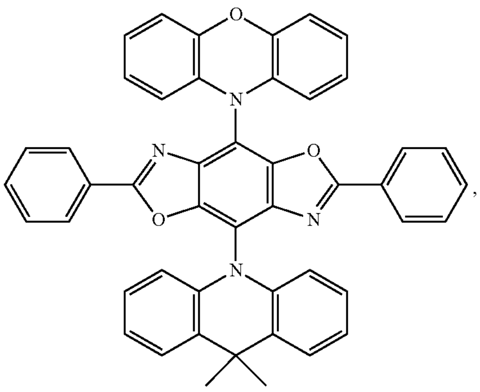
,
(A-94)
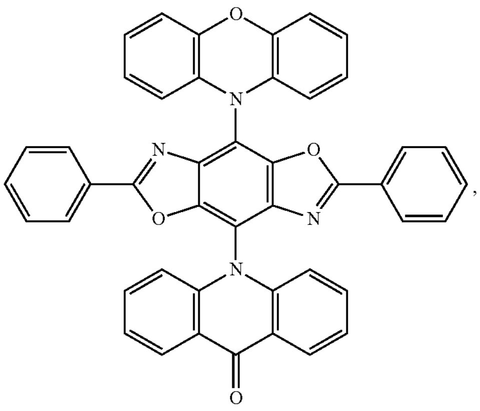
, -continued
(A-95)
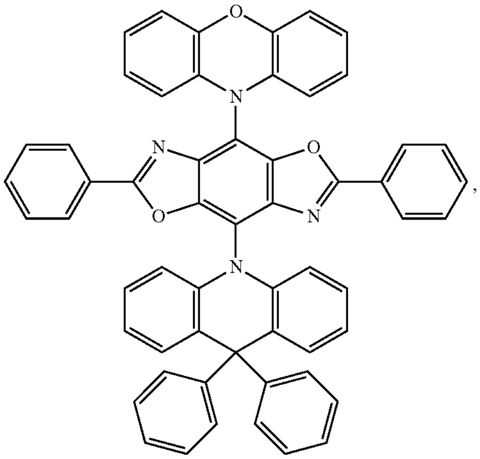
(A-96)
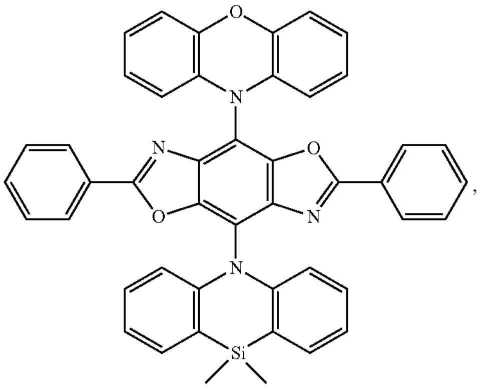
(A-97)
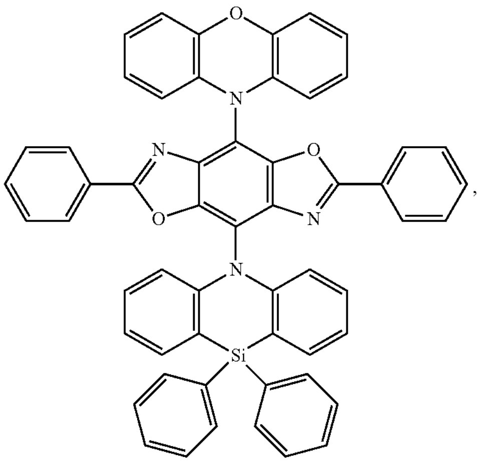
, -continued
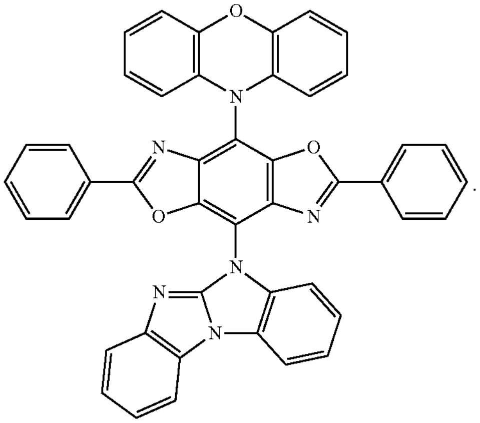
(A-98)
Among compounds of formula (Ia) those are preferred which are substituted by donor groups of formula
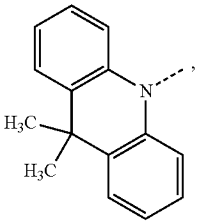
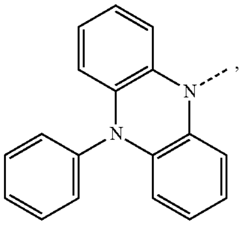
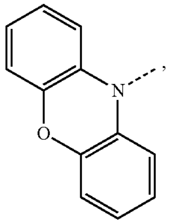
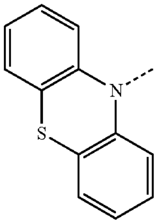
and
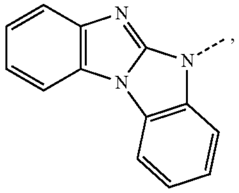
such as, for example, compounds (A-1), (A-2), (A-5), (A-6), (A-10), (A-11), (A-12), (A-15), (A-16), (A-20), (A-21), (A-22), (A-25), (A-26), (A-30), (A-31), (A-32), (A-35), (A-36), (A-40), (A-41), (A-42), (A-45), (A-46), (A-50), (A-51), (A-52), (A-55), (A-56), (A-60), (A-61), (A-62), (A-65), (A-66), (A-70), (A-71), (A-72), (A-75), (A-76), (A-80), (A-81), (A-84), (A-85), (A-89), (A-90), (A-91), (A-93), and (A-98).
The most preferred compounds are compounds (A-1), (A-2), (A-5), (A-6), (A-10), (A-31), (A-32), (A-35), (A-36), (A-41), (A-42), (A-45), (A-46) and (A-50).
Examples of compounds of formula
(Ib)
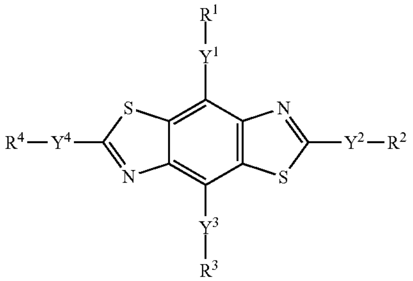
are compounds
(B-1)
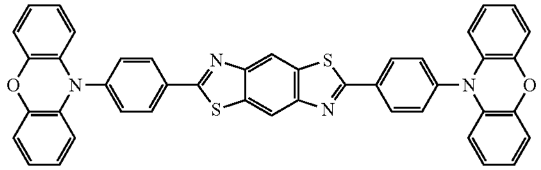
to
(B-98)
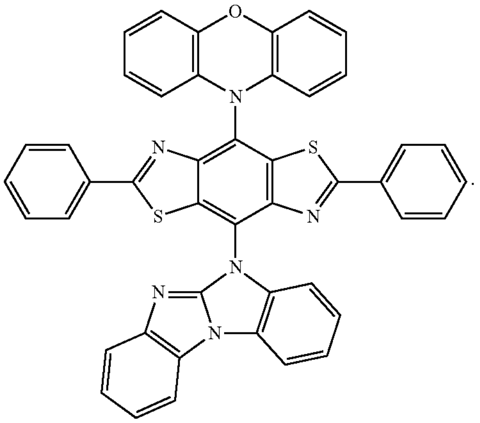

Compounds (B-1) to (B-98) correspond in structure to compounds (A-1) to (A-98), except that 0 in the core structure of compounds (A-1) to (A-98) is replaced by S.

Among compounds of formula (Ib) those are preferred which are substituted by donor groups of formula

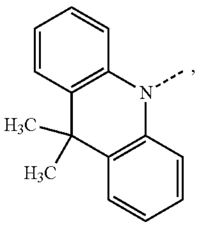

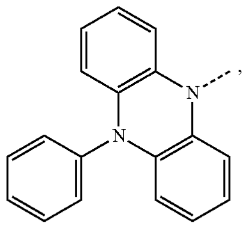

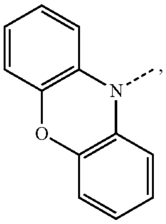

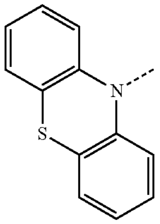

and

-continued

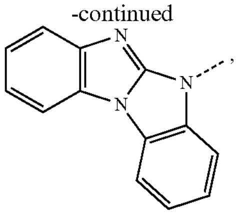

such as, for example, compounds (B-1), (B-2), (B-5), (B-6), (B-10), (B-11), (B-12), (B-15), (B-16), (B-20), (B-21), (B-22), (B-25), (B-26), (B-30), (B-31), (B-32), (B-35), (B-36), (B-40), (B-41), (B-42), (B-45), (B-46), (B-50), (B-51), (B-52), (B-55), (B-56), (B-60), (B-61), (B-62), (B-65), (B-66), (B-70), (B-71), (B-72), (B-75), (B-76), (B-80), (B-81), (B-84), (B-85), (B-89), (B-90), (B-91), (B-93), and (B-98).

The most preferred compounds are (B-1)

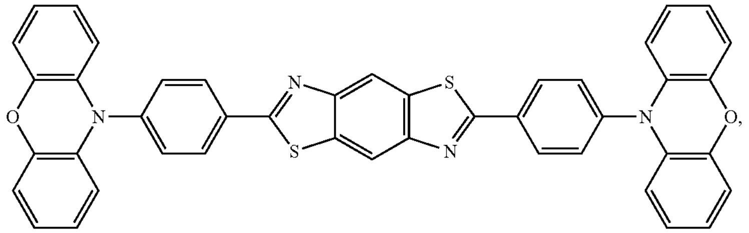

(B-2)

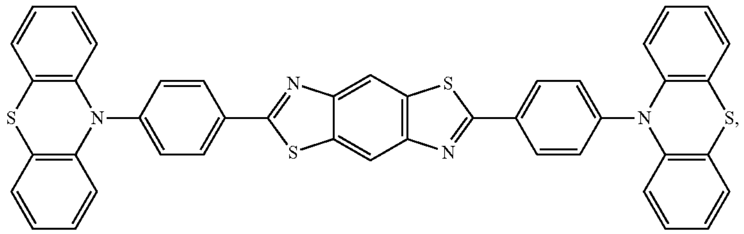

(B-5)

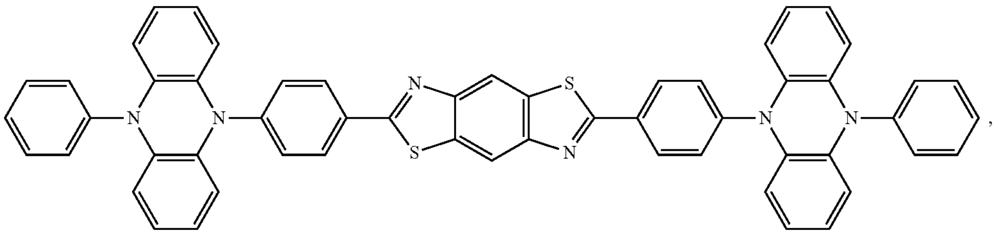

-continued
(B-6)
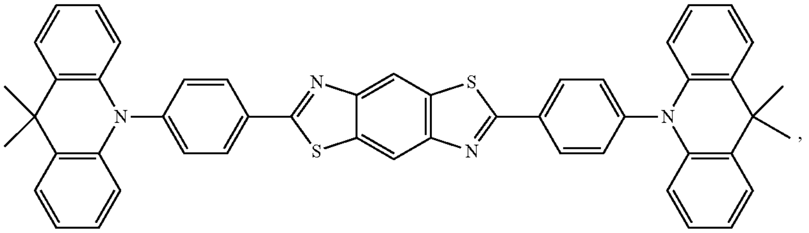
(B-10)
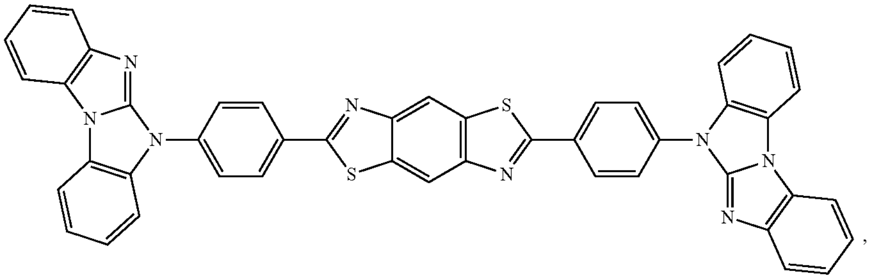
(B-31)
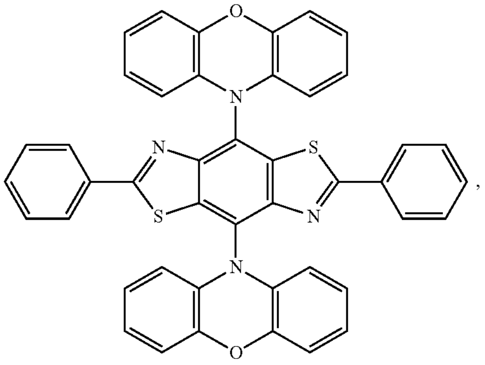
(B-32)
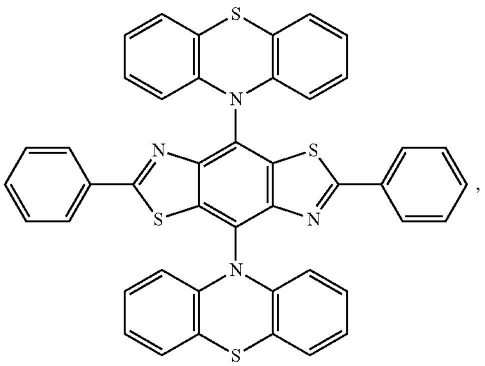

-continued
(B-35)
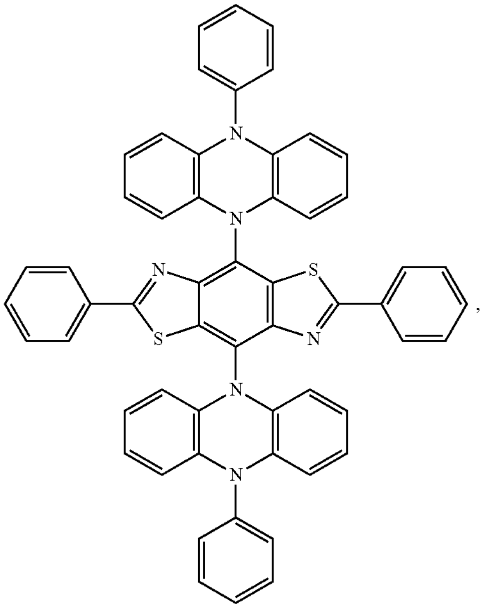
,
(B-36)
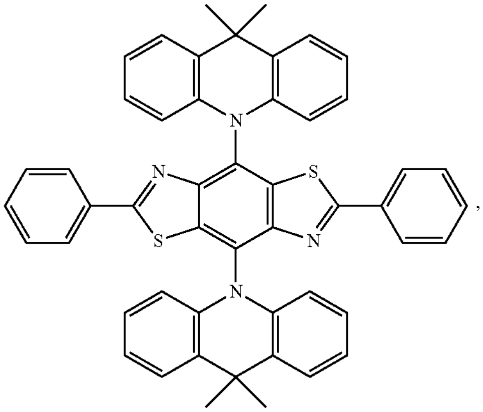
,
(B-41)
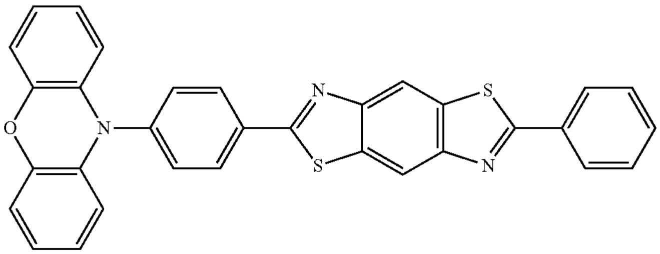
,
(B-42)
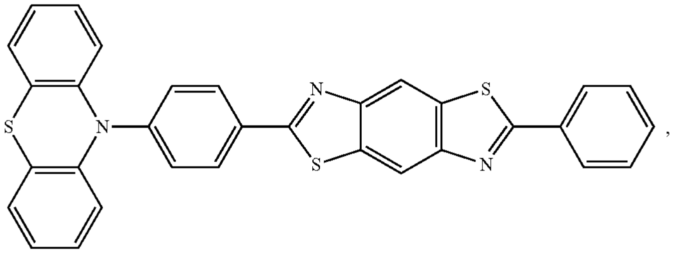
, -continued
(B-45)
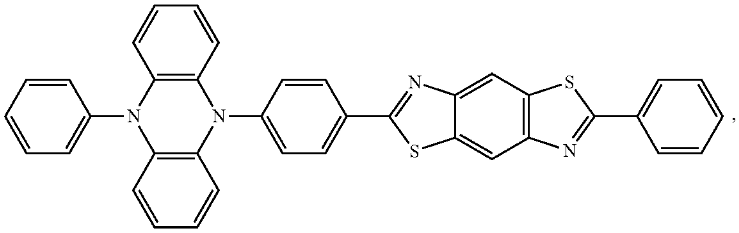
,
(B-46)
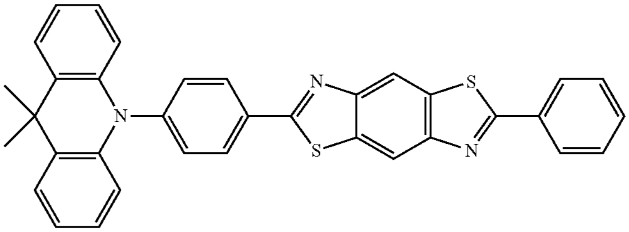
and
(B-50)
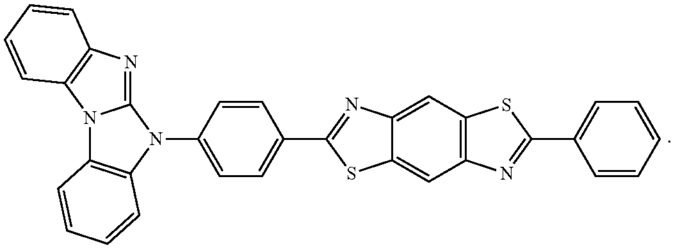
.
Examples of compounds of formula
(Ic)
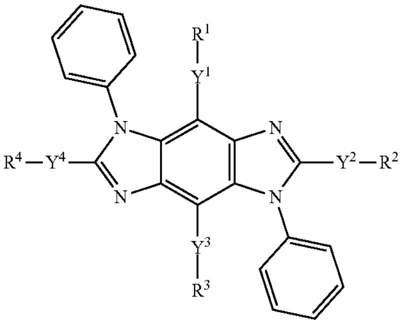
are compounds
(C-1)
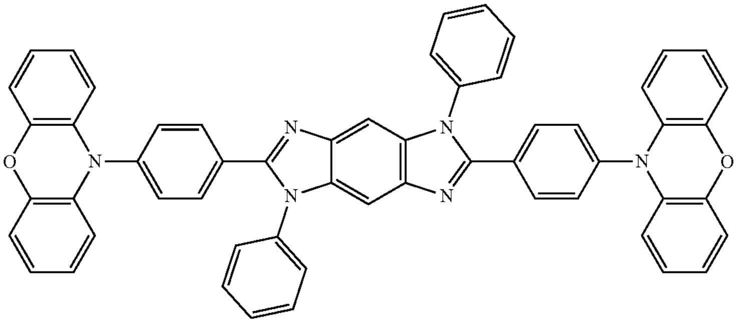
to -continued (C-98)

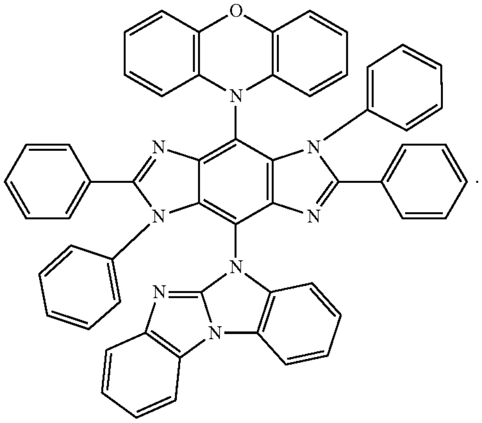

Compounds (C-1) to (C-98) correspond in structure to compounds (A-1) to (A-98), except that O in the core structure of compounds (A-1) to (A-98) is replaced by N-phenyl.

Among compounds of formula (Ic) those are preferred which are substituted by donor groups of formula

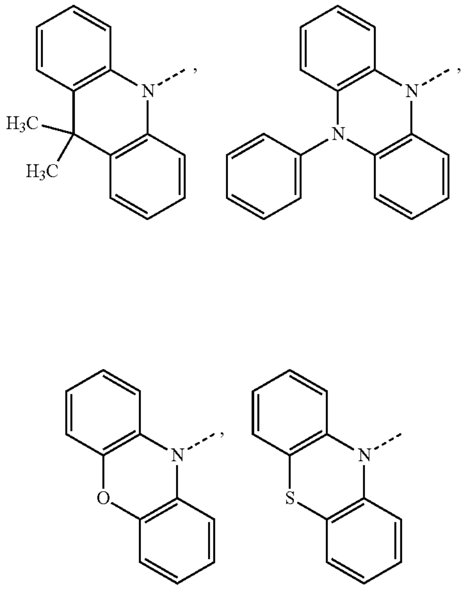

-continued

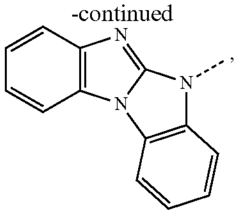

and such as, for example, compounds (C-1), (C-2), (C-5), (C-6), (C-10), (C-11), (C-12), (C-15), (C-16), (C-20), (C-21), (C-22), (C-25), (C-26), (C-30), (C-31), (C-32), (C-35), (C-36), (C-40), (C-41), (C-42), (C-45), (C-46), (C-50), (C-51), (C-52), (C-55), (C-56), (C-60), (C-61), (C-62), (C-65), (C-66), (C-70), (C-71), (C-72), (C-75), (C-76), (C-80), (C-81), (C-84), (C-85), (C-89), (C-90), (C-91), (C-93), and (C-98).

The most preferred compounds are compounds (C-1)

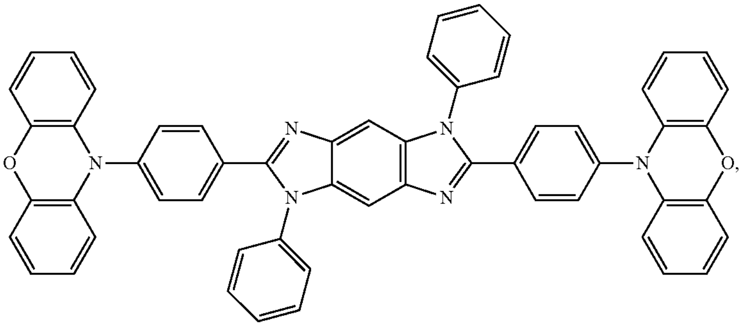

-continued
(C-2)
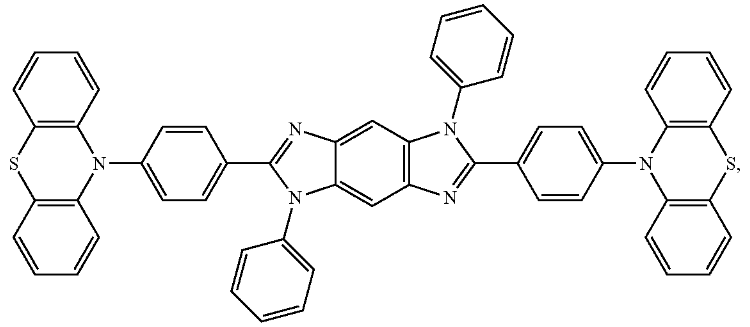
(C-5)
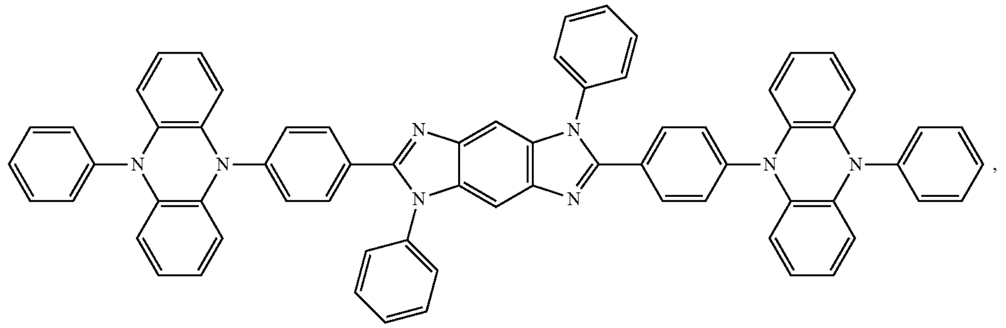
(C-6)
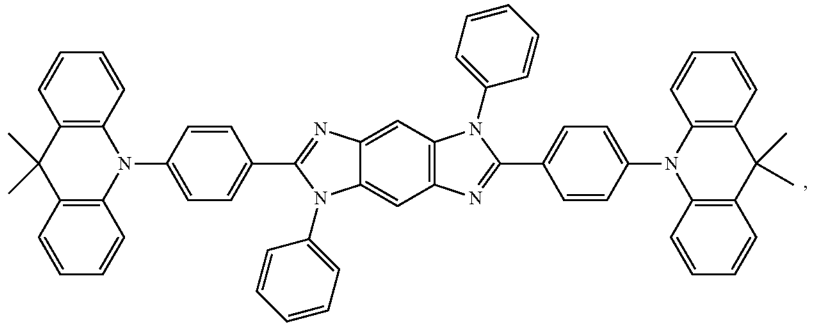
(C-10)
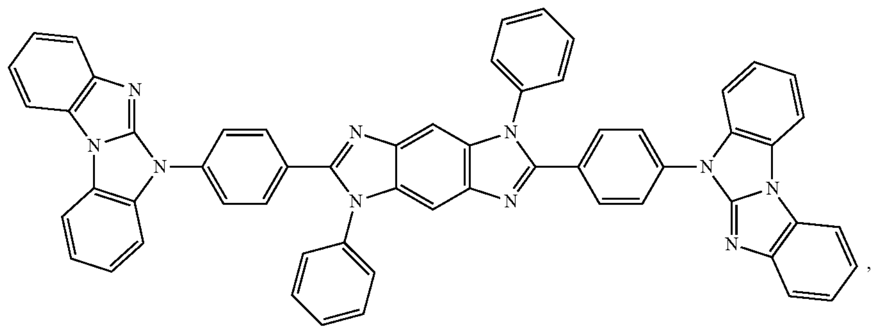

-continued
(C-31)
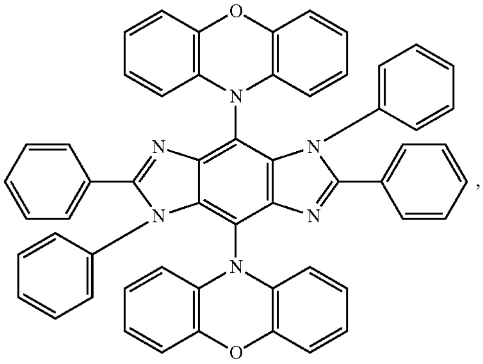
,
(C-32)
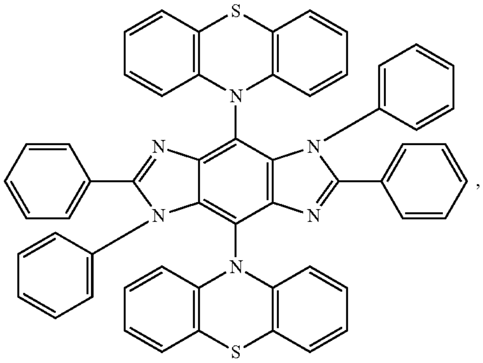
,
(C-35)
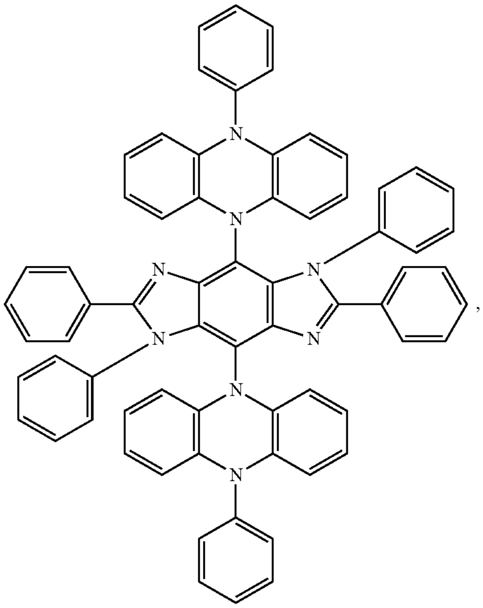
,

-continued
(C-36)
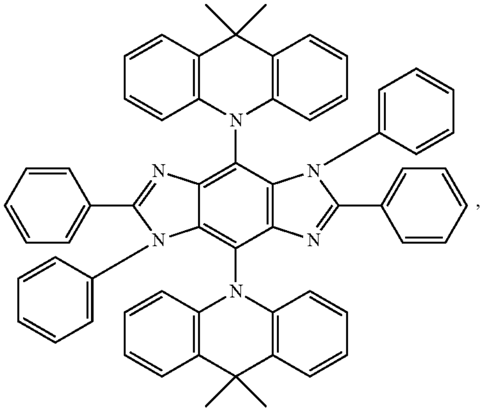
,
(C-41)
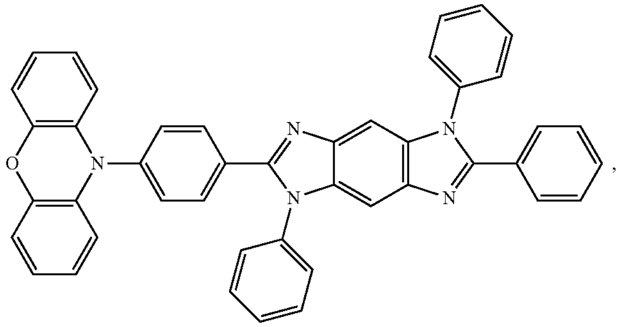
,
(C-42)
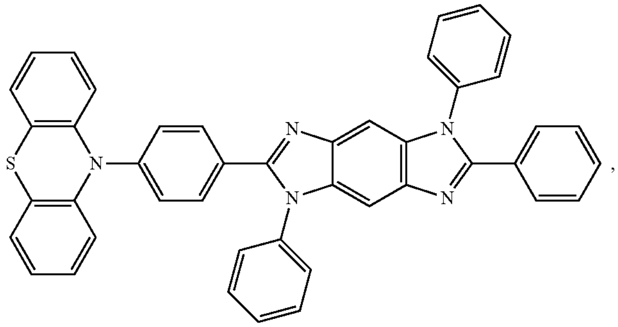
,
(C-45)
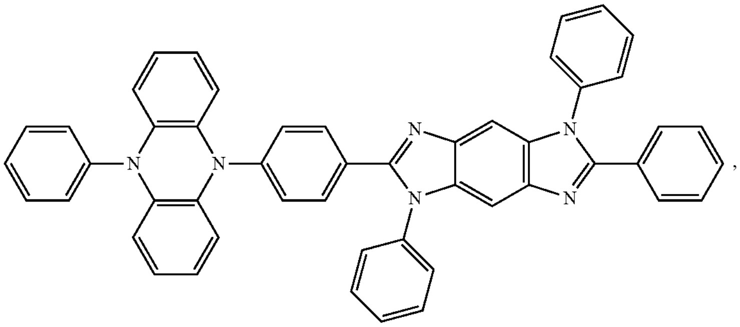
, -continued
(C-46)
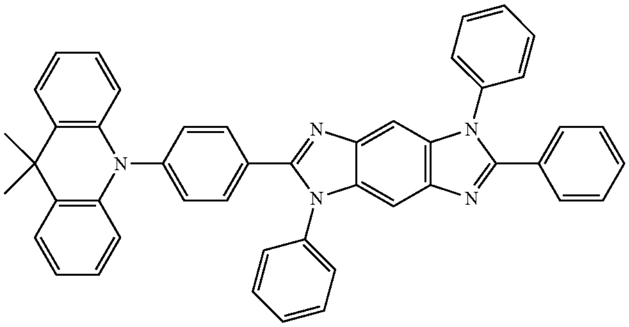
and
(C-50)
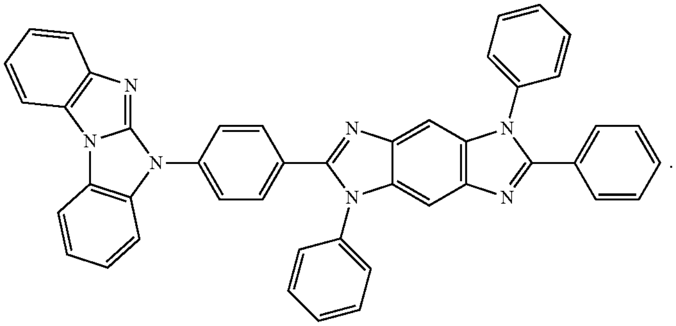
.
Examples of compounds of formula
(Id)
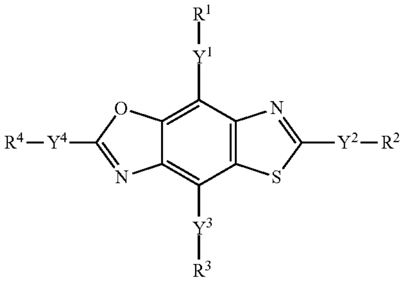
are compounds
(D-1)
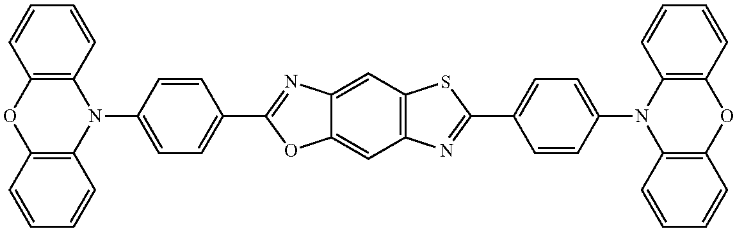
to -continued

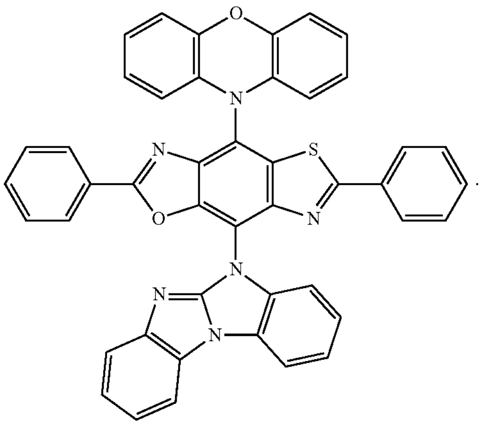

(D-98)

Compounds (D-1) to (D-98) correspond in structure to compounds (A-1) to (A-98), except that the O atom, which is next to carbon atom bonded to $Y^2$, in the core structure of compounds (A-1) to (A-98) is replaced by S.

Among compounds of formula (Id) those are preferred which are substituted by donor groups of formula

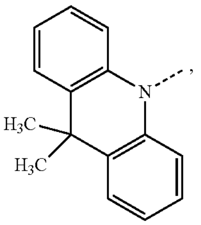

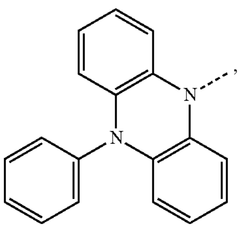

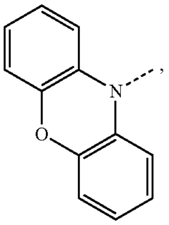

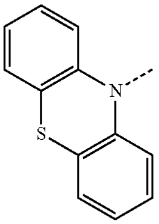

and

-continued

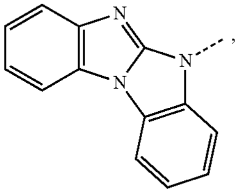

such as, for example, compounds (D-1), (D-2), (D-5), (D-6), (D-10), (D-11), (D-12), (D-15), (D-16), (D-20), (D-21), (D-22), (D-25), (D-26), (D-30), (D-31), (D-32), (D-35), (D-36), (D-40), (D-41), (D-42), (D-45), (D-46), (D-50), (D-51), (D-52), (D-55), (D-56), (D-60), (D-61), (D-62), (D-65), (D-66), (D-70), (D-71), (D-72), (D-75), (D-76), (D-80), (D-81), (D-84), (D-85), (D-89), (D-90), (D-91), (D-93), and (D-98).

The most preferred compounds are compounds (D-1)

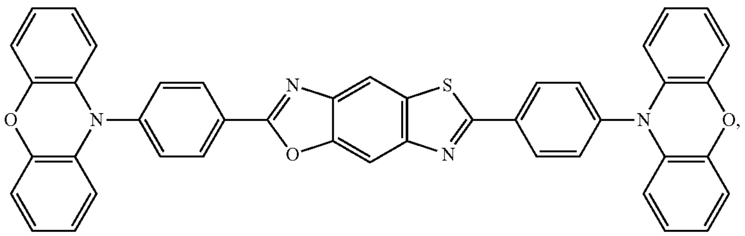

-continued
(D-2)
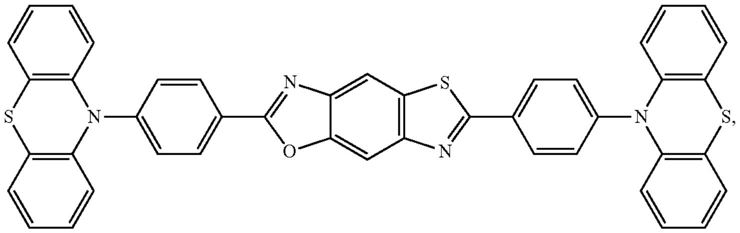
,
(D-5)
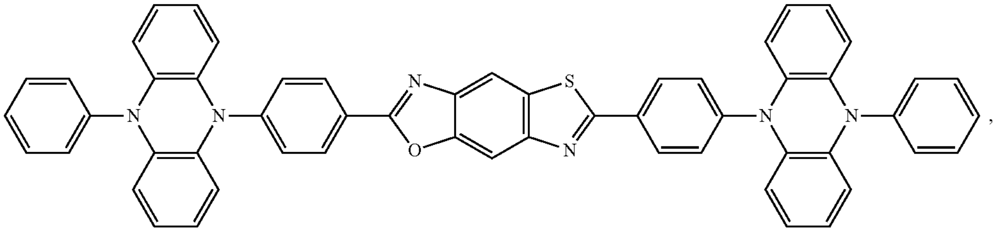
,
(D-6)
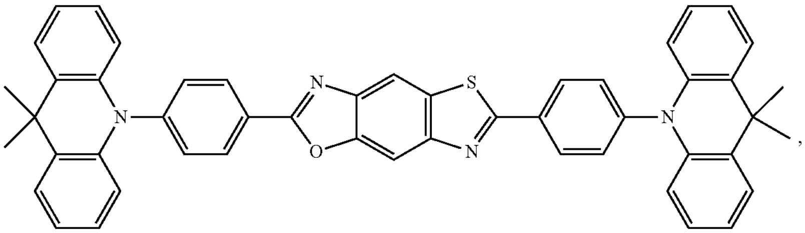
,
(D-10)
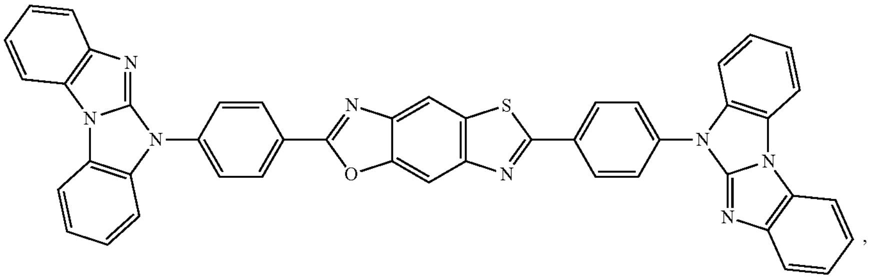
,
(D-31)
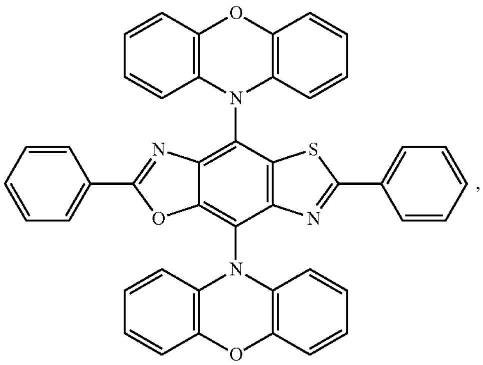
, -continued
(D-32)
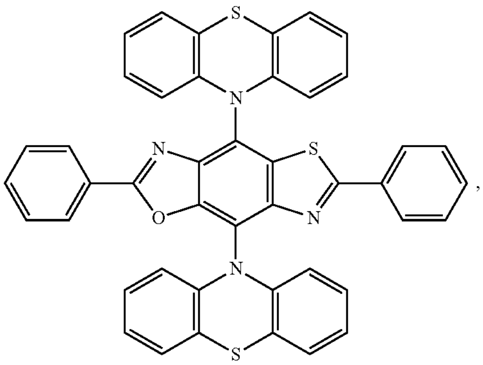
,
(D-35)
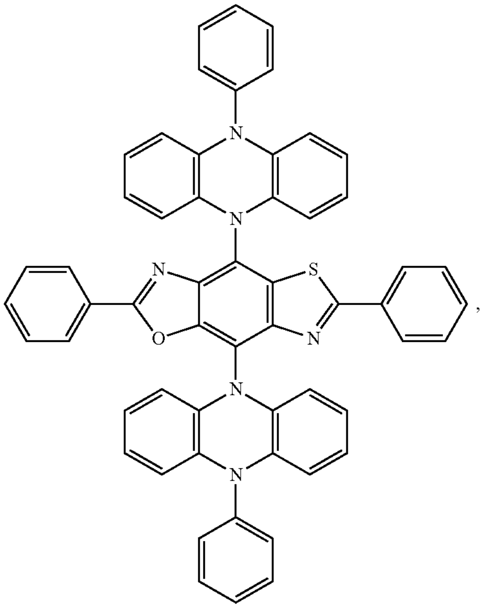
,
(D-36)
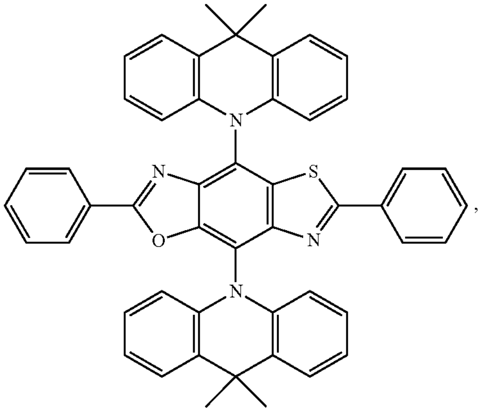
,
(D-41)
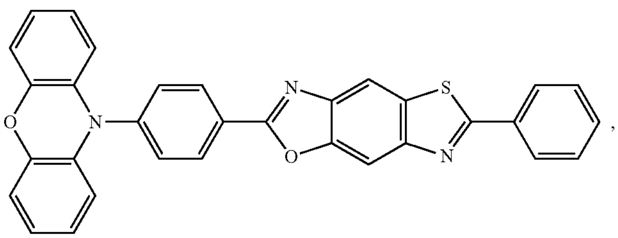
, -continued
(D-42)
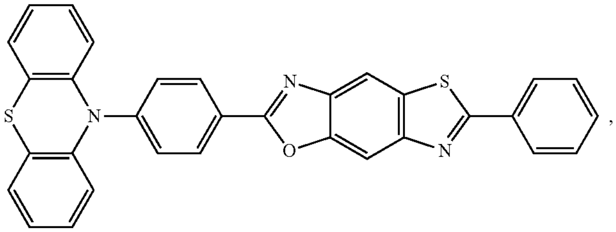
,
(D-45)
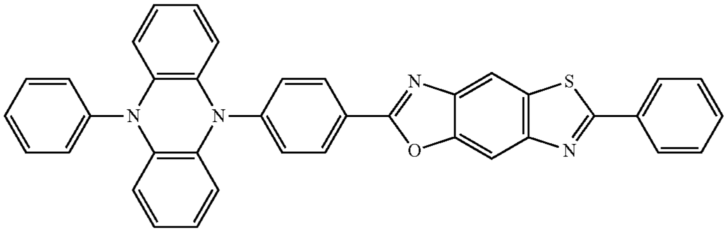
,
(D-46)
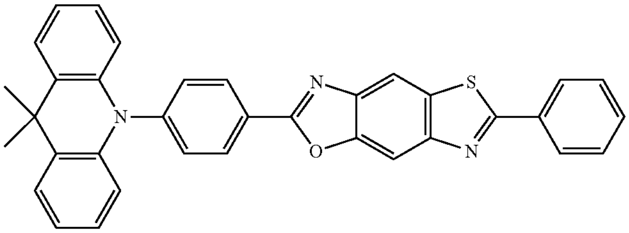
and
(D-50)
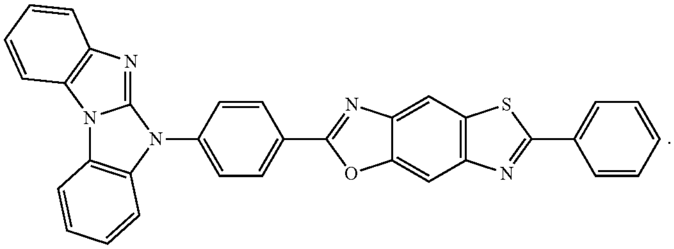
.
Examples of compounds of formula
(Ie)
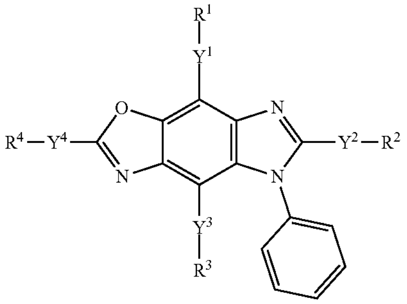
are compounds (E-1)

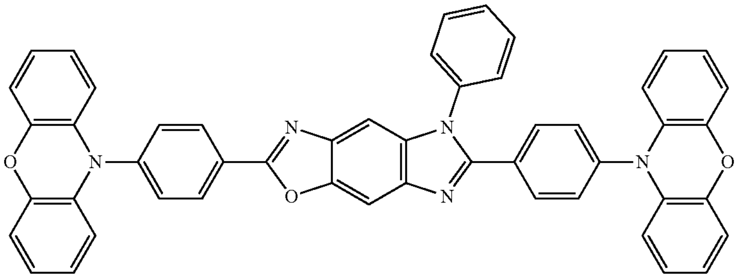

to (E-98)

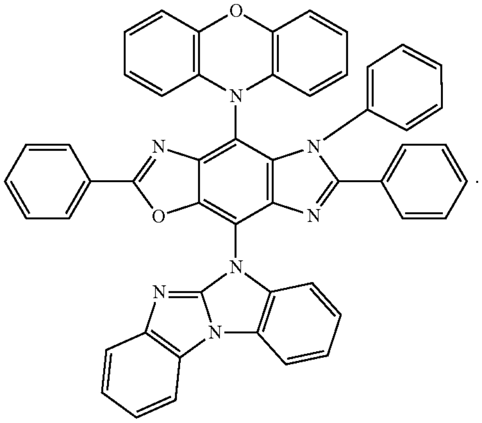

Compounds (E-1) to (E-98) correspond in structure to compounds (A-1) to (A-98), except that the O atom, which is next to carbon atom bonded to $Y^2$, in the core structure of compounds (A-1) to (A-98) is replaced by N-phenyl.

Among compounds of formula (Ie) those are preferred which are substituted by donor groups of formula

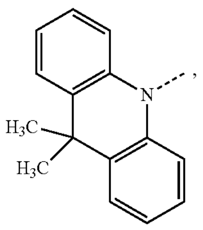

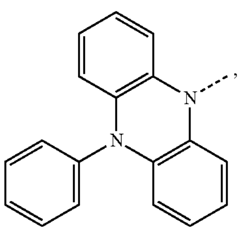

-continued

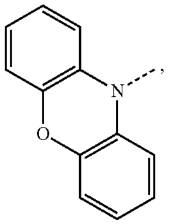

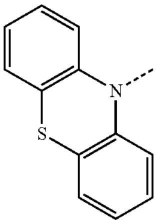

and

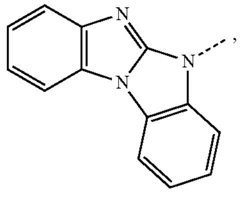

such as, for example, compounds (E-1), (E-2), (E-5), (E-6), (E-10), (E-11), (E-12), (E-15), (E-16), (E-20), (E-21), (E-22), (E-25), (E-26), (E-30), (E-31), (E-32), (E-35), (E-36), (E-40), (E-41), (E-42), (E-45), (E-46), (E-50), (E-51), (E-52), (E-55), (E-56), (E-60), (E-61), (E-62), (E-65), (E-66), (E-70), (E-71), (E-72), (E-75), (E-76), (E-80), (E-81), (E-84), (E-85), (E-89), (E-90), (E-91), (E-93), and (E-98).

The most preferred compounds are compounds
(E-1)
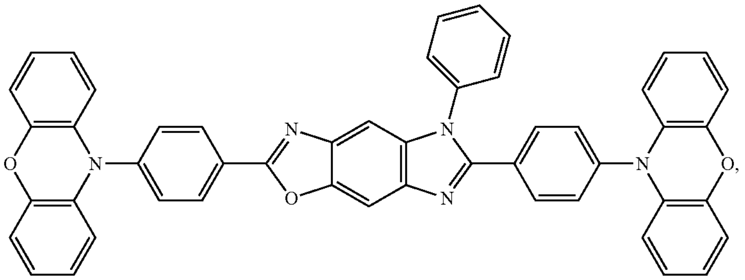
(E-2)
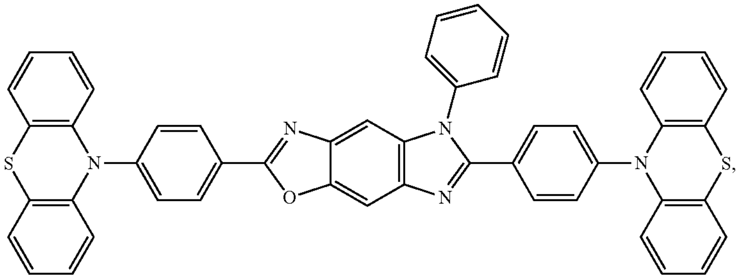
(E-5)
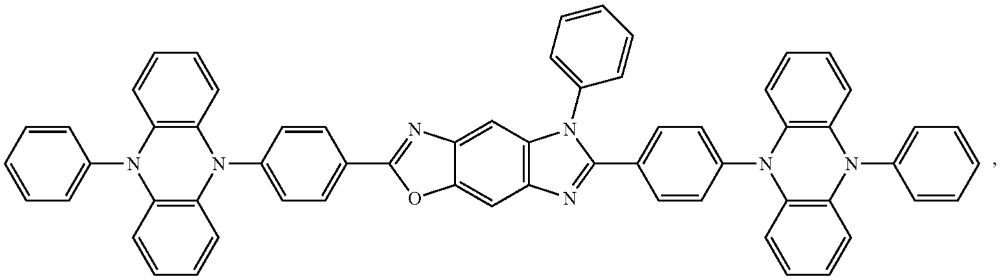
(E-6)
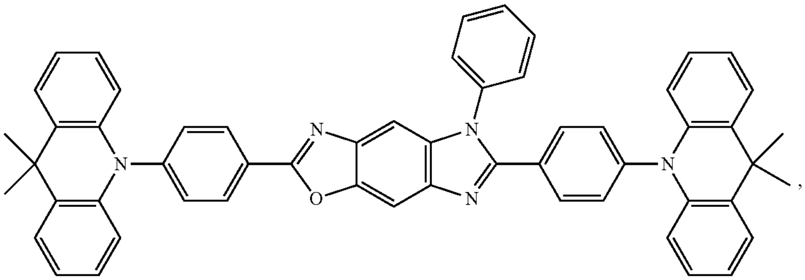
(E-10)
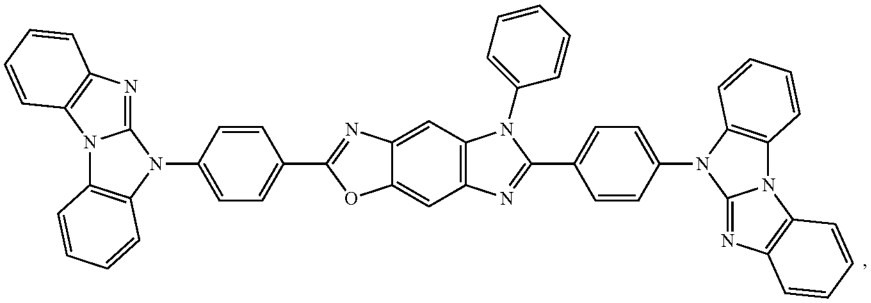

-continued
(E-31)
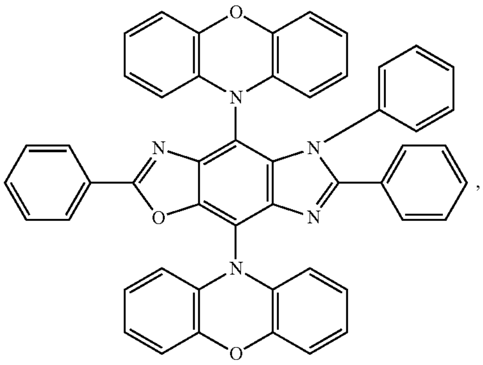
,
(E-32)
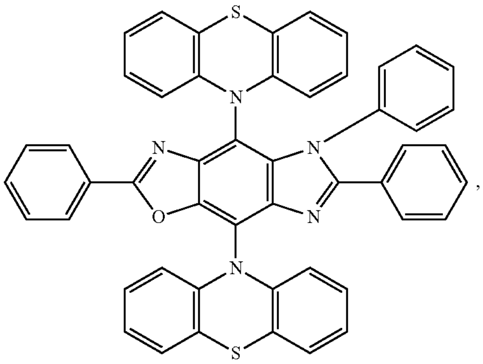
,
(E-35)
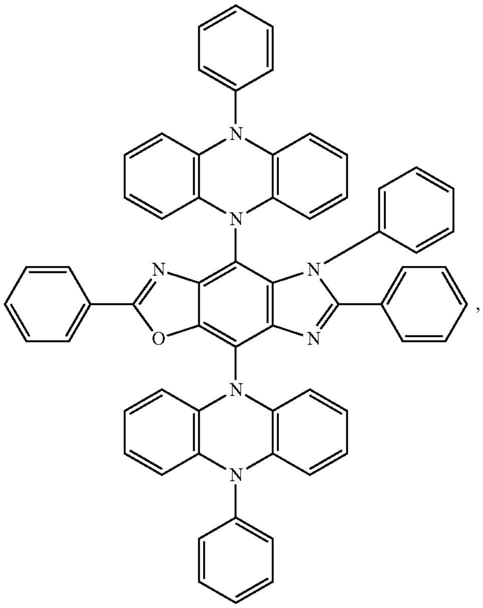
,

-continued
(E-36)
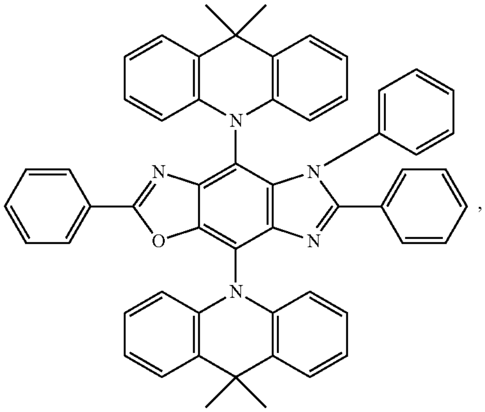
,
(E-41)
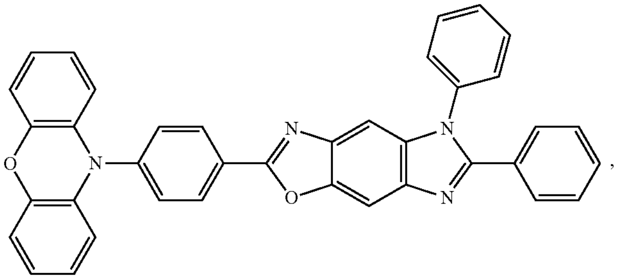
,
(E-42)
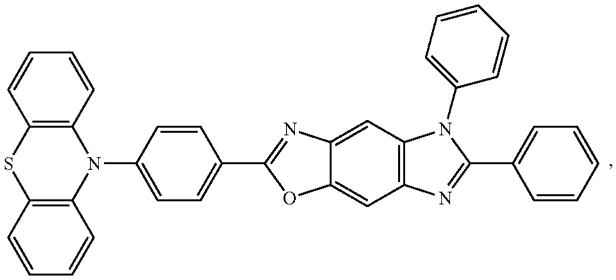
,
(E-45)
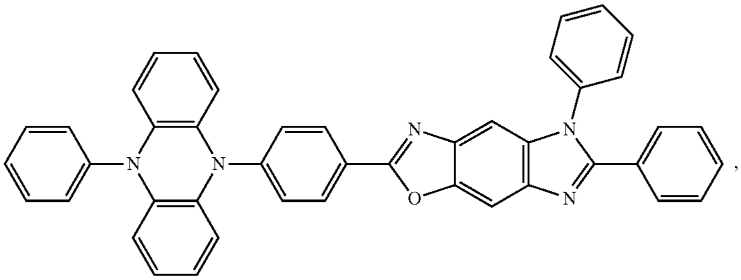
,
(E-46)
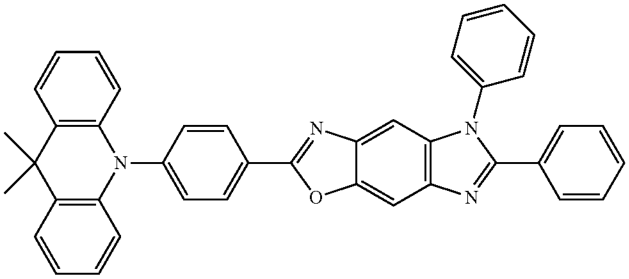
and -continued
(E-50)
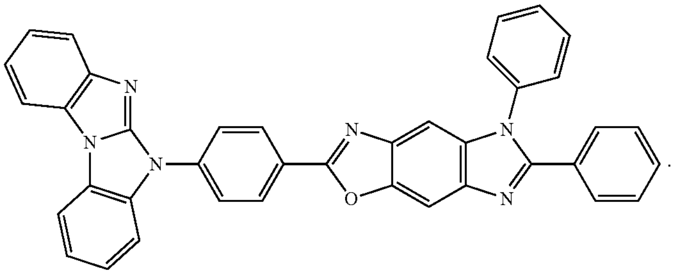
Examples of compounds of formula
(If)
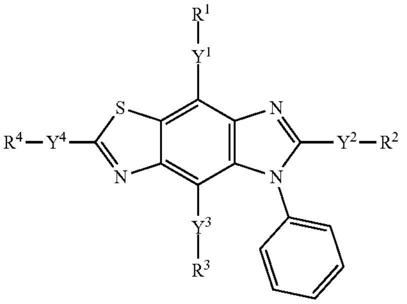
are compounds
(F-1)
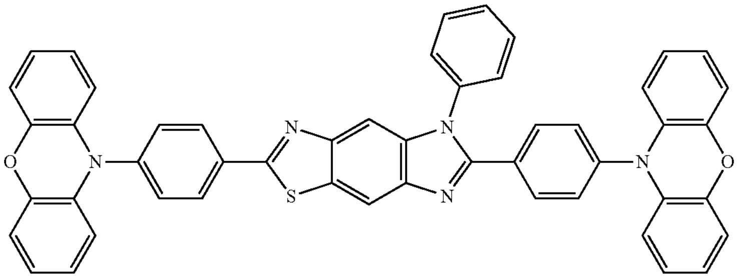
to
(F-98)
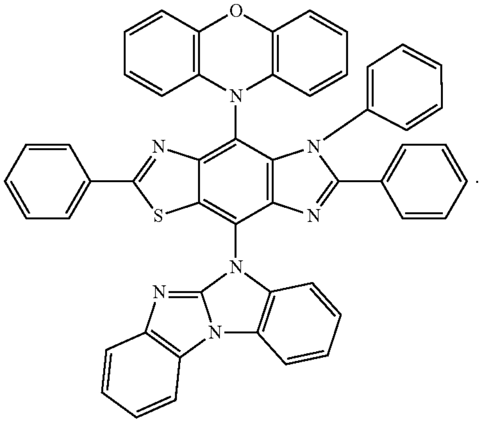
Compounds (F-1) to (F-98) correspond in structure to compounds (A-1) to (A-98), except that the O atom, which is next to carbon atom bonded to $Y^2$, in the core structure of compounds (A-1) to (A-98) is replaced by N-phenyl and the O atom, which is next to carbon atom bonded to $Y^4$, is replaced by S.

Among compounds of formula (If) those are preferred which are substituted by donor groups of formula
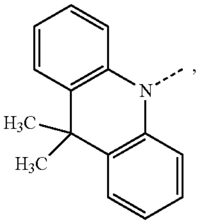
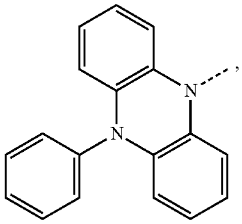
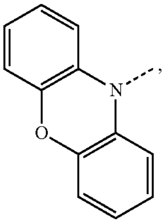
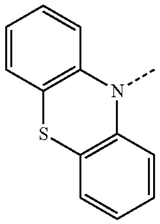
and
-continued
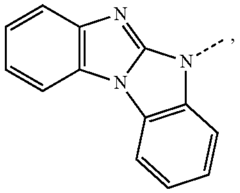
such as, for example, compounds (F-1), (F-2), (F-5), (F-6), (F-10), (F-11), (F-12), (F-15), (F-16), (F-20), (F-21), (F-22), (F-25), (F-26), (F-30), (F-31), (F-32), (F-35), (F-36), (F-40), (F-41), (F-42), (F-45), (F-46), (F-50), (F-51), (F-52), (F-55), (F-56), (F-60), (F-61), (F-62), (F-65), (F-66), (F-70), (F-71), (F-72), (F-75), (F-76), (F-80), (F-81), (F-84), (F-85), (F-89), (F-90), (F-91), (F-93), and (F-98).
The most preferred compounds are compounds
(F-1)
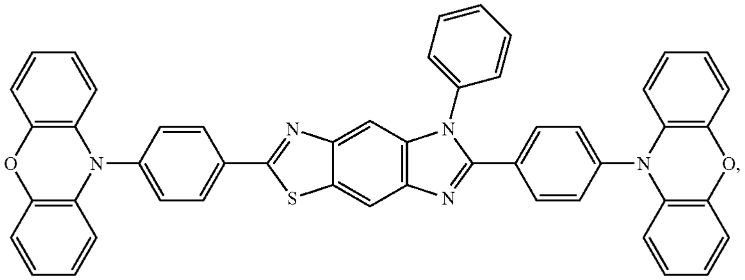
(F-2)
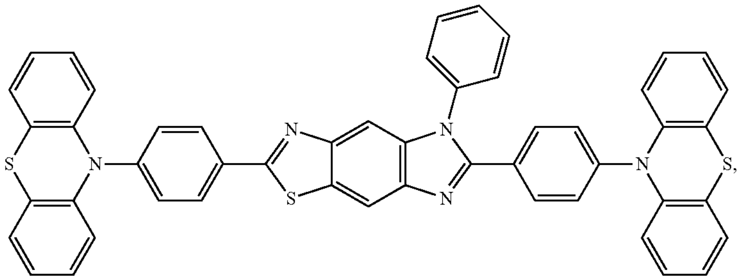
(F-5)
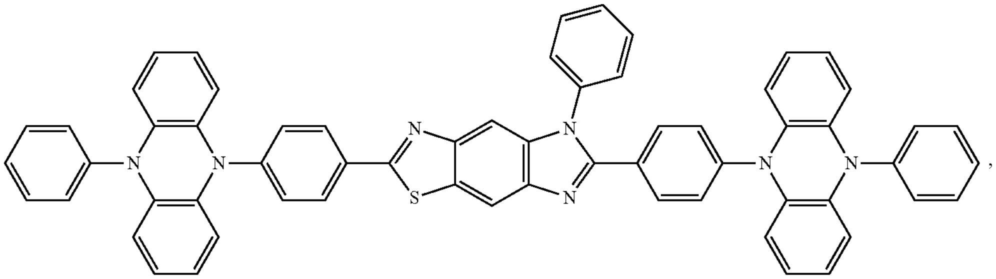

-continued
(F-6)
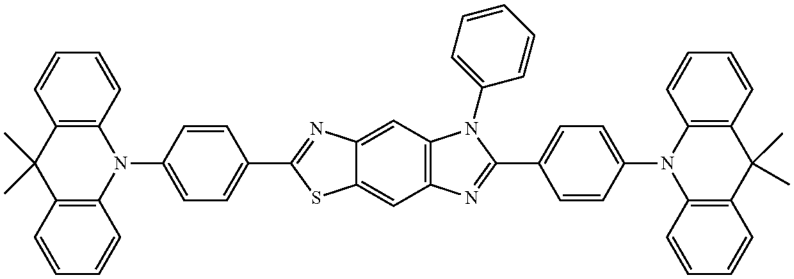
,
(F-10)
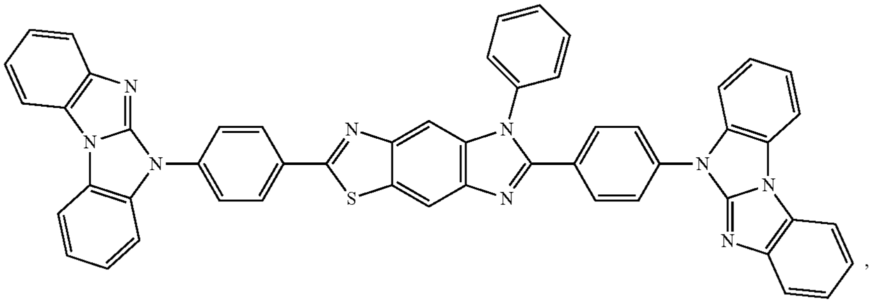
,
(F-31)
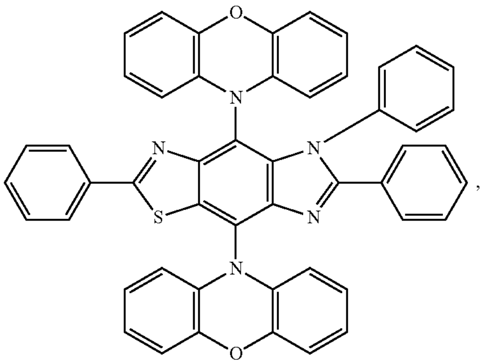
,
(F-32)
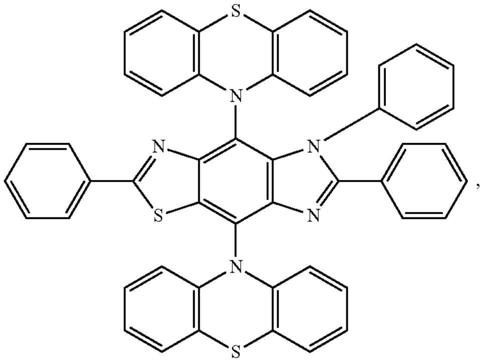
, -continued
(F-35)
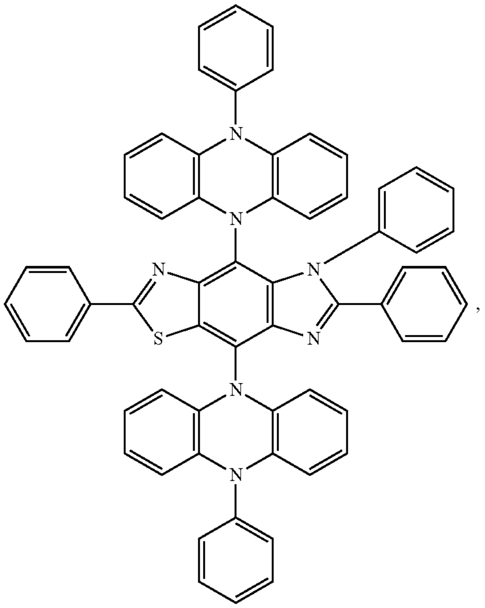
(F-36)
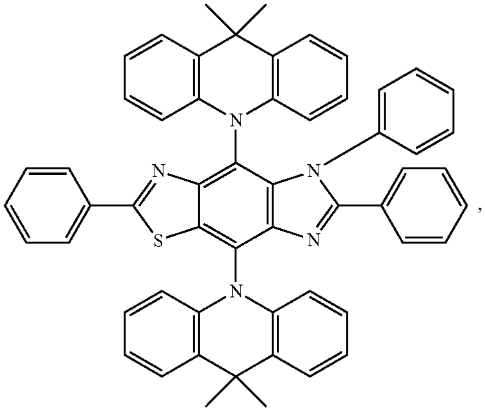
(F-41)
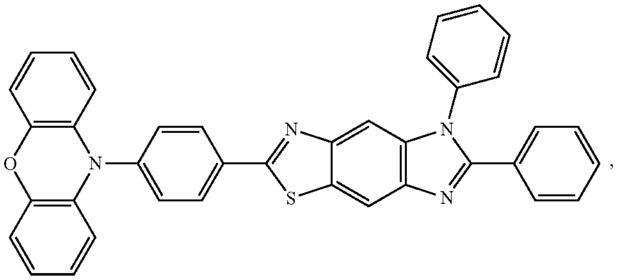
(F-42)
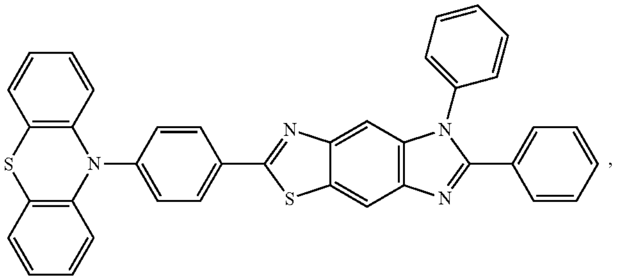

-continued (F-45)

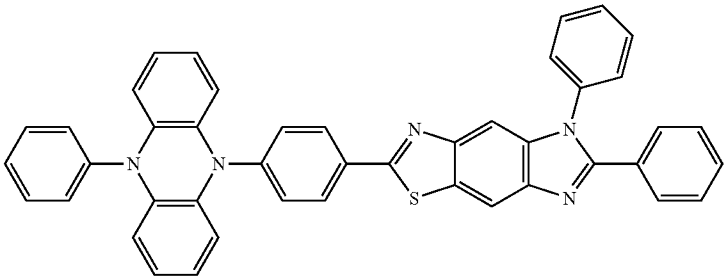

, (F-46)

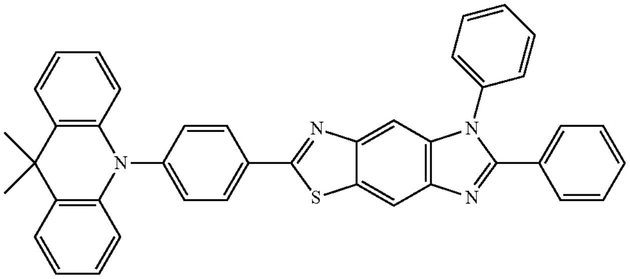

and (F-50)

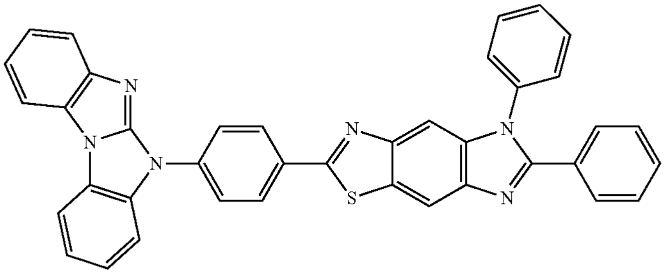

.

Among compounds of formula (Ia), (Ib), (Ic), (Id), (Ie) and (If) compounds of formula (Ia), (Ib) and (Ic) are more preferred. Among compounds of formula (Ia), (Ib) and (Ic) compounds (A-1) to (A-98), (B-1) to (B-98) and (C-1) to (C-98) are preferred, compounds (A-1), (A-2), (A-5), (A-6), (A-10), (A-31), (A-32), (A-35), (A-36), (A-41), (A-42), (A-45), (A-46), (A-50), (B-1), (B-2), (B-5), (B-6), (B-10), (B-31), (B-32), (B-35), (B-36), (B-41), (B-42), (B-45), (B-46), (B-50), (C-1), (C-2), (C-5), (C-6), (C-10), (C-31), (C-32), (C-35), (C-36), (C-41), (C-42), (C-45), (C-46) and (C-50) are most preferred.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_6$-$C_{10}$aryl, which optionally can be substituted, is typically phenyl, naphthyl, especially 1-naphthyl, or 2-naphthyl, or biphenylyl, which may be unsubstituted or substituted by one, or more $C_1$-$C_8$alkyl, $C_1$-$C_8$alkoxy and/or $C_6$-$C_{10}$aryloxy groups, especially $C_1$-$C_8$alkyl, $C_1$-$C_8$alkoxy groups.

$C_6$-$C_{10}$aryloxy, which optionally can be substituted by one, or more $C_1$-$C_8$alkyl and/or $C_1$-$C_8$alkoxy groups, is typically phenoxy, 1-naphthoxy, or 2-naphthoxy.

The present invention is directed to a light-emitting layer comprising the compound of the formula (I).

In addition, the present invention is directed to an organic light emitting element, comprising the compound of the formula (I).

For the compounds of formula (I) the preferences specified above apply.

Compounds of formula (Ia), (Ib), (Ic), (Id), (Ie) and (If) are preferred. Compounds of formula (Ia), (Ib) and (Ic) are more preferred. Among compounds of formula (Ia), (Ib) and (Ic) compounds (A-1) to (A-98), (B-1) to (B-98) and (C-1) to (C-98) are preferred, compounds (A-1), (A-2), (A-5), (A-6), (A-10), (A-31), (A-32), (A-35), (A-36), (A-41), (A-42), (A-45), (A-46), (A-50), (B-1), (B-2), (B-5), (B-6), (B-10), (B-31), (B-32), (B-35), (B-36), (B-41), (B-42), (B-45), (B-46), (B-50), (C-1), (C-2), (C-5), (C-6), (C-10), (C-31), (C-32), (C-35), (C-36), (C-41), (C-42), (C-45), (C-46) and (C-50) are most preferred.

The compounds of formula (I) can be used as host in combination with a fluorescent guest material in the emitting layer of an organic EL element. Known fluorescent materials are usable as the fluorescent guest material. Examples of the fluorescent guest material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative. Examples are 2,5,8,11-tetra-tert-butylperylene (TBPe), 9,10-bis[N,N-di-(p-tolyl)amino]anthracene (TTPA), 2,8-di-tert-butyl-5,11-bis(4-tert-butylphenyl)-6,12-diphenyltetracene (TBRb) and dibenzo{[f,f']-4,4',7,7'-tetraphenyl}diindeno[1,2,3-cd:1',2',3'-Im]perylene (DBP). In case of using the compound of formula (I) as host material, the content of the compound of formula (I) in the light-emitting layer falls within the range of 51 to 99 wt %, preferably 80 to 99 wt %.

Alternatively, the compounds of formula (I) can be used as guest in combination with a host material in the emitting layer of an organic EL element. In said embodiment the compound of formula (I), i.e. the organic light-emitting material, has preferably a difference between excited singlet energy and excited triplet energy (($\Delta E_{ST}$) of 0.5 eV or less, more preferably $\Delta E_{ST}$ of 0.35 eV or less. The organic light-emitting material may be used alone in the light-emitting layer. However, as necessary, for the purpose of, for example, confining, in the organic light-emitting material, singlet excitons and triplet excitons generated in the organic light-emitting material, the organic light-emitting material of the present invention and an organic compound which has a higher value of at least any one of excited singlet energy and excited triplet energy than those of the organic light-emitting material and serves as a host material are preferably used in the light-emitting layer. At least any one of the excited singlet energy ($S_{1h}$) and excited triplet energy ($T_{1h}$) of the host compound is preferably higher by 0.1 eV or more, particularly preferably higher by 0.2 eV or more than the excited singlet energy ($S_{1g}$) and excited triplet energy ($T_{1g}$) of the organic light-emitting material of the present invention. That is, it is preferred that one or both of $(S_{1h})-(S_{1g})>0.1$ eV and $(T_{1h})-(T_{1g})>0.1$ eV be satisfied and it is more preferred that one or both of $(S_{1h})-(S_{1g})>0.2$ eV and $(T_{1h})-(T_{1g})>0.2$ eV be satisfied.

The organic EL element of the present invention has, as essential layers, an anode, a hole-transporting layer, a light-emitting layer, and a cathode.

Further, the organic EL element of the present invention may have, as layers other than the essential layers, an electron-transporting layer, an electron-injecting layer, an electron-blocking layer, a hole-blocking layer, and an exciton element layer. In addition, the hole-transporting layer may be a hole-injecting/transporting layer having a hole-injecting function and the electron-transporting layer may be an electron-injecting/transporting layer having an electron-injecting function.

The organic EL element of the present invention may comprise in this order: a substrate, an anode, a hole-injecting layer, a hole-transporting layer, a light-emitting layer, an electron-transporting layer and a cathode. Alternatively, the cathode, the electron-transporting layer, the light-emitting layer, the hole-transporting layer, and the anode may be laminated on the substrate in the stated order.

Substrate

The organic EL element of the present invention is preferably supported by a substrate. The substrate is not particularly limited and may be any substrate which is conventionally used in an organic EL element. For example, a substrate formed of glass, transparent plastic, quartz, or the like may be used.

Anode

Preferably used as the anode in the organic EL element is one using, as an electrode substance, any of a metal, an alloy, an electrically conductive compound, and a mixture thereof with a high work function (4 eV or more). Specific examples of such electrode substance include metals such as Au and conductive transparent materials such as CuI, indium tin oxide (ITO), $SnO_2$, and ZnO. Further, a material capable of producing an amorphous transparent conductive film such as IDIXO ($In_2O_3$—ZnO) may be used. In the production of the anode, it is possible to form any of those electrode substances into a thin film by a method such as vapor deposition or sputtering, and then form a pattern having a desired shape by a photolithographic method. Alternatively, in the case of using a coatable substance such as an organic conductive compound, it is also possible to employ a wet film-forming method of a printing mode, a coating mode, or the like.

Cathode

Meanwhile, used as the cathode is one using, as an electrode substance, any of a metal (referred to as electron-injecting metal), an alloy, an electrically conductive compound, and a mixture thereof with a low work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, from the viewpoints of electron-injecting property and durability against oxidation and the like, a mixture of an electron-injecting metal and a second metal, which has a work function value higher than that of the electron-injecting metal and is a stable metal, such as a magnesium/silver mixture, a magnesium/aluminum mixture, a magnesium/indium mixture, an aluminum/aluminum oxide ($Al_2O_3$) mixture, a lithium/aluminum mixture, or aluminum is suitable. It should be noted that a case where any one of the anode and the cathode of the organic EL element is transparent or translucent in order to transmit emitted light is advantageous because light emission luminance is improved.

Light-Emitting Layer

The light-emitting layer is a layer which emits light after excitons have been generated through the recombination of holes and electrons injected respectively from an anode and a cathode. The light-emitting layer preferably includes an organic light-emitting material and a host material. As the organic light-emitting material, there may be used one kind or two or more kinds selected from the compounds of formula (I). In order that the organic EL element of the present invention exhibits high luminous efficiency, it is important to confine, in the organic light-emitting material, singlet excitons and triplet excitons generated in the organic light-emitting material. Accordingly, it is preferred to use the host material in addition to the organic light-emitting material in the light-emitting layer. As the host material, there may be used an organic compound having a higher value of at least any one of excited singlet energy and excited triplet energy than those of the organic light-emitting material of the present invention. This allows singlet excitons and triplet excitons generated in the organic light-emitting material of the present invention to be confined in the molecule of the organic light-emitting material of the present invention and allows the luminous efficiency to be exhibited sufficiently. In the organic EL element of the present invention, light is emitted from the organic light-emitting material of the present invention included in the light-emitting layer.

In case of using the host material, the content of the organic light-emitting material of the present invention in the light-emitting layer fall within the range of 1 to 50 wt %, preferably 1 to 20 wt %.

The host material in the light-emitting layer is preferably an organic compound which has a hole-transporting ability and/or an electron-transporting ability, prevents an emission wavelength from becoming longer, and has a high glass transition temperature.

The host material may be a polymer, for example poly (N-vinylcarbazole) or polysilane. The host material may, however, be a small molecule, for example 4,4'-N,N'-dicarbazolebiphenyl (CDP=CBP), 2,6-bis(N-carbazolyl)phenyl (mCP), 3,3-Di(9H-carbazol-9-yl)biphenyl (mCBP),

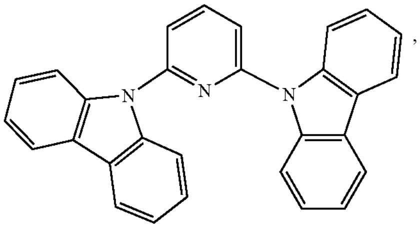

(PYD2)

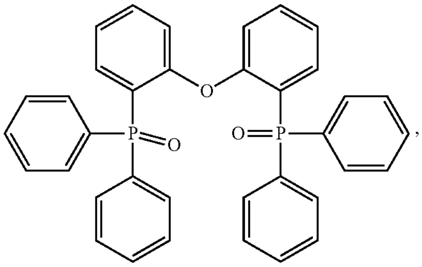

(DPEPO)

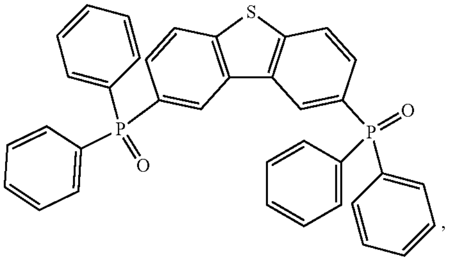

(PPT)

-continued

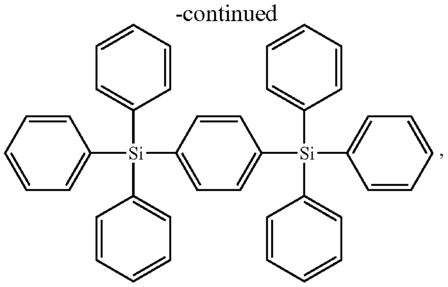

(UGH-2)

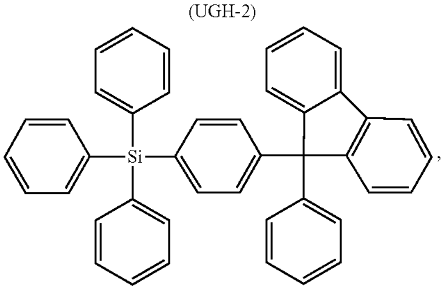

(TPSi-F)

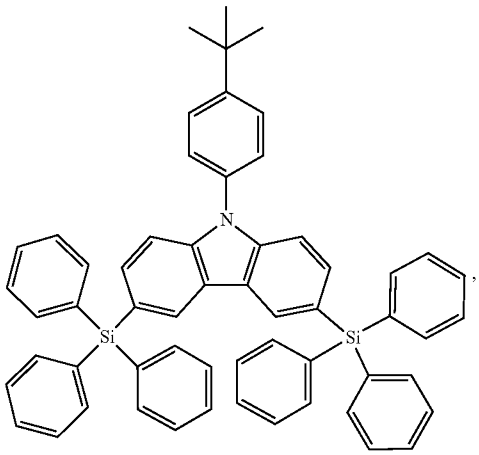

(CzSi)

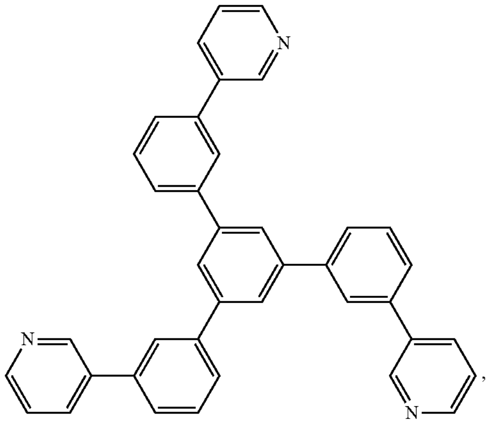

(TmPyPB)

or tertiary aromatic amines, for example 4-carbazol-9-yl-N, N-bis(4-carbazol-9-ylphenyl)aniline (TCTA).

Injecting Layer

The injecting layer refers to a layer to be provided between an electrode and an organic layer for the purposes of reducing a driving voltage and improving a light emission luminance. The injecting layer includes a hole-injecting layer and an electron-injecting layer, and may be provided between the anode and the light-emitting layer or the hole-transporting layer, and between the cathode and the light-emitting layer or the electron-transporting layer. The injecting layer may be provided as necessary.

Customarily used hole injection materials include a-NPD, CuPc, MTDATA, or dipyrazino[2,34:2',3'-h]quinoxaline-2,3,6,7,10,11-hexacarbonitrile (HAT-CN). Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Lithium-comprising organometallic compounds such as 8-hydroxyquinolatolithium (Liq), CsF, NaF, KF, $Cs_2CO_3$ or LiF may be applied between the electron transport layer and the cathode as an electron injection layer in order to reduce the operating voltage.

Blocking Layer

The blocking layer is capable of blocking charges (electrons or holes) and/or excitons present in the light-emitting layer from diffusing to the outside of the light-emitting layer. The electron-blocking layer may be arranged between the light-emitting layer and the hole-transporting layer, and blocks electrons from passing through the light-emitting layer toward the hole-transporting layer. Similarly, the hole-blocking layer may be arranged between the light-emitting layer and the electron-transporting layer, and blocks holes from passing through the light-emitting layer toward the electron-transporting layer. The blocking layer may also be used for blocking excitons from diffusing to the outside of the light-emitting layer. That is, the electron-blocking layer and the hole-blocking layer may each have a function of an exciton-blocking layer as well. The electron-blocking layer or exciton-blocking layer as used herein is meant to include a layer having a function of an electron-blocking layer and an exciton-blocking layer in one layer.

Hole-Blocking Layer

The hole-blocking layer has a function of the electron-transporting layer in a broad sense. The hole-blocking layer has a role in blocking holes from reaching the electron-transporting layer while transporting electrons. This can improve the probability of recombination of electrons and holes in the light-emitting layer. As a material for the hole-blocking layer, a material for the electron-transporting layer to be described below may be used as necessary.

Electron-Blocking Layer

The electron-blocking layer has a function of transporting holes in a broad sense. The electron-blocking layer has a role in blocking electrons from reaching the hole-transporting layer while transporting holes. This can improve the probability of recombination of electrons and holes in the light-emitting layer.

Exciton-Blocking Layer

The exciton-blocking layer refers to a layer for blocking excitons, which are generated by the recombination of holes and electrons in the light-emitting layer, from diffusing to a charge-transporting layer. The insertion of this layer allows excitons to be efficiently confined in the light-emitting layer, which can improve the luminous efficiency of an element. The exciton-blocking layer may be inserted on any of the anode side and the cathode side of the adjacent light-emitting layer, and may be simultaneously inserted on both of the sides. That is, when the exciton-blocking layer is provided on the anode side, the layer may be inserted between the hole-transporting layer and the light-emitting layer so as to be adjacent to the light-emitting layer. When the exciton-blocking layer is inserted on the cathode side, the layer may be inserted between the light-emitting layer and the cathode so as to be adjacent to the light-emitting layer. Further, the hole-injecting layer, the electron-blocking layer, and the like may be provided between the anode and the exciton-blocking layer adjacent to the anode side of the light-emitting layer, and the electron-injecting layer, the electron-transporting layer, the hole-blocking layer, and the like may be provided between the cathode and the exciton-blocking layer adjacent to the cathode side of the light-emitting layer. In the case of providing the blocking layer, it is preferred that at least any one of the excited singlet energy and excited triplet energy of a material to be used as the blocking layer be higher than the excited singlet energy and excited triplet energy of a light-emitting material.

Hole blocker materials typically used are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2''-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]phenanthroline,

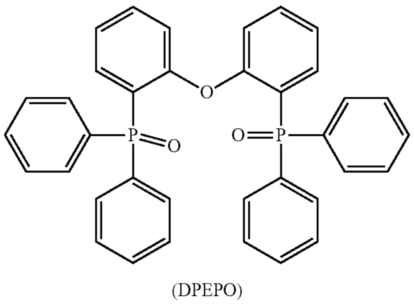 [SMILES: O=P(c1ccccc1)(c1ccccc1)c1ccccc1Oc1ccccc1P(=O)(c1ccccc1)c1ccccc1]

(DPEPO)

and 2,4,6-tris(biphenyl-3-yl)-1,3,5-triazine (T2T).

Hole-Transporting Layer

The hole-transporting layer is formed of a hole-transporting material having a function of transporting holes. The hole-transporting layer may be provided in a single layer or a plurality of layers.

The hole-transporting material has any of hole-injecting or -transporting property and electron-blocking property, and may be an organic material or an inorganic material. An applicable known hole-transporting material is exemplified by a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, or a conducting polymeric oligomer, particularly a thiophene oligomer. However, preferably used are a porphyrin compound, an aromatic tertiary amine compound, and a styrylamine compound, and more preferably used is an aromatic tertiary amine compound. Customarily used hole-transporting molecules are selected from the group consisting of

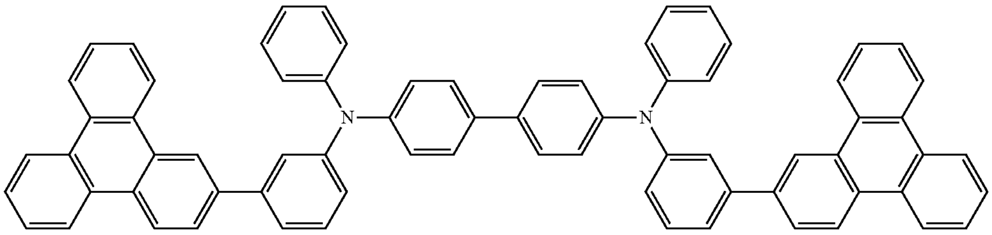

,

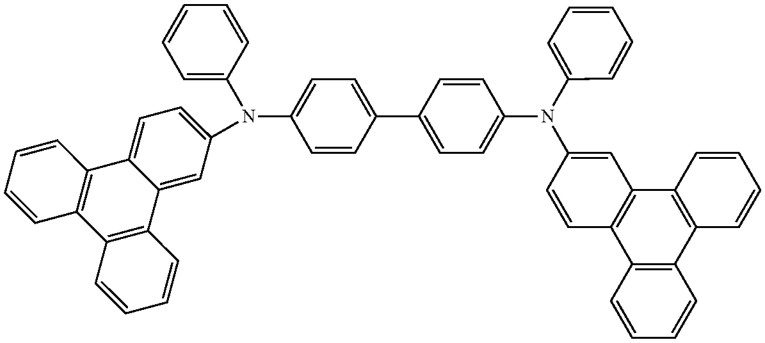

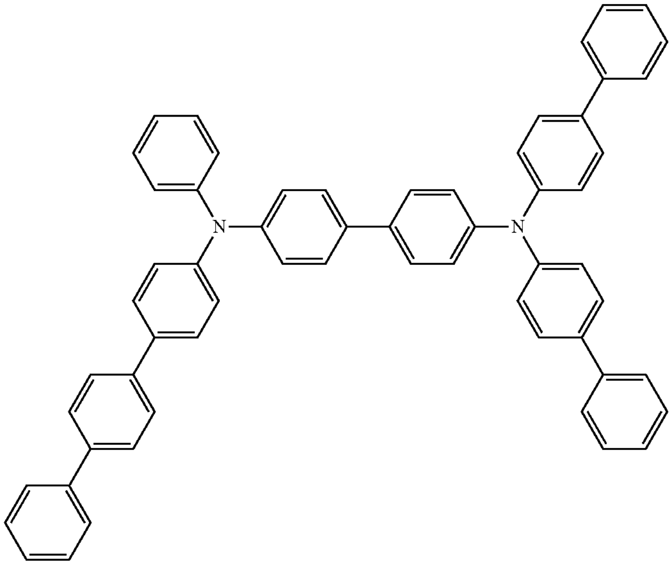

(4-phenyl-N-(4-phenylphenyl)-N-[4-[4-(N-[4-(4-phenyl phenyl)phenyl]anilino)phenyl]phenyl]aniline),

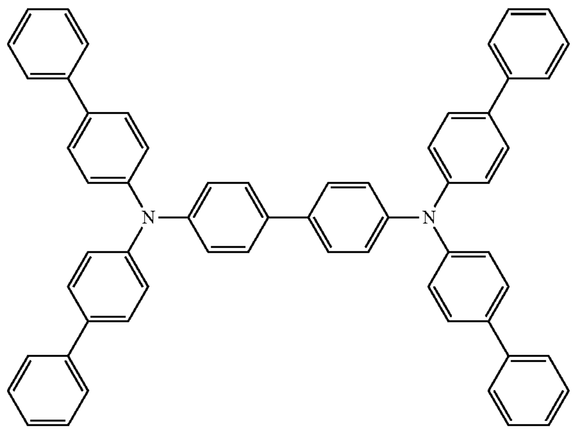 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

(4-phenyl-N-(4-phenylphenyl)-N-[4-[4-(4-phenyl-N-(4-phenylphenyl)anilino)phenyl]phenyl]aniline),

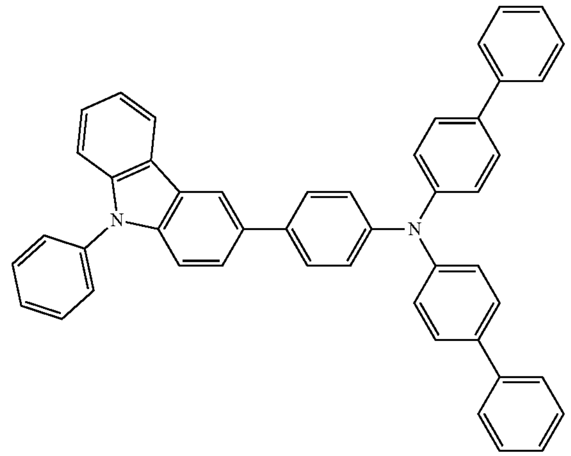 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

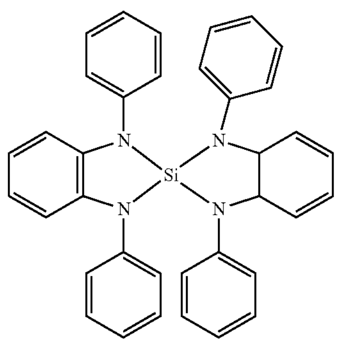 [SMILES: C1=CC2C(C=C1)N(c1ccccc1)[Si]1(N(c3ccccc3)c3ccccc3N1c1ccccc1)N2c1ccccc1]

(1,1',3,3'-tetraphenylspiro[1,3,2-benzodiazasilole-2,2'-3a, 7a-dihydro-1,3,2-benzodiazasilole]),

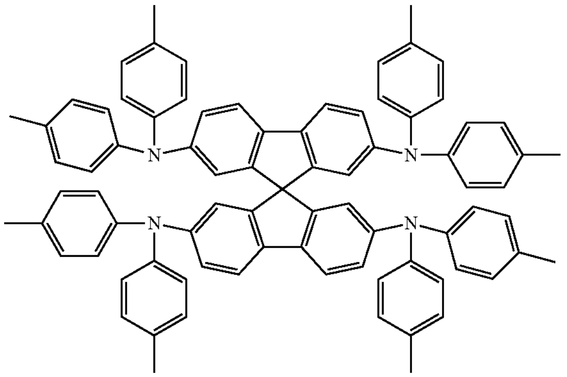

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]-cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl] 5-[p(diethylamino)phenyl]pyrazoline (PPR or DEASP), 1,2-trans-bis(9H-carbazoal9-yl)cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines,

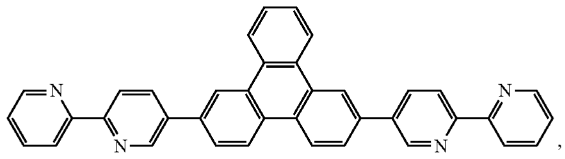, (BPY-TP2)

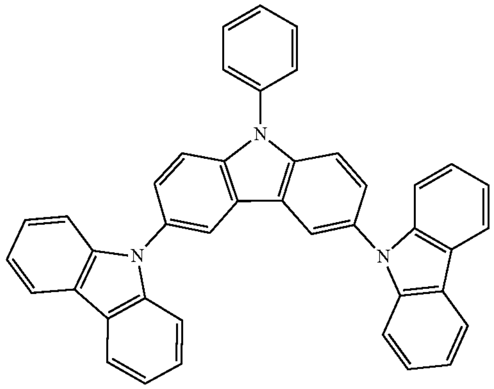

(Tris-PCz)

and CzSi. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly (4-styrenesulfonate) also called PEDOT/PSS.

Electron-Transporting Layer

The electron-transporting layer is formed of a material having a function of transporting electrons. The electron-transporting layer may be provided in a single layer or a plurality of layers.

An electron-transporting material (may also serve as a hole-blocking material) has only to have a function of transporting electrons, which are injected from the cathode, to the light-emitting layer. An applicable electron-transporting layer is exemplified by a nitro-substituted fluorene derivative, a diphenylquinone derivative, a thiopyran dioxide derivative, carbodiimide, a fluorenylidenemethane derivative, an anthraquinodimethane derivative, an anthrone derivative, or an oxadiazole derivative. In addition, in oxadiazole derivative, a thiadiazole derivative in which an oxygen atom of an oxadiazole ring is substituted by a sulfur atom, or a quinoxaline derivative having a quinoxaline ring known as an electron-withdrawing group may also be used as the electron-transporting material. In addition, a polymer material obtained by introducing any of those materials into a polymer chain, or a polymer material including any of those materials in a polymer main chain may also be used. Suitable electron-transporting materials comprise 1,3,5-tris (N-phenyl-2-benzylimidazolyl)benzene (TPBi),

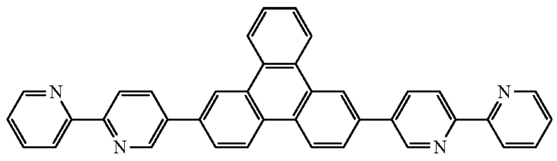, (BPY-TP2)

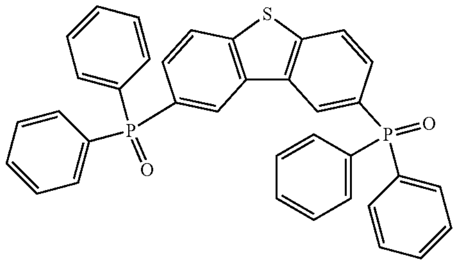, (PPT)

metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

Examples of possible element structures are shown below:

ITO (100 nm)/α-NPD (35 nm)/CBP: 6% by weight cpd. of formula (I) (15 nm)/TPBi (65 nm)/LiF (0.8 nm)/Al (80 nm)

ITO (100 nm)/α-NPD (40 nm)/mCP/PPT: 6% by weight cpd. of formula (I) (20 nm)/PPT (40 nm)/LiF (0.8 nm)/Al (80 nm)

ITO (30-100 nm)/α-NPD (60 nm)/mCP: 6% by weight cpd. of formula (I) (20 nm)/Bphen (40 nm)/MgAg (100 nm)/Ag (20 nm)

ITO (30-100 nm)/α-NPD (60 nm)/PYD2: 6% by weight cpd. of formula (I) (20 nm)/Bphen (40 nm)/MgAg (100 nm)/Al (20 nm)

ITO/α-NPD (35 nm)/6% by weight cpd. of formula (I): CBP (15 nm)/TPBi (65 nm)/LiF (0.8 nm)/Al (80 nm)

ITO (100 nm)/HAT-CN (10 nm)/Tris-PCz (30 nm)/CBP: 3, 6, 10, or 15% by weight cpd. of formula (I) (30 nm)/BPY-TP2 (40 nm)/LiF (0.8 nm)/Al (100 nm)

ITO (100 nm)/α-NPD (35 nm)/CBP (10 nm)/DPEPO: 6 to 12% by weight cpd. of formula (I) (15 nm)/DPEPO (10 nm)/TPBi (65 nm)/LiF (0.5 nm)/Al (80 nm)]

ITO (100 nm)/HAT-CN (10 nm)/Tris-PCz (30 nm)/mCBP: 6 to 12% by weight cpd. of formula (I) (30 nm)/T2T (10 nm)/Bpy-TP2 (40 nm)/LiF (0.8 nm)/Al (100 nm)

ITO (100 nm)/α-NPD (30 nm)/TCTA (20 nm)/CzSi (10 nm)/DPEPO: 6 to 12% by weight cpd. of formula (I) (20 nm)/DPEPO (10 nm)/TPBi (30 nm)/LiF (0.8 nm)/Al (100 nm)

ITO: indium/tin oxide; α-NPD: 4,4'-bis[N-(1-naphthyl)-N-phenylamino]biphenyl; CBP: 4,4'-N,N'-dicarbazolebiphenyl; TPBi: 1,3,5-tris(N-phenyl-2-benzylimidazolyl)benzene; mCP: 2,6-bis(N-carbazolyl)pyridine; PPT:

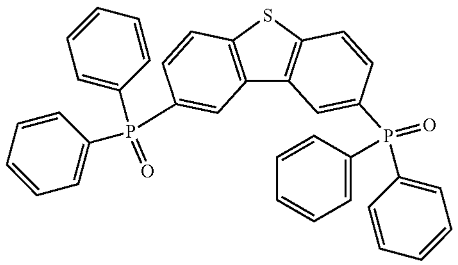;

Bphen: 4,7-diphenyl-1,10-phenanthroline; PYD2:

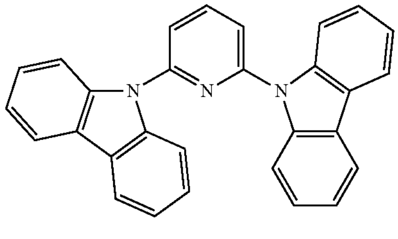;

HAT-CN: dipyrazino[2,3-f:2',3'-h]quinoxaline-2,3,6,7,10,11-hexacarbonitrile; Tris-PCz:

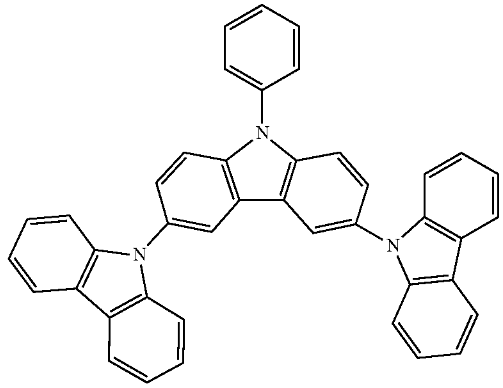

;

Tris-PCz

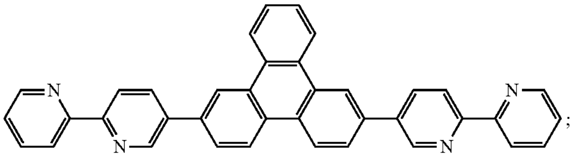

;

BPY-TP2

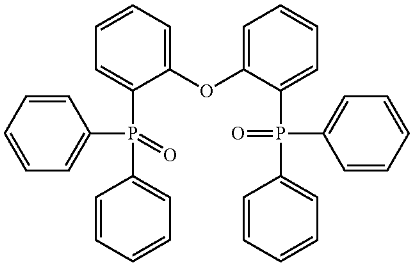

.

DPEPO

The organic EL element emits light when an electric field is applied between an anode and a cathode of the resultant element.

The organic EL element of the present invention may be applied to any of a single element, an element formed of a structure with arrangement in an array fashion, and a structure in which an anode and a cathode are arranged in an X-Y matrix fashion.

According to the present invention, there is provided an element having significantly improved luminous efficiency as compared to a conventional element using light emission from a singlet state by incorporating the organic light-emitting material having a specific skeleton of the present invention into the light-emitting layer which emits delayed fluorescence. The element can exhibit excellent performance when being applied to a full-color or multi-color panel. The element may also be utilized in a backlight, lighting, and the like.

The above compounds of formula (I) can be used in electrophotographic photoreceptors, photoelectric converters, sensors, dye lasers, solar cell devices and organic light emitting elements.

The compounds of the present invention can be synthesized using copper catalyzed Ullmann conditions or palladium catalyzed Buchwald-Hartwig conditions. Suitable benzobisoxazole, benzobisthiazole and benzobisimidazole base skeletons are either commercially available, or can be obtained by processes known to those skilled in the art. Reference is made to JP10340786, KR20110085784A and KR101160670.

The following examples are included for illustrative purposes only and do not limit the scope of the claims. Unless otherwise stated, all parts and percentages are by weight.

EXAMPLES

Example 1

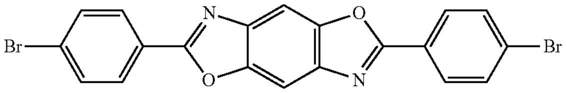 [SMILES: Brc1ccc(-c2nc3cc4oc(-c5ccc(Br)cc5)nc4cc3o2)cc1]

a) 1,4-Diaminohydroquinone-HCl (14.08 mol) and polyphosphoric acid (60 g) are placed in a 300 ml flask. While stirring, 4-bromobenzoic acid (28.16 mol) is added. The mixture is heated at 150° C. overnight (20 hours). After cooling to room temperature, the mixture is poured into $H_2O$ and generated solid is filtered and washed with Saturated $NaHCO_3$ aq, $H_2O$ and EtOH. Dark grey solid is obtained by drying in vacuum (yield: 84.4%).

(A-1)

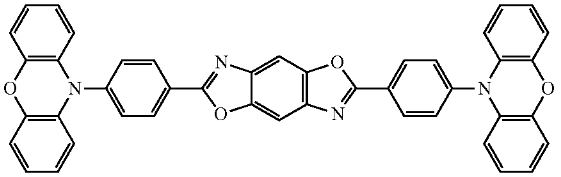

b) The product from example 1a (0.62 mmol), phenoxazine (1.27 mmol), palladium acetate (0.01 mmol), tri-tert-buthylphosphine (0.03 mmol), sodium t-buthoxide (1.85 mmol) and 14 ml of toluene are placed in a 50 ml flask. The mixture is stirred at 110° C. overnight and cooled. The mixture is filtered and the solid is washed with toluene, EtOH, $H_2O$ and MeOH. Yellow solid is obtained by drying in vacuum (yield: 37.4%). The product is subsequently purified using zone sublimation. 1H-NMR (ppm, CDCl3): 8.52 (d, 4H), 8.00 (s, 2H), 7.57 (d, 4H), 6.78-6.60 (m, 12H), 6.02 (d, 4H)

Example 2

(A-2)

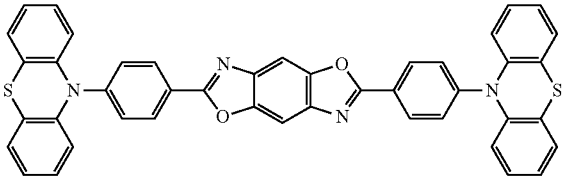

The product from example 1a (1.06 mmol), phenothiazine (2.18 mmol), palladium acetate (0.02 mmol), tri-tert-buthylphosphine (0.04 mmol), sodium t-buthoxide (3.19 mmol) and 24 ml of toluene are placed in a 50 ml flask. The mixture is stirred at 110° C. overnight and cooled. The mixture is filtered and the solid is washed with toluene:hexane=1:1, EtOH, $H_2O$ and MeOH. Yellow solid is obtained by drying in vacuum (yield: 37.4%). The product is subsequently purified using zone sublimation. 1H-NMR (ppm, CDC13): 8.31 (d, 4H), 7.91 (s, 2H), 7.38 (d, 4H), 7.13 (t, 4H), 7.04 (t, 4H), 7.04 (t, 4H), 6.86 (d, 4H)

Example 3

(A-3)

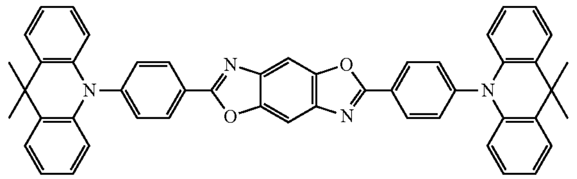

The product from example 1a (2.13 mmol), 9,9-dimethyl-10H-acridine (4.36 mmol), palladium acetate (0.04 mmol), tri-tert-buthylphosphine (0.09 mmol), sodium t-buthoxide (6.38 mmol) and 12 ml of toluene are placed in a 50 ml flask. The mixture is stirred at 110° C. overnight and cooled. The mixture is poured into $H_2O$, yielding precipitation. The solid is filtered and washed with $H_2O$, followed by EtOH. The crude product is purified by flash chromatography on silica gel with $CH_2Cl_2$ and hexane (1:3) as eluent, yielding yellowish solid (yield: 57.5%). The product is subsequently purified using zone sublimation. 1H-NMR (ppm, CDC13): 8.56 (d, 4H), 8.03 (s, 2H), 7.57 (d, 4H), 7.49 (t, 4H), 6.94-7.02 (m, 8H), 6.36 (d, 4H), 1.72 (s, 12H).

Application Example 1 a) Photoluminescent Characterization in Neat Film

On a silicon substrate, compound (A-1) is vacuum-deposited in a thickness of 50 nm. Absorption, fluorescent spectra (excitation at 531 nm) and photoelectron yield spectroscopy of the film are measured, subsequently HOMO and LUMO (eV) of the compound are estimated as 5.71 eV and 3.18 eV, respectively.

b) Photoluminescent Characterization in Host-Guest Film

On a silicon substrate, mCBP doped with 10.2 w % of compound (A-1) is co-deposited in a thickness of 100 nm. The time-resolved and temperature-dependent emission spectra of the host-guest film are measured by photoluminescence spectroscopy with a streak camera. The prompt (~15 ns) and delayed (>0.5 ms) fluorescent components and the temperature dependency are observed as shown Table 1. The host-guest film shows an emission peak at 525 nm in PL spectrum.

TABLE 1

Temperature dependence of PL emission of codeposited film (mCBP doped with 10.2 w % of compound (A-1)) (streak camera)

| Temperature (K) | Prompt PL intensity (a.u.) | Delayed PL intensity (a.u.) |
|---|---|---|
| 8 | 0.82 | 0.04 |
| 68 | 0.90 | 0.05 |
| 140 | 0.87 | 0.15 |
| 200 | 0.96 | 0.49 |

TABLE 1-continued

Temperature dependence of PL emission of codeposited film (mCBP doped with 10.2 w % of compound (A-1)) (streak camera)

| Temperature (K) | Prompt PL intensity (a.u.) | Delayed PL intensity (a.u.) |
|---|---|---|
| 250 | 0.95 | 0.83 |
| 280 | 1 | 0.93 |
| 198 | 0.98 | 1 |

These results indicate that compound (A-1) is a TADF material.

Application Example 2

An organic light emitting device (OLED) is fabricated by vacuum deposition of ITO (100 nm)/5 dipyrazino[2,3-f:2',3'-h]quinoxaline-2,3,6,7,10,11-hexacarbonitrile (HAT-CN) (10 nm)

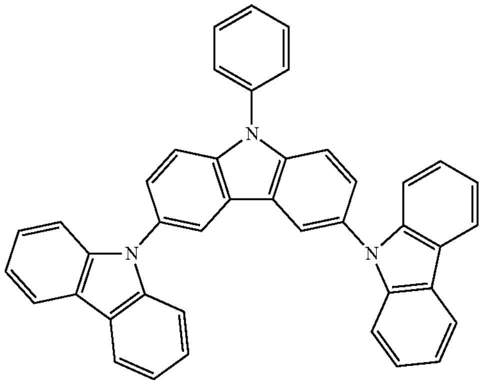 [SMILES: c1ccc(-n2c3ccc(-n4c5ccccc5c5ccccc54)cc3c3cc(-n4c5ccccc5c5ccccc54)ccc32)cc1]

(Tris-PCz, 30 nm)/89.5 w % 3,3-di(9H-carbazol-9-yl)biphenyl (mCBP): 10.5 w % compound A-1 (30 nm)/2,4,6-tris (biphenyl-3-yl)-1,3,5-triazine (T2T, 10 nm)

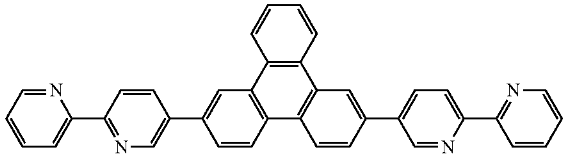

(Bpy-TP2, 40 nm)/LiF (0.8 nm)/Al (100 nm) on a glass substrate, subsequently the device is encapsulated and the performance of the device is evaluated. The device shows an emission peak at 533 nm in electroluminescence (EL) spectrum with an external quantum efficiency (EQE) of 11.6% which is higher than the theoretical value of conventional fluorescent materials (EQE=5-7.5%).

Application Example 3

Application Example 2 is repeated except that compound A-1 is replaced by compound A-2 with 91.3 w % mCBP:8.7 w % compound A-2. The device shows an emission peak at 531 nm in electroluminescence (EL) spectrum with an external quantum efficiency (EQE) of 9.36%.

The invention claimed is:

1. A compound of formula I (I)

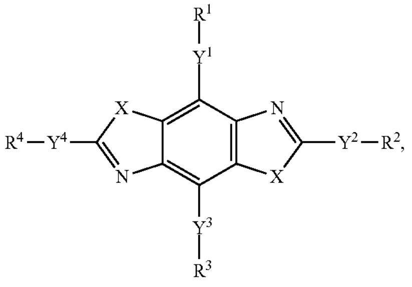

wherein

X is independently in each occurrence O, S or $NR^9$, $Y^1$, $Y^2$, $Y^3$ and $Y^4$ are independently of each other a direct bond, or a group of formula $-[A^1]-[A^2]_y-$, wherein $A^1$ and $A^2$ are independently of each other —CH═CH—, —C≡C— or a $C_6$-$C_{10}$arylene group, which may optionally be substituted by one or more $C_1$-$C_{25}$alkyl groups;

y is 0, or 1;

$R^1$, $R^2$, $R^3$ and $R^4$ are independently of each other H, D, F, Cl, a $C_1$-$C_{25}$alkyl group, a $C_1$-$C_{25}$alkoxy group, a $C_6$-$C_{10}$aryloxy group, or a donor group of formula (Xa)

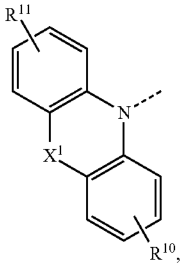

or (Xd)

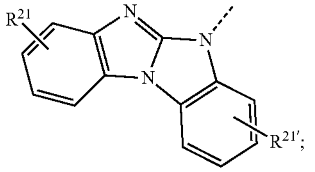

$X^1$ is O, S, $N(R^{15})$, C(═O), $C(R^{16})(R^{17})$, $B(R^{18})$, or $Si(R^{19})(R^{20})$, $R^9$ is H, a $C_1$-$C_{25}$alkyl group, or a $C_6$-$C_{10}$aryl group;

$R^{10}$, $R^{11}$, $R^{21}$ and $R^{21'}$ are independently of each other H, D, F, Cl, or a $C_1$-$C_{25}$alkyl group;

$R^{15}$, $R^{16}$, $R^{17}$, $R^{18}$, $R^{19}$ and $R^{20}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group;

provided that all of conditions (i) to (iii) are satisfied:

(i) at least one donor group of formula (Xa) or (Xd) is present in the compound of formula (I);

(ii) if $Y^2$ and $Y^4$ each represents $C_6$ arylene, then $X^1$ is $NR^{15}$, (C═O), $C(R^{16})(R^{17})$, $B(R^{18})$, or $Si(R^{19})(R^{20})$, wherein $R^{16}$, $R^{17}$, $R^{19}$, and $R^{20}$ are not methyl and $R^{15}$ is not methyl or a $C_6$-$C_{14}$aryl group; and (iii) the compound of Formula (I) is not represented by compound (A-1), (A-2), (A-5), (A-6), (A-8), (B-1), (B-2), (B-5), (B-6), or (B-8):

(A-1)

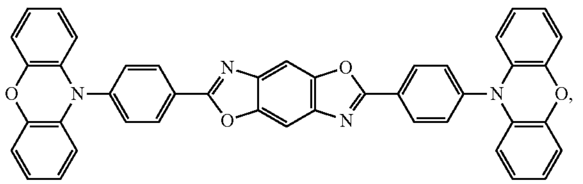

(A-2)

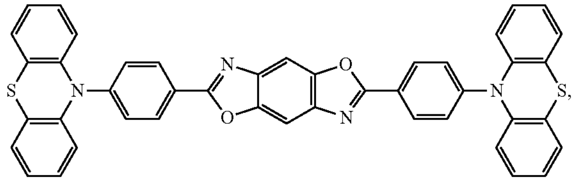

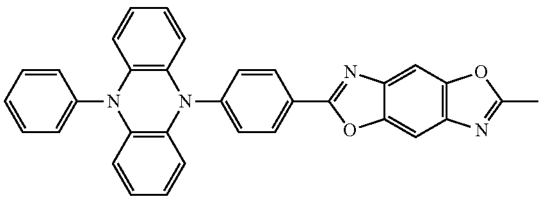

(A-5)

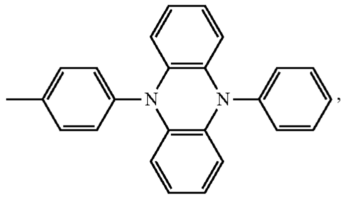

(A-6)

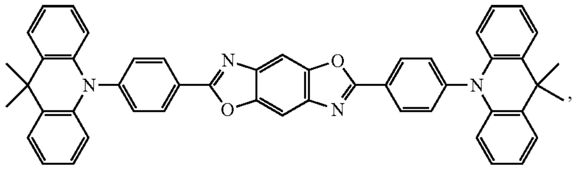

(A-8)

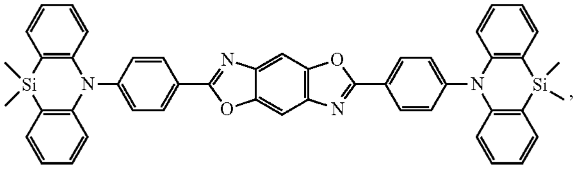

(B-1)

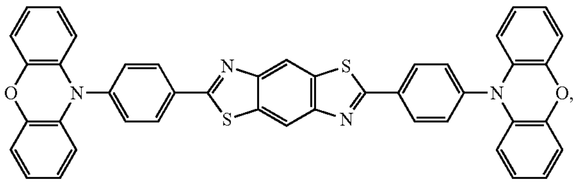

-continued
(B-2)
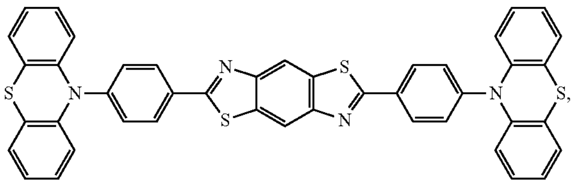
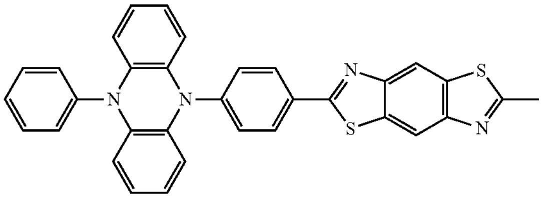
(B-5)
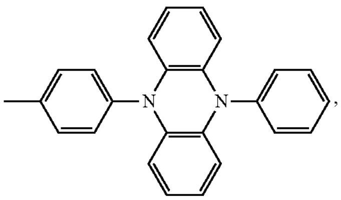
(B-6)
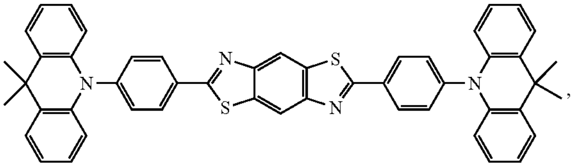
(B-6)
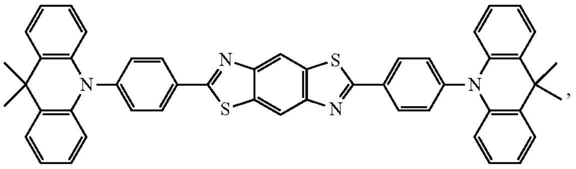
(B-8)
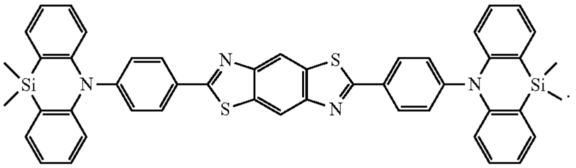
2. The compound according to claim 1, wherein the compound is a compound of any of formula (Ia) to (If)
(Ia)
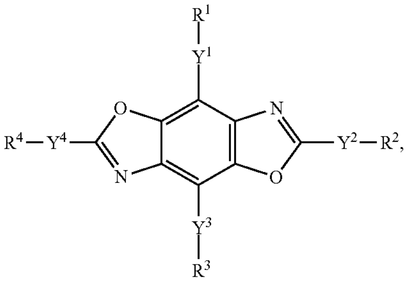
-continued
(Ib)
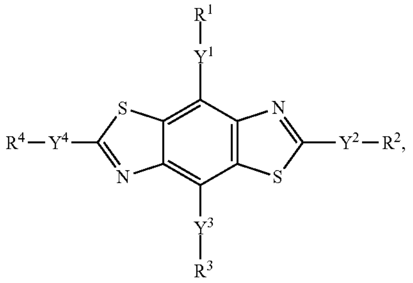
(Ic)
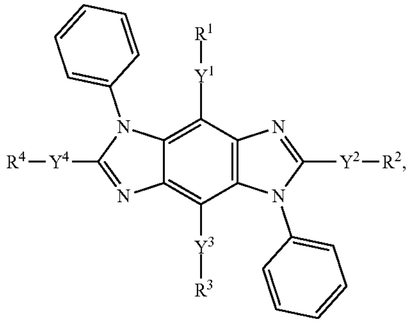
(Id)
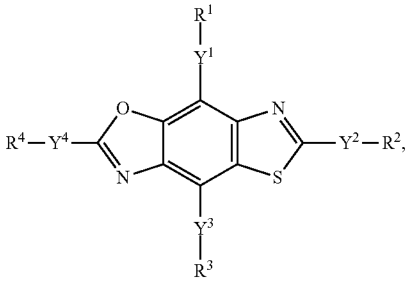
(Ie)
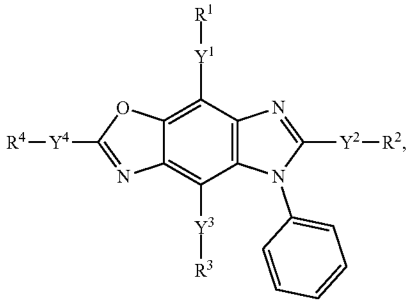
(If)
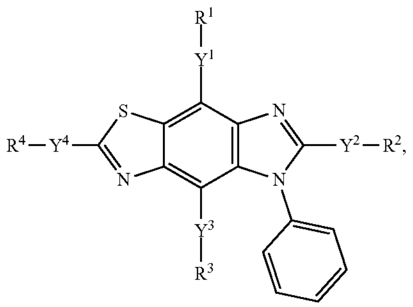
wherein $Y^1$, $Y^2$, $Y^3$, $Y^4$, $R^1$, $R^2$, $R^3$ and $R^4$ are as defined in claim 1.

3. The compound according to claim 2, wherein the compound of formula (I) is a compound of formula (Ia), (Ib), (Ic), (Id), (Ie), or (If), wherein $Y^1$ and $Y^3$ are a direct bond;

$R^1$ and $R^3$ are H;

$Y^2$ and $Y^4$ are a direct bond, or a group of formula

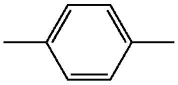
;

$R^2$ and $R^4$ are independently of each other a donor group of formula (Xa), or (Xd); or a compound of formula (Ia), (Ib), (Ic), (Id), (Ie), or (If), wherein $Y^2$ and $Y^4$ are a direct bond;

$R^2$ and $R^4$ are H;

$Y^1$ and $Y^3$ are a direct bond, or a group of formula

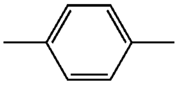
;

$R^1$ and $R^3$ are independently of each other a donor group of formula (Xa), or (Xd); or a compound of formula (Ia), (Ib), (Ic), (Id), (Ie), or (If), wherein $Y^4$ is a direct bond, or a group of formula

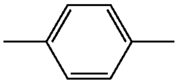
;

$R^4$ is a donor group of formula (Xa), or (Xd);

$Y^2$ is a group of formula

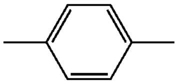
;

$R^2$ is H;

$Y^1$ and $Y^3$ are a direct bond;

$R^1$ and $R^3$ are H; or a compound of formula (Ia), (Ib), (Ic), (Id), (Ie), or (If), wherein $Y^1$ is a direct bond, or a group of formula

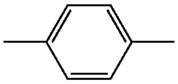
;

$R^1$ is a donor group of formula (Xa), or (Xd);

$Y^2$, $Y^3$ and $Y^4$ are a group of formula

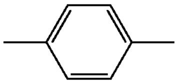
;

$R^2$, $R^3$ and $R^4$ are H, wherein the donor group (Xa) is a group of formula

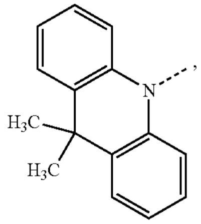
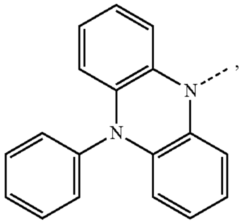

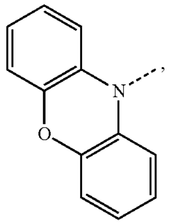
or
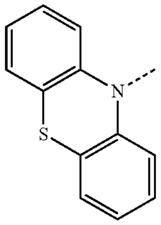

and the donor group (Xd) is a group of formula

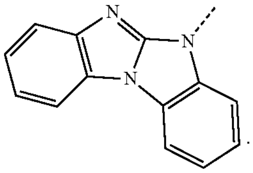

4. The compound according to claim 1 wherein $Y^1$, $Y^2$, $Y^3$ and $Y^4$ are independently of each other a direct bond, or a group of formula

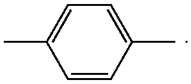
.

5. The compound according to claim 1, wherein $R^1$, $R^2$, $R^3$ and $R^4$ are independently of each other H, a $C_1$-$C_{25}$alkyl group, a $C_1$-$C_{25}$alkoxy group, a $C_6$-$C_{10}$aryloxy group, a donor group of formula (Xa)

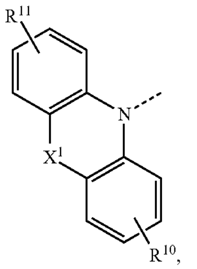
or

-continued (Xd)

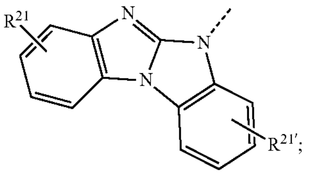

$X^1$ is O, S, C(O), $N(R^{15})$, or $C(R^{16})(R^{17})$; and $R^{10}$, $R^{11}$, $R^{21}$ and $R^{21'}$ are independently of each other H, or a $C_1$-$C_{25}$alkyl group;

$R^{15}$ is a group of formula

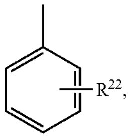

or

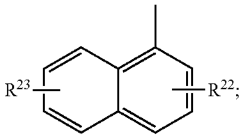

$R^{16}$ and $R^{17}$ are independently of each other H, a $C_1$-$C_{25}$alkyl group;

$R^{22}$ and $R^{23}$ are independently of each other H, a $C_1$-$C_{25}$alkyl group, a $C_1$-$C_{25}$alkoxy group, or a $C_6$-$C_{10}$aryloxy group;

with the proviso that at least one of $R^1$, $R^2$, $R^3$ and $R^4$ is a donor group of formula (Xa) or (Xd).

6. The compound according to claim 5, wherein the donor group is a donor group of formula (Xa), wherein $X^1$ is O, S, $C(CH_3)(CH_3)$, C(═O),

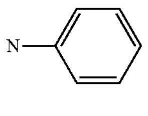

;

or a donor group of formula (Xd), wherein $R^{21}$ and $R^{21'}$ are H.

7. The compound according to claim 1, wherein the donor group is a group of formula

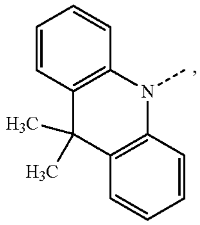

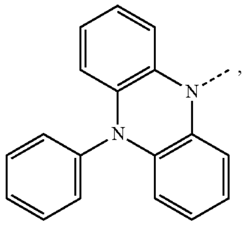

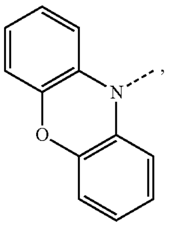

or

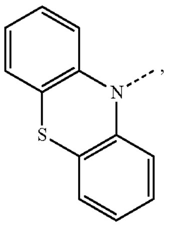

or

-continued

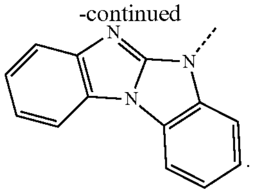

8. The compound according to claim 1, wherein the compound exhibits delayed fluorescence emission.

9. The compound according to claim 1, wherein X is $NR^9$.

10. A light-emitting layer comprising the compound according to claim 1.

11. An organic light emitting element, comprising the compound of formula (I) according to claim 1.

12. The organic light-emitting element according to claim 11, comprising a light-emitting layer, wherein the light-emitting layer comprises a host material and a guest material, wherein the guest material comprises the compound of formula (I).

13. The organic light-emitting element according to claim 11, comprising a light-emitting layer, wherein the light-emitting layer comprises a host material and a guest material, wherein the host material comprises the compound of formula (I).

14. The organic light-emitting element according to claim 11, wherein the organic light-emitting element emits delayed fluorescence.

15. A device selected from the group consisting of a electrophotographic photoreceptor, photoelectric converter, sensor, dye laser, solar cell device and organic light emitting element, wherein the device comprises a compound according to claim 1.

16. An organic light emitting element comprising a compound of formula (I); and an organic compound having a higher value of at least one of excited singlet energy and excited triplet energy than the compound of formula (I);

(I)

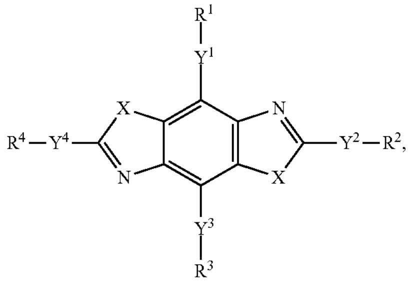

wherein

X is independently in each occurrence O, S or $NR^9$, $Y^1$, $Y^2$, $Y^3$ and $Y^4$ are independently of each other a direct bond, or a group of formula $-[A^1]-[A^2]_y-$, wherein $A^1$ and $A^2$ are independently of each other —CH═CH—, —C≡C— or a $C_6$-$C_{10}$arylene group, which may optionally be substituted by one or more $C_1$-$C_{25}$alkyl groups;

y is 0, or 1;

$R^1$, $R^2$, $R^3$ and $R^4$ are independently of each other H, D, F, Cl, a $C_1$-$C_{25}$alkyl group, a $C_1$-$C_{25}$alkoxy group, a $C_6$-$C_{10}$aryloxy group, or a donor group of formula (Xa)

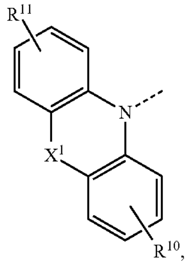

or (Xd)

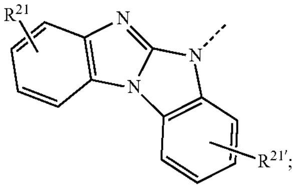

;

$X^1$ is O, S, $N(R^{15})$, C(═O), $C(R^{16})(R^{17})$, $B(R^{18})$, or $Si(R^{19})(R^{20})$, $R^9$ is H, a $C_1$-$C_{25}$alkyl group, or a $C_6$-$C_{10}$aryl group;

$R^{10}$, $R^{11}$, $R^{21}$ and $R^{21'}$ are independently of each other H, D, F, Cl, or a $C_1$-$C_{25}$alkyl group;

$R^{15}$, $R^{16}$, $R^{17}$, $R^{18}$, $R^{19}$ and $R^{20}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group;

provided that all of conditions (i) to (iii) are satisfied:

(i) at least one donor group of formula (Xa) or (Xd) is present in the compound of formula (I);

(ii) if $Y^2$ and $Y^4$ each represents $C_6$ arylene, then $X^1$ is $NR^{15}$, (C═O), $C(R^{16})(R^{17})$, $B(R^{18})$, or $Si(R^{19})(R^{20})$, wherein $R^{16}$, $R^{17}$, $R^{19}$, and $R^{20}$ are not methyl and $R^{15}$ is not methyl or a $C_6$-$C_{14}$aryl group; and (iii) the compound of Formula (I) is not represented by compound (A-1), (A-2), (A-5), (A-6), (A-8), (B-1), (B-2), (B-5), (B-6), or (B-8):

(A-1)

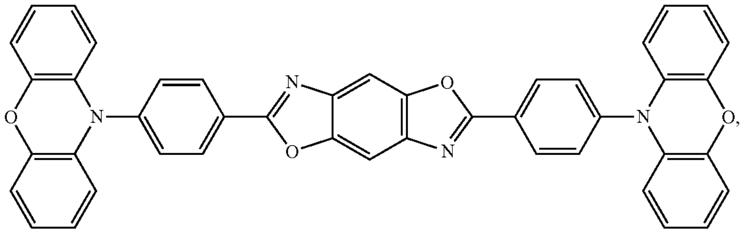

, (A-2)

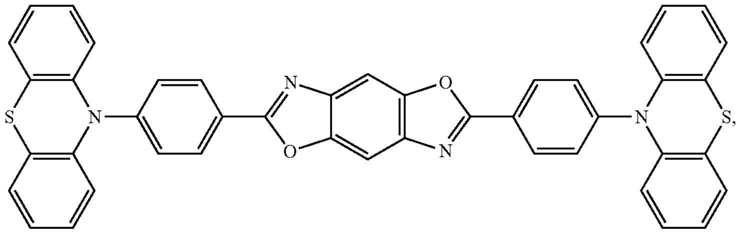

, (A-5)

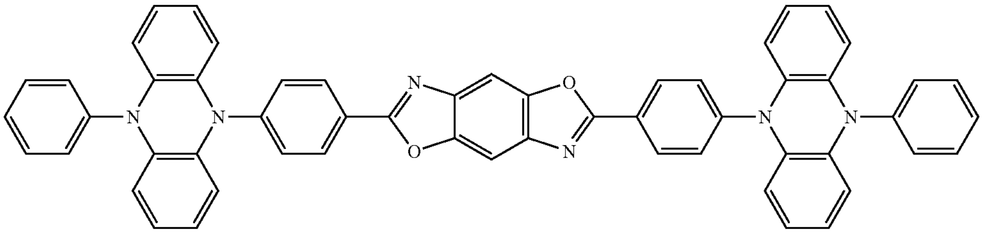

, (A-6)

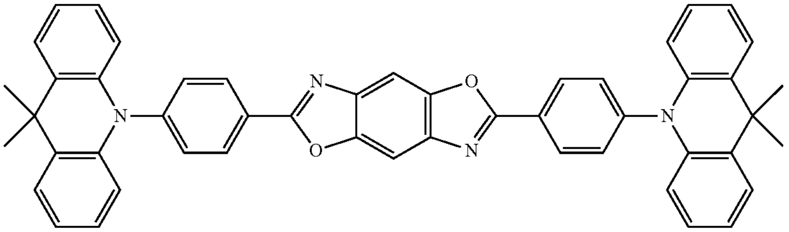

,

-continued
(A-8)
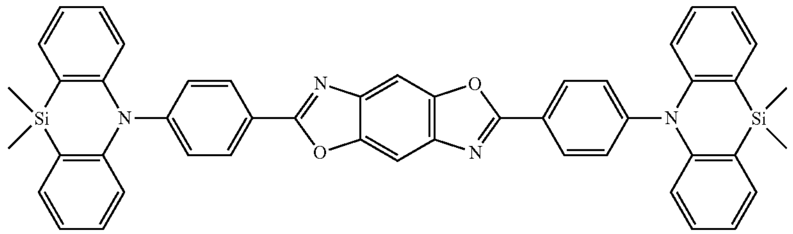
,
(B-1)
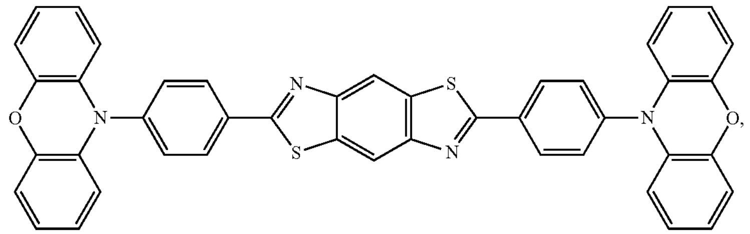
,
(B-2)
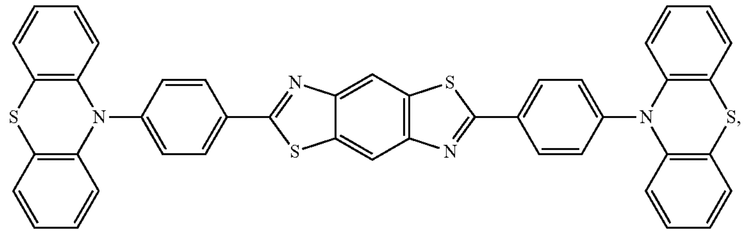
,
(B-5)
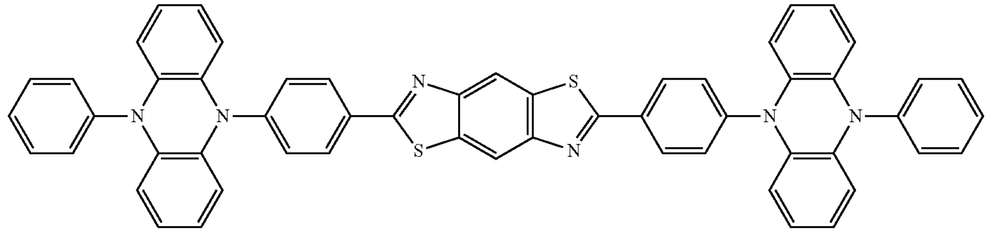
,
(B-6)
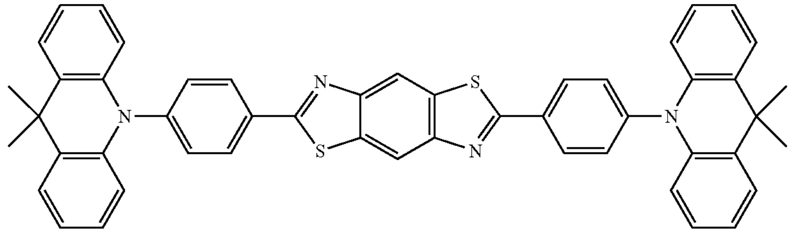
,
(B-6)
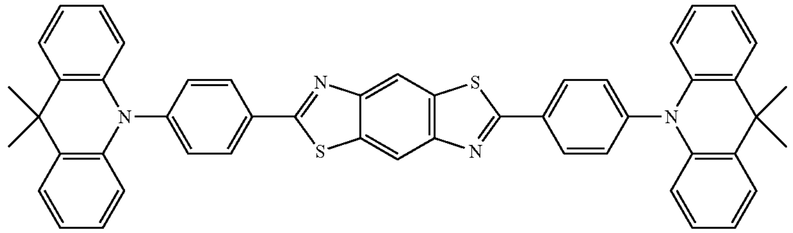

-continued (B-8)

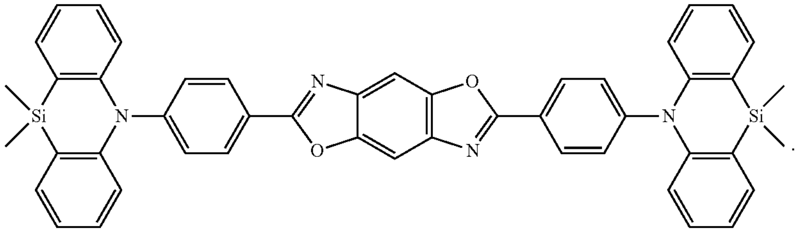

17. The organic light emitting element according to claim 16, wherein the organic compound has a higher excited triplet energy than the compound of formula (I).

18. The organic light emitting element according to claim 16, wherein the compound of formula (I) and the organic compound having a higher value of at least one of excited singlet energy and excited triplet energy than the compound of formula (I) are each present in a light-emitting layer.

* * * * *